United States Patent
Tanaka et al.

(10) Patent No.: US 12,144,513 B2
(45) Date of Patent: Nov. 19, 2024

(54) VERTEBRAL JOINT ACCESS AND DECORTICATION DEVICES AND METHODS OF USING

(71) Applicant: Providence Medical Technology, Inc., Pleasanton, CA (US)

(72) Inventors: Shigeru Tanaka, Half Moon Bay, CA (US); Christopher U. Phan, Dublin, CA (US); Nicholas Domek, Walnut Creek, CA (US); Christopher Lambert, Concord, CA (US); Bon Champ, Campbell, CA (US); Edward Liou, Pleasanton, CA (US); Jamieson Scott Glenn, Cardiff, CA (US); Alessandro Sensoli, Walnut Creek, CA (US); Kehui Chen, Seymour, CT (US); Martin Leugers, San Francisco, CA (US)

(73) Assignee: Providence Medical Technology, Inc., Pleasanton, CA (US)

( * ) Notice: Subject to any disclaimer, the term of this patent is extended or adjusted under 35 U.S.C. 154(b) by 217 days.

(21) Appl. No.: 17/278,422

(22) PCT Filed: Sep. 20, 2019

(86) PCT No.: PCT/US2019/052172
§ 371 (c)(1),
(2) Date: Mar. 22, 2021

(87) PCT Pub. No.: WO2020/061464
PCT Pub. Date: Mar. 26, 2020

(65) Prior Publication Data
US 2021/0386434 A1 Dec. 16, 2021

Related U.S. Application Data

(60) Provisional application No. 62/864,103, filed on Jun. 20, 2019, provisional application No. 62/734,512, filed on Sep. 21, 2018.

(51) Int. Cl.
*A61B 17/16* (2006.01)
*A61B 17/17* (2006.01)
(Continued)

(52) U.S. Cl.
CPC ...... *A61B 17/1671* (2013.01); *A61B 17/1637* (2013.01); *A61B 17/1659* (2013.01);
(Continued)

(58) Field of Classification Search
CPC ..... A61B 17/88; A61B 17/8841; A61B 17/90; A61F 2/4611; A61F 2002/4629
See application file for complete search history.

(56) References Cited

U.S. PATENT DOCUMENTS

| 1,934,962 A | 11/1933 | Barry |
| 2,708,376 A | 5/1955 | Booth |

(Continued)

FOREIGN PATENT DOCUMENTS

| DE | G9304368.6 U1 | 5/2003 |
| FR | 2722980 A1 | 2/1996 |

(Continued)

OTHER PUBLICATIONS

US 7,063,700 B2, 06/2006, Michelson (withdrawn)
(Continued)

*Primary Examiner* — Anu Ramana
(74) *Attorney, Agent, or Firm* — Dorsey & Whitney LLP

(57) ABSTRACT

Devices and methods for improved controlled and targeted decortication of the bone of a spinal facet joint are provided. In one aspect, a decortication tool is provided. The decortication tool may include a shaft with proximal and distal end portions. A handle may be connected to the proximal end portion of the shaft. A decortication head may be coupled to the distal end portion of the shaft. In another aspect, a multi-use instrument for use in a spinal system is (Continued)

provided. The instrument may include a body including opposing first and second sides, and opposing first and second surfaces. A cavity may be defined in the body, the cavity being open to the second surface. The instrument may include a bar attached to the second side of the body. A portion of the bar may extend beyond the second surface of the body.

19 Claims, 54 Drawing Sheets

(51) Int. Cl.
    *A61B 17/70*     (2006.01)
    *A61B 90/00*     (2016.01)

(52) U.S. Cl.
    CPC ...... *A61B 17/1757* (2013.01); *A61B 17/7064* (2013.01); *A61B 90/08* (2016.02); *A61B 90/39* (2016.02); *A61B 2090/0811* (2016.02)

(56) References Cited

U.S. PATENT DOCUMENTS

| | | | |
|---|---|---|---|
| 2,984,241 A | 5/1961 | Carlson | |
| 3,486,505 A | 12/1969 | Morrison | |
| 4,463,753 A | 8/1984 | Gustilo | |
| 4,479,491 A | 10/1984 | Martin | |
| 4,530,355 A | 7/1985 | Griggs | |
| 4,604,995 A | 8/1986 | Stephens et al. | |
| 4,736,738 A | 4/1988 | Lipovsek et al. | |
| 4,759,769 A | 7/1988 | Hedman et al. | |
| 4,772,287 A | 9/1988 | Ray et al. | |
| 4,877,020 A | 10/1989 | Vich | |
| 4,878,915 A | 11/1989 | Brantigan | |
| 5,015,247 A | 5/1991 | Michelson | |
| 5,026,373 A | 6/1991 | Ray et al. | |
| 5,100,405 A | 3/1992 | McLaren | |
| 5,135,528 A | 8/1992 | Winston | |
| 5,192,327 A | 3/1993 | Brantigan | |
| 5,236,460 A | 8/1993 | Barber | |
| 5,443,514 A | 8/1995 | Steffee | |
| 5,484,437 A | 1/1996 | Michelson | |
| 5,489,307 A | 2/1996 | Kuslich et al. | |
| 5,505,732 A | 4/1996 | Michelson | |
| 5,527,312 A | 6/1996 | Ray | |
| 5,549,679 A | 8/1996 | Kuslich | |
| 5,554,191 A | 9/1996 | Lahille et al. | |
| 5,571,109 A | 11/1996 | Bertagnoli | |
| 5,571,191 A | 11/1996 | Fitz | |
| 5,584,832 A | 12/1996 | Schlapfer et al. | |
| 5,593,409 A | 1/1997 | Michelson | |
| 5,632,747 A | 5/1997 | Scarborough et al. | |
| 5,649,945 A | 7/1997 | Ray et al. | |
| 5,653,763 A | 8/1997 | Errico et al. | |
| 5,665,122 A | 9/1997 | Kambin | |
| 5,674,295 A | 10/1997 | Ray et al. | |
| 5,702,443 A | 12/1997 | Braanemark | |
| 5,720,748 A | 2/1998 | Kuslich et al. | |
| 5,741,253 A | 4/1998 | Michelson | |
| 5,772,661 A | 6/1998 | Michelson | |
| 5,792,044 A | 8/1998 | Foley et al. | |
| 5,797,909 A | 8/1998 | Michelson | |
| 5,836,948 A | 11/1998 | Zucherman et al. | |
| 5,879,353 A | 3/1999 | Terry | |
| 5,885,299 A | 3/1999 | Winslow et al. | |
| 5,891,147 A | 4/1999 | Moskovitz | |
| 5,895,426 A | 4/1999 | Scarborough et al. | |
| 5,899,908 A | 5/1999 | Kuslich et al. | |
| 5,906,616 A | 5/1999 | Pavlov et al. | |
| 5,928,238 A | 7/1999 | Scarborough et al. | |
| 5,953,820 A | 9/1999 | Vasudeva | |
| 5,961,522 A | 10/1999 | Mehdizadeh | |
| 5,976,146 A | 11/1999 | Ogawa et al. | |
| 5,989,291 A | 11/1999 | Ralph et al. | |
| 6,008,433 A | 12/1999 | Stone | |
| 6,033,405 A | 3/2000 | Winslow et al. | |
| 6,045,580 A | 4/2000 | Scarborough et al. | |
| 6,063,088 A | 5/2000 | Winslow | |
| RE36,758 E | 6/2000 | Fitz | |
| 6,080,155 A | 6/2000 | Michelson | |
| 6,090,143 A | 7/2000 | Meriwether et al. | |
| 6,096,038 A | 8/2000 | Michelson | |
| 6,099,531 A | 8/2000 | Bonutti | |
| 6,102,950 A | 8/2000 | Vaccaro | |
| 6,113,602 A * | 9/2000 | Sand | A61F 2/4611 |
| | | | 606/279 |
| 6,113,637 A | 9/2000 | Gill et al. | |
| 6,149,650 A | 11/2000 | Michelson | |
| RE37,005 E | 12/2000 | Michelson et al. | |
| 6,159,245 A | 12/2000 | Meriwether et al. | |
| 6,174,311 B1 | 1/2001 | Branch et al. | |
| 6,176,882 B1 | 1/2001 | Biedermann et al. | |
| 6,179,873 B1 | 1/2001 | Zientek | |
| 6,190,388 B1 | 2/2001 | Michelson et al. | |
| 6,190,414 B1 | 2/2001 | Young et al. | |
| 6,193,757 B1 | 2/2001 | Foley et al. | |
| 6,200,322 B1 | 3/2001 | Branch et al. | |
| 6,210,412 B1 | 4/2001 | Michelson | |
| RE37,161 E | 5/2001 | Michelson et al. | |
| 6,224,595 B1 | 5/2001 | Michelson | |
| 6,224,607 B1 | 5/2001 | Michelson | |
| 6,224,630 B1 | 5/2001 | Bao et al. | |
| 6,245,108 B1 | 6/2001 | Biscup | |
| 6,248,110 B1 | 6/2001 | Reiley et al. | |
| 6,248,345 B1 | 6/2001 | Goldenheim et al. | |
| D444,878 S | 7/2001 | Walter | |
| D445,188 S | 7/2001 | Walter | |
| 6,264,656 B1 | 7/2001 | Michelson | |
| 6,267,763 B1 | 7/2001 | Castro | |
| 6,270,498 B1 | 8/2001 | Michelson | |
| 6,283,966 B1 | 9/2001 | Boufburg | |
| 6,315,795 B1 | 11/2001 | Scarborough et al. | |
| 6,325,827 B1 | 12/2001 | Lin | |
| 6,371,984 B1 | 4/2002 | Van Dyke et al. | |
| 6,371,988 B1 | 4/2002 | Pafford et al. | |
| 6,402,784 B1 | 6/2002 | Wardlaw | |
| 6,423,063 B1 | 7/2002 | Bonutti | |
| 6,423,083 B2 | 7/2002 | Reiley et al. | |
| 6,425,919 B1 | 7/2002 | Lambrecht | |
| 6,436,098 B1 | 8/2002 | Michelson | |
| 6,436,142 B1 | 8/2002 | Paes et al. | |
| 6,443,988 B2 | 9/2002 | Felt et al. | |
| 6,451,023 B1 | 9/2002 | Salazar et al. | |
| 6,454,807 B1 | 9/2002 | Jackson | |
| 6,478,796 B2 | 11/2002 | Zucherman et al. | |
| 6,485,518 B1 | 11/2002 | Cornwall et al. | |
| 6,500,206 B1 | 12/2002 | Bryan | |
| 6,514,256 B2 | 2/2003 | Zucherman et al. | |
| 6,524,312 B2 | 2/2003 | Landry et al. | |
| 6,530,955 B2 | 3/2003 | Boyle et al. | |
| 6,537,279 B1 | 3/2003 | Michelson | |
| 6,540,747 B1 | 4/2003 | Marino | |
| 6,558,390 B2 | 5/2003 | Cragg | |
| 6,565,574 B2 | 5/2003 | Michelson | |
| 6,565,605 B2 | 5/2003 | Fallin et al. | |
| 6,569,186 B1 | 5/2003 | Winters et al. | |
| 6,575,899 B1 | 6/2003 | Foley et al. | |
| 6,575,919 B1 | 6/2003 | Reiley et al. | |
| 6,575,979 B1 | 6/2003 | Cragg | |
| 6,579,319 B2 | 6/2003 | Goble et al. | |
| 6,582,432 B1 | 6/2003 | Michelson | |
| 6,582,467 B1 | 6/2003 | Teitelbaum et al. | |
| 6,582,468 B1 | 6/2003 | Gauchet | |
| 6,607,530 B1 | 8/2003 | Carl et al. | |
| 6,610,091 B1 | 8/2003 | Reiley | |
| 6,626,905 B1 | 9/2003 | Schmiel et al. | |
| 6,632,235 B2 | 10/2003 | Weikel et al. | |
| 6,635,060 B2 | 10/2003 | Hanson et al. | |
| 6,641,582 B1 * | 11/2003 | Hanson | A61F 2/4465 |
| | | | 623/17.11 |
| 6,648,893 B2 | 11/2003 | Dudasik | |
| 6,652,584 B2 | 11/2003 | Michelson | |
| 6,663,647 B2 | 12/2003 | Reiley et al. | |

(56) References Cited

U.S. PATENT DOCUMENTS

| | | | |
|---|---|---|---|
| 6,666,866 B2 | 12/2003 | Martz et al. |
| 6,679,886 B2 | 1/2004 | Weikel et al. |
| 6,682,535 B2 | 1/2004 | Hoogland |
| 6,682,562 B2 | 1/2004 | Viart et al. |
| 6,685,742 B1 | 2/2004 | Jackson |
| 6,709,458 B2 | 3/2004 | Michelson |
| 6,712,853 B2 | 3/2004 | Kuslich |
| 6,719,773 B1 | 4/2004 | Boucher et al. |
| 6,719,794 B2 | 4/2004 | Gerber et al. |
| 6,723,095 B2 | 4/2004 | Hammerslag |
| 6,733,534 B2 | 5/2004 | Sherman |
| 6,740,093 B2 | 5/2004 | Hochschuler et al. |
| 6,751,875 B2 | 6/2004 | Jones |
| 6,770,074 B2 * | 8/2004 | Michelson ............ A61F 2/446 623/17.11 |
| 6,793,679 B2 | 9/2004 | Michelson |
| 6,805,715 B2 | 10/2004 | Reuter et al. |
| 6,808,537 B2 | 10/2004 | Michelson |
| 6,814,738 B2 | 11/2004 | Naughton et al. |
| 6,823,871 B2 | 11/2004 | Schmieding |
| 6,840,941 B2 | 1/2005 | Rogers et al. |
| 6,851,430 B2 | 2/2005 | Tsou |
| 6,875,213 B2 | 4/2005 | Michelson |
| 6,899,719 B2 | 5/2005 | Reiley et al. |
| 6,921,403 B2 | 7/2005 | Cragg et al. |
| 6,923,813 B2 | 8/2005 | Phillips |
| 6,958,077 B2 | 10/2005 | Suddaby |
| 6,962,606 B2 | 11/2005 | Michelson |
| 6,964,686 B2 | 11/2005 | Gordon |
| 6,966,930 B2 | 11/2005 | Arnin et al. |
| 6,972,035 B2 | 12/2005 | Michelson |
| 6,974,478 B2 | 12/2005 | Reiley et al. |
| 6,979,333 B2 | 12/2005 | Hammerslag |
| 6,986,772 B2 | 1/2006 | Michelson |
| 7,001,385 B2 | 2/2006 | Bonutti |
| 7,008,453 B1 | 3/2006 | Michelson |
| 7,029,479 B2 | 4/2006 | Tallarida et al. |
| 7,033,362 B2 | 4/2006 | McGahan et al. |
| 7,033,392 B2 | 4/2006 | Schmiel et al. |
| 7,033,394 B2 | 4/2006 | Michelson |
| 7,066,961 B2 | 6/2006 | Michelson |
| D524,443 S | 7/2006 | Blain |
| 7,083,623 B2 | 8/2006 | Michelson |
| 7,090,698 B2 | 8/2006 | Fallin et al. |
| 7,096,972 B2 | 8/2006 | Orozco, Jr. |
| 7,101,398 B2 | 9/2006 | Dooris et al. |
| 7,115,128 B2 | 10/2006 | Michelson |
| 7,118,598 B2 | 10/2006 | Michelson |
| 7,128,760 B2 | 10/2006 | Michelson |
| 7,156,877 B2 | 1/2007 | Lotz et al. |
| 7,166,110 B2 | 1/2007 | Yundt |
| 7,175,023 B2 | 2/2007 | Martin |
| 7,179,263 B2 | 2/2007 | Zdeblick et al. |
| 7,207,991 B2 | 4/2007 | Michelson |
| D541,940 S | 5/2007 | Blain |
| 7,220,280 B2 | 5/2007 | Kast et al. |
| 7,255,703 B2 | 8/2007 | Mujwid et al. |
| 7,261,739 B2 | 8/2007 | Ralph et al. |
| 7,264,622 B2 | 9/2007 | Michelson |
| 7,273,373 B2 | 9/2007 | Horiuchi |
| 7,273,498 B2 | 9/2007 | Bianchi et al. |
| 7,288,093 B2 | 10/2007 | Michelson |
| 7,291,149 B1 | 11/2007 | Michelson |
| 7,300,440 B2 | 11/2007 | Zdeblick et al. |
| 7,326,211 B2 | 2/2008 | Padget et al. |
| 7,326,214 B2 | 2/2008 | Michelson |
| 7,371,238 B2 | 5/2008 | Soboleski et al. |
| 7,399,303 B2 | 7/2008 | Michelson |
| 7,410,501 B2 | 8/2008 | Michelson |
| 7,431,722 B1 | 10/2008 | Michelson |
| 7,445,636 B2 | 11/2008 | Michelson |
| 7,452,359 B1 | 11/2008 | Michelson |
| 7,452,369 B2 | 11/2008 | Barry |
| 7,465,304 B1 | 12/2008 | Haufe et al. |
| 7,476,226 B2 | 1/2009 | Weikel et al. |
| 7,476,251 B2 | 1/2009 | Zucherman et al. |
| 7,479,160 B2 | 1/2009 | Branch et al. |
| 7,491,205 B1 | 2/2009 | Michelson |
| 7,491,240 B1 | 2/2009 | Carver et al. |
| 7,500,992 B2 | 3/2009 | Li |
| 7,517,358 B2 | 4/2009 | Peterson |
| 7,524,333 B2 | 4/2009 | Lambrecht et al. |
| 7,569,054 B2 | 8/2009 | Michelson |
| 7,569,057 B2 | 8/2009 | Liu et al. |
| 7,580,743 B2 | 8/2009 | Bourlion et al. |
| 7,591,851 B2 | 9/2009 | Winslow et al. |
| 7,601,170 B2 | 10/2009 | Winslow et al. |
| 7,608,077 B2 | 10/2009 | Cragg et al. |
| 7,608,107 B2 | 10/2009 | Michelson |
| 7,615,079 B2 | 11/2009 | Flickinger et al. |
| 7,618,451 B2 | 11/2009 | Berez et al. |
| 7,632,291 B2 | 12/2009 | Stephens et al. |
| 7,641,664 B2 | 1/2010 | Pagano |
| 7,648,509 B2 | 1/2010 | Stark |
| 7,648,523 B2 | 1/2010 | Mirkovic et al. |
| 7,655,027 B2 | 2/2010 | Michelson |
| 7,655,043 B2 | 2/2010 | Peterman et al. |
| 7,662,173 B2 | 2/2010 | Cragg et al. |
| D611,147 S | 3/2010 | Hanson et al. |
| 7,682,378 B2 | 3/2010 | Truckai et al. |
| 7,686,805 B2 | 3/2010 | Michelson |
| 7,686,807 B2 | 3/2010 | Padget et al. |
| 7,699,878 B2 | 4/2010 | Pavlov et al. |
| D615,653 S | 5/2010 | Horton |
| 7,708,761 B2 | 5/2010 | Petersen |
| 7,708,766 B2 | 5/2010 | Anderson et al. |
| 7,722,619 B2 | 5/2010 | Michelson |
| D619,719 S | 7/2010 | Pannu |
| D620,113 S | 7/2010 | Courtney et al. |
| 7,763,024 B2 | 7/2010 | Bertagnoli et al. |
| 7,763,050 B2 | 7/2010 | Winslow et al. |
| 7,776,090 B2 | 8/2010 | Winslow et al. |
| D623,748 S | 9/2010 | Horton et al. |
| D623,749 S | 9/2010 | Horton et al. |
| 7,789,898 B2 | 9/2010 | Peterman |
| D627,468 S | 11/2010 | Richter et al. |
| 7,824,431 B2 | 11/2010 | McCormack |
| 7,837,713 B2 | 11/2010 | Petersen |
| 7,846,183 B2 | 12/2010 | Blain |
| 7,846,184 B2 | 12/2010 | Sasso et al. |
| 7,850,733 B2 | 12/2010 | Baynham et al. |
| 7,862,589 B2 | 1/2011 | Thramann |
| 7,867,277 B1 | 1/2011 | Tohmeh |
| D631,967 S | 2/2011 | Horton |
| 7,879,098 B1 | 2/2011 | Simmons, Jr. |
| 7,883,336 B2 | 2/2011 | Hansson |
| 7,887,565 B2 | 2/2011 | Michelson |
| 7,892,261 B2 | 2/2011 | Bonutti |
| 7,892,286 B2 | 2/2011 | Michelson |
| 7,896,803 B2 | 3/2011 | Schara et al. |
| 7,896,903 B2 | 3/2011 | Link |
| 7,901,439 B2 | 3/2011 | Horton |
| 7,914,530 B2 | 3/2011 | Michelson |
| 7,918,891 B1 | 4/2011 | Curran et al. |
| 7,922,729 B2 | 4/2011 | Michelson |
| 7,922,766 B2 | 4/2011 | Grob et al. |
| 7,935,136 B2 | 5/2011 | Alamin et al. |
| 7,938,857 B2 | 5/2011 | Krueger et al. |
| 7,942,903 B2 | 5/2011 | Moskowitz et al. |
| 7,988,712 B2 | 8/2011 | Hale et al. |
| 7,988,714 B2 | 8/2011 | Puekert et al. |
| 7,998,174 B2 | 8/2011 | Malandain et al. |
| 8,007,534 B2 | 8/2011 | Michelson |
| 8,029,540 B2 | 10/2011 | Winslow et al. |
| 8,043,334 B2 | 10/2011 | Fisher et al. |
| 8,052,728 B2 | 11/2011 | Hestad |
| 8,062,299 B2 | 11/2011 | Mcgahan et al. |
| 8,062,303 B2 | 11/2011 | Berry et al. |
| 8,066,705 B2 | 11/2011 | Michelson |
| D650,481 S | 12/2011 | Gottlieb et al. |
| 8,092,475 B2 * | 1/2012 | Cotter ............ A61B 17/1688 606/169 |
| 8,097,034 B2 | 1/2012 | Michelson |
| 8,100,944 B2 | 1/2012 | Lauryssen et al. |

(56) References Cited

U.S. PATENT DOCUMENTS

| | | | |
|---|---|---|---|
| D653,757 S | 2/2012 | Binder | |
| 8,114,158 B2 | 2/2012 | Carl et al. | |
| 8,118,838 B2 | 2/2012 | Winslow et al. | |
| 8,128,660 B2 | 3/2012 | Mitchell et al. | |
| 8,133,261 B2 | 3/2012 | Fisher et al. | |
| 8,142,503 B2 | 3/2012 | Malone | |
| 8,147,553 B2 | 4/2012 | Vresilovic et al. | |
| 8,162,981 B2 | 4/2012 | Vestgaarden | |
| 8,172,877 B2 | 5/2012 | Winslow et al. | |
| 8,197,513 B2 | 6/2012 | Fisher et al. | |
| 8,206,418 B2 | 6/2012 | Triplett et al. | |
| 8,267,966 B2 | 9/2012 | McCormack et al. | |
| 8,333,804 B1 | 12/2012 | Wensel | |
| D674,900 S | 1/2013 | Janice et al. | |
| 8,348,979 B2 | 1/2013 | McCormack | |
| 8,361,152 B2 | 1/2013 | McCormack et al. | |
| 8,366,747 B2 | 2/2013 | Shluzas | |
| 8,366,748 B2 | 2/2013 | Kleiner | |
| 8,382,767 B2 | 2/2013 | Wassinger et al. | |
| D677,791 S | 3/2013 | Danacioglu et al. | |
| 8,394,107 B2 | 3/2013 | Fanger et al. | |
| 8,394,129 B2 | 3/2013 | Morgenstern et al. | |
| D681,205 S | 4/2013 | Farris et al. | |
| 8,425,558 B2 | 4/2013 | McCormack et al. | |
| 8,439,922 B1 | 5/2013 | Arnold et al. | |
| 8,512,347 B2 | 8/2013 | McCormack et al. | |
| 8,518,090 B2 | 8/2013 | Huebner et al. | |
| 8,523,908 B2 | 9/2013 | Malone | |
| 8,529,609 B2 | 9/2013 | Helgerson et al. | |
| 8,623,054 B2 * | 1/2014 | McCormack | A61B 17/8819 606/247 |
| 8,668,722 B2 | 3/2014 | Pavlov et al. | |
| 8,753,345 B2 * | 6/2014 | McCormack | H04L 45/02 606/86 R |
| 8,753,347 B2 | 6/2014 | McCormack et al. | |
| 8,764,755 B2 | 7/2014 | Michelson | |
| 8,828,062 B2 | 9/2014 | McCormack et al. | |
| 8,834,530 B2 | 9/2014 | McCormack | |
| 8,845,727 B2 | 9/2014 | Gottlieb et al. | |
| 8,870,882 B2 | 10/2014 | Kleiner | |
| D723,690 S | 3/2015 | McCormack et al. | |
| D723,691 S | 3/2015 | McCormack et al. | |
| 8,998,905 B2 | 4/2015 | Marik et al. | |
| 9,005,288 B2 | 4/2015 | Mccormack et al. | |
| 9,011,492 B2 | 4/2015 | McCormack et al. | |
| 9,039,766 B1 | 5/2015 | Fonte | |
| D732,667 S | 6/2015 | McCormack et al. | |
| 9,186,193 B2 | 11/2015 | Kleiner et al. | |
| D745,156 S | 12/2015 | McCormack et al. | |
| 9,211,198 B2 | 12/2015 | Michelson | |
| 9,220,608 B2 | 12/2015 | McKay | |
| D750,249 S | 2/2016 | Grimberg, Jr. et al. | |
| 9,271,765 B2 | 3/2016 | Blain | |
| 9,333,086 B2 | 5/2016 | McCormack et al. | |
| 9,339,263 B2 | 5/2016 | Fenn et al. | |
| 9,358,127 B2 | 6/2016 | Duffield et al. | |
| 9,381,049 B2 | 7/2016 | McCormack et al. | |
| 9,427,264 B2 | 8/2016 | Kleiner et al. | |
| 9,504,583 B2 | 11/2016 | Blain | |
| 9,622,791 B2 | 4/2017 | Mccormack et al. | |
| 9,622,873 B2 | 4/2017 | Mccormack | |
| 9,622,874 B2 | 4/2017 | Mccormack et al. | |
| 9,629,665 B2 | 4/2017 | Mccormack et al. | |
| 9,707,650 B2 * | 7/2017 | Tiefenbock | B23Q 1/34 |
| 9,717,403 B2 | 8/2017 | Kleiner et al. | |
| 9,937,053 B2 | 4/2018 | Melkent et al. | |
| 10,039,649 B2 | 8/2018 | Mccormack et al. | |
| 10,149,673 B2 | 12/2018 | Mccormack et al. | |
| 10,172,721 B2 | 1/2019 | Mccormack et al. | |
| D841,165 S | 2/2019 | Mccormack et al. | |
| D841,167 S | 2/2019 | Ricca et al. | |
| 10,201,375 B2 | 2/2019 | Mccormack et al. | |
| 10,206,787 B2 | 2/2019 | Voellmicke | |
| 10,219,910 B2 | 3/2019 | Mccormack | |
| 10,226,285 B2 | 3/2019 | Mccormack et al. | |
| 10,238,501 B2 | 3/2019 | Mccormack et al. | |
| 10,327,913 B2 | 6/2019 | Palmatier et al. | |
| 10,456,175 B2 | 10/2019 | McCormack et al. | |
| 10,568,666 B2 | 2/2020 | Mccormack et al. | |
| 10,588,672 B2 | 3/2020 | Mccormack et al. | |
| D884,895 S | 5/2020 | Mccormack et al. | |
| D887,552 S | 6/2020 | Tanaka et al. | |
| 10,682,243 B2 | 6/2020 | Phan et al. | |
| D911,525 S | 2/2021 | Tanaka et al. | |
| 10,907,417 B2 * | 2/2021 | Brady | E21B 10/58 |
| RE48,501 E | 4/2021 | McCormack et al. | |
| 11,058,466 B2 | 7/2021 | Mccormack et al. | |
| 11,272,964 B2 | 3/2022 | Mccormack et al. | |
| 11,285,010 B2 | 3/2022 | Mccormack | |
| 11,648,128 B2 | 5/2023 | Tanaka et al. | |
| 12,004,781 B2 | 6/2024 | McCormack et al. | |
| 2001/0004710 A1 | 6/2001 | Felt et al. | |
| 2001/0007074 A1 | 7/2001 | Strobel et al. | |
| 2001/0047208 A1 | 11/2001 | Michelson | |
| 2001/0053914 A1 | 12/2001 | Landry et al. | |
| 2002/0026195 A1 | 2/2002 | Layne et al. | |
| 2002/0068941 A1 * | 6/2002 | Hanson | A61F 2/4611 606/79 |
| 2002/0077641 A1 | 6/2002 | Michelson | |
| 2002/0107519 A1 | 8/2002 | Dixon et al. | |
| 2002/0143343 A1 | 10/2002 | Castro | |
| 2002/0147496 A1 | 10/2002 | Belef et al. | |
| 2002/0147497 A1 | 10/2002 | Belef et al. | |
| 2002/0165612 A1 | 11/2002 | Gerber et al. | |
| 2002/0169471 A1 | 11/2002 | Ferdinand | |
| 2002/0177866 A1 | 11/2002 | Weikel et al. | |
| 2003/0023312 A1 | 1/2003 | Thalgott | |
| 2003/0028251 A1 | 2/2003 | Mathews | |
| 2003/0032962 A1 | 2/2003 | McGahan et al. | |
| 2003/0033017 A1 | 2/2003 | Lotz et al. | |
| 2003/0040801 A1 | 2/2003 | Ralph et al. | |
| 2003/0060887 A1 | 3/2003 | Ek | |
| 2003/0077134 A1 * | 4/2003 | Moser | B23B 51/02 408/231 |
| 2003/0083668 A1 | 5/2003 | Rogers et al. | |
| 2003/0083688 A1 | 5/2003 | Simonson | |
| 2003/0105526 A1 | 6/2003 | Bryant et al. | |
| 2003/0109928 A1 | 6/2003 | Pasquet et al. | |
| 2003/0120276 A1 | 6/2003 | Tallarida et al. | |
| 2003/0139816 A1 | 7/2003 | Michelson | |
| 2003/0144737 A1 | 7/2003 | Sherman | |
| 2003/0149438 A1 | 8/2003 | Nichols et al. | |
| 2003/0158553 A1 | 8/2003 | Michelson | |
| 2003/0225416 A1 | 12/2003 | Bonvallet et al. | |
| 2004/0010259 A1 | 1/2004 | Keller et al. | |
| 2004/0059337 A1 | 3/2004 | Hanson et al. | |
| 2004/0073217 A1 | 4/2004 | Michelson | |
| 2004/0087948 A1 | 5/2004 | Suddaby | |
| 2004/0087956 A1 | 5/2004 | Weikel et al. | |
| 2004/0106999 A1 | 6/2004 | Mathews | |
| 2004/0111155 A1 | 6/2004 | Ferree | |
| 2004/0133277 A1 | 7/2004 | Michelson | |
| 2004/0133280 A1 | 7/2004 | Trieu | |
| 2004/0162562 A1 | 8/2004 | Martz | |
| 2004/0215344 A1 | 10/2004 | Hochschuler et al. | |
| 2004/0225292 A1 | 11/2004 | Sasso et al. | |
| 2004/0254575 A1 | 12/2004 | Obenchain et al. | |
| 2005/0010234 A1 | 1/2005 | Ralph et al. | |
| 2005/0010294 A1 | 1/2005 | Michelson | |
| 2005/0015097 A1 | 1/2005 | Mujwid et al. | |
| 2005/0015149 A1 | 1/2005 | Michelson | |
| 2005/0021042 A1 | 1/2005 | Marnay et al. | |
| 2005/0027358 A1 | 2/2005 | Suddaby | |
| 2005/0033432 A1 | 2/2005 | Gordon et al. | |
| 2005/0038511 A1 | 2/2005 | Martz et al. | |
| 2005/0038515 A1 | 2/2005 | Kunzler | |
| 2005/0049623 A1 | 3/2005 | Moore et al. | |
| 2005/0049705 A1 | 3/2005 | Hale et al. | |
| 2005/0055096 A1 | 3/2005 | Serhan et al. | |
| 2005/0065518 A1 | 3/2005 | Michelson | |
| 2005/0065519 A1 | 3/2005 | Michelson | |
| 2005/0065608 A1 | 3/2005 | Michelson | |
| 2005/0065609 A1 | 3/2005 | Wardlaw | |
| 2005/0080422 A1 | 4/2005 | Otte et al. | |

(56) References Cited

U.S. PATENT DOCUMENTS

| | | |
|---|---|---|
| 2005/0085912 A1 | 4/2005 | Arnin et al. |
| 2005/0090829 A1 | 4/2005 | Martz et al. |
| 2005/0090901 A1 | 4/2005 | Studer |
| 2005/0113842 A1 | 5/2005 | Bertagnoli et al. |
| 2005/0119680 A1 | 6/2005 | Dykes |
| 2005/0124993 A1 | 6/2005 | Chappuis |
| 2005/0143818 A1 | 6/2005 | Yuan et al. |
| 2005/0149192 A1 | 7/2005 | Zucherman et al. |
| 2005/0159650 A1 | 7/2005 | Raymond et al. |
| 2005/0159746 A1 | 7/2005 | Grob et al. |
| 2005/0177240 A1 | 8/2005 | Blain |
| 2005/0182417 A1 | 8/2005 | Pagano |
| 2005/0209698 A1 | 9/2005 | Gordon et al. |
| 2005/0216018 A1 | 9/2005 | Sennett |
| 2005/0234455 A1 | 10/2005 | Binder et al. |
| 2005/0240188 A1 | 10/2005 | Chow et al. |
| 2005/0251146 A1 | 11/2005 | Martz et al. |
| 2005/0251257 A1 | 11/2005 | Mitchell et al. |
| 2005/0251260 A1 | 11/2005 | Gerber et al. |
| 2005/0267480 A1 | 12/2005 | Suddaby |
| 2006/0004367 A1 | 1/2006 | Alamin et al. |
| 2006/0004448 A1 | 1/2006 | Casey |
| 2006/0015184 A1 | 1/2006 | Winterbottom et al. |
| 2006/0036243 A1 | 2/2006 | Sasso et al. |
| 2006/0036247 A1 | 2/2006 | Michelson |
| 2006/0036323 A1 | 2/2006 | Carl et al. |
| 2006/0041311 A1 | 2/2006 | McLeer |
| 2006/0058790 A1 | 3/2006 | Carl et al. |
| 2006/0058793 A1 | 3/2006 | Michelson |
| 2006/0058878 A1 | 3/2006 | Michelson |
| 2006/0069442 A1 | 3/2006 | Michelson |
| 2006/0079905 A1 | 4/2006 | Beyar et al. |
| 2006/0079962 A1 | 4/2006 | Michelson |
| 2006/0085068 A1 | 4/2006 | Barry |
| 2006/0085074 A1 | 4/2006 | Raiszadeh |
| 2006/0095028 A1 | 5/2006 | Bleich |
| 2006/0095036 A1 | 5/2006 | Hammerslag |
| 2006/0111779 A1 | 5/2006 | Petersen |
| 2006/0111780 A1 | 5/2006 | Petersen |
| 2006/0111781 A1 | 5/2006 | Petersen |
| 2006/0142762 A1 | 6/2006 | Michelson |
| 2006/0149279 A1 | 7/2006 | Mathews |
| 2006/0149289 A1 | 7/2006 | Winslow et al. |
| 2006/0184172 A1 | 8/2006 | Michelson |
| 2006/0189991 A1 | 8/2006 | Bickley |
| 2006/0190081 A1 | 8/2006 | Kraus et al. |
| 2006/0195109 A1 | 8/2006 | McGahan et al. |
| 2006/0200137 A1 | 9/2006 | Soboleski et al. |
| 2006/0200138 A1 | 9/2006 | Michelson |
| 2006/0200139 A1 | 9/2006 | Michelson |
| 2006/0206118 A1 | 9/2006 | Kim et al. |
| 2006/0217812 A1 | 9/2006 | Lambrecht et al. |
| 2006/0229627 A1 | 10/2006 | Hunt et al. |
| 2006/0235306 A1* | 10/2006 | Cotter ............ A61B 17/1688 600/459 |
| 2006/0235391 A1 | 10/2006 | Sutterlin, III |
| 2006/0235414 A1 | 10/2006 | Lim et al. |
| 2006/0241597 A1 | 10/2006 | Mitchell et al. |
| 2006/0241626 A1 | 10/2006 | McGahan et al. |
| 2006/0241758 A1 | 10/2006 | Peterman et al. |
| 2006/0247632 A1 | 11/2006 | Winslow et al. |
| 2006/0247633 A1 | 11/2006 | Winslow et al. |
| 2006/0247650 A1 | 11/2006 | Yerby et al. |
| 2006/0259142 A1 | 11/2006 | Dooris et al. |
| 2006/0271195 A1 | 11/2006 | Thramann |
| 2006/0276790 A1 | 12/2006 | Dawson et al. |
| 2006/0276801 A1 | 12/2006 | Yerby et al. |
| 2006/0276897 A1 | 12/2006 | Winslow et al. |
| 2006/0293663 A1 | 12/2006 | Walkenhorst et al. |
| 2007/0016195 A1 | 1/2007 | Winslow et al. |
| 2007/0016196 A1 | 1/2007 | Winslow et al. |
| 2007/0016218 A1 | 1/2007 | Winslow et al. |
| 2007/0032871 A1 | 2/2007 | Michelson |
| 2007/0043362 A1 | 2/2007 | Malandain et al. |
| 2007/0050031 A1 | 3/2007 | Khosrowshahi |
| 2007/0055245 A1 | 3/2007 | Sasso et al. |
| 2007/0055263 A1 | 3/2007 | Way et al. |
| 2007/0073402 A1 | 3/2007 | Vresilovic et al. |
| 2007/0083265 A1 | 4/2007 | Malone |
| 2007/0123863 A1 | 5/2007 | Winslow et al. |
| 2007/0123888 A1 | 5/2007 | Bleich et al. |
| 2007/0135814 A1 | 6/2007 | Farris |
| 2007/0135921 A1 | 6/2007 | Park |
| 2007/0149976 A1 | 6/2007 | Hale et al. |
| 2007/0149983 A1 | 6/2007 | Link |
| 2007/0150061 A1 | 6/2007 | Trieu |
| 2007/0161991 A1 | 7/2007 | Altarac et al. |
| 2007/0162138 A1 | 7/2007 | Heinz |
| 2007/0179617 A1 | 8/2007 | Brown et al. |
| 2007/0179619 A1 | 8/2007 | Grob et al. |
| 2007/0191861 A1 | 8/2007 | Allard et al. |
| 2007/0225721 A1 | 9/2007 | Thelen et al. |
| 2007/0225812 A1 | 9/2007 | Gill |
| 2007/0244483 A9 | 10/2007 | Winslow et al. |
| 2007/0250167 A1 | 10/2007 | Bray et al. |
| 2007/0276491 A1 | 11/2007 | Ahrens et al. |
| 2007/0282441 A1 | 12/2007 | Stream et al. |
| 2007/0288014 A1 | 12/2007 | Shadduck et al. |
| 2007/0293949 A1 | 12/2007 | Salerni et al. |
| 2007/0299451 A1 | 12/2007 | Tulkis |
| 2008/0015581 A1 | 1/2008 | Eckman |
| 2008/0021457 A1 | 1/2008 | Anderson et al. |
| 2008/0021464 A1 | 1/2008 | Morin et al. |
| 2008/0058954 A1 | 3/2008 | Trieu |
| 2008/0065219 A1 | 3/2008 | Dye |
| 2008/0071375 A1 | 3/2008 | Carver et al. |
| 2008/0077245 A1 | 3/2008 | Lee |
| 2008/0091269 A1 | 4/2008 | Zipnick et al. |
| 2008/0097436 A1 | 4/2008 | Culbert et al. |
| 2008/0108996 A1 | 5/2008 | Padget et al. |
| 2008/0140207 A1 | 6/2008 | Olmos et al. |
| 2008/0154377 A1 | 6/2008 | Voellmicke |
| 2008/0161810 A1 | 7/2008 | Melkent |
| 2008/0161929 A1 | 7/2008 | McCormack et al. |
| 2008/0167657 A1 | 7/2008 | Greenhalgh |
| 2008/0177311 A1 | 7/2008 | Winslow et al. |
| 2008/0183209 A1 | 7/2008 | Robinson et al. |
| 2008/0195206 A1 | 8/2008 | Chee et al. |
| 2008/0208341 A1 | 8/2008 | McCormack et al. |
| 2008/0216846 A1 | 9/2008 | Levin |
| 2008/0234677 A1 | 9/2008 | Dahners et al. |
| 2008/0234758 A1 | 9/2008 | Fisher et al. |
| 2008/0249571 A1 | 10/2008 | Sasso et al. |
| 2008/0255564 A1 | 10/2008 | Michelson |
| 2008/0255618 A1 | 10/2008 | Fisher et al. |
| 2008/0255622 A1 | 10/2008 | Mickiewicz et al. |
| 2008/0255666 A1 | 10/2008 | Fisher et al. |
| 2008/0255667 A1 | 10/2008 | Horton |
| 2008/0275455 A1 | 11/2008 | Berry et al. |
| 2008/0287955 A1 | 11/2008 | Michelson |
| 2008/0300685 A1 | 12/2008 | Carls et al. |
| 2008/0306537 A1 | 12/2008 | Culbert |
| 2008/0312744 A1 | 12/2008 | Vresilovic et al. |
| 2009/0036927 A1 | 2/2009 | Vestgaarden |
| 2009/0131986 A1 | 5/2009 | Lee |
| 2009/0138053 A1 | 5/2009 | Assell et al. |
| 2009/0177205 A1 | 7/2009 | McCormack et al. |
| 2009/0177215 A1 | 7/2009 | Stack et al. |
| 2009/0177237 A1 | 7/2009 | Zucherman et al. |
| 2009/0182429 A1 | 7/2009 | Humphreys et al. |
| 2009/0234397 A1 | 9/2009 | Petersen |
| 2009/0248076 A1 | 10/2009 | Reynolds et al. |
| 2009/0263461 A1 | 10/2009 | McKay |
| 2009/0270929 A1 | 10/2009 | Suddaby et al. |
| 2009/0275993 A1 | 11/2009 | Phan et al. |
| 2009/0275994 A1 | 11/2009 | Phan et al. |
| 2009/0292363 A1 | 11/2009 | Goldfarb et al. |
| 2009/0297603 A1 | 12/2009 | Joshi |
| 2009/0306671 A1 | 12/2009 | McCormack et al. |
| 2009/0312763 A1 | 12/2009 | McCormack et al. |
| 2010/0016970 A1 | 1/2010 | Kapitan et al. |
| 2010/0036418 A1 | 2/2010 | Siemionow et al. |
| 2010/0069912 A1 | 3/2010 | McCormack et al. |
| 2010/0082065 A1 | 4/2010 | Butler et al. |

(56) References Cited

U.S. PATENT DOCUMENTS

| | | |
|---|---|---|
| 2010/0086185 A1 | 4/2010 | Weiss |
| 2010/0093829 A1 | 4/2010 | Gorman |
| 2010/0111829 A1 | 5/2010 | Drapeau et al. |
| 2010/0114318 A1 | 5/2010 | Gittings et al. |
| 2010/0145391 A1 | 6/2010 | Kleiner |
| 2010/0145459 A1 | 6/2010 | Mcdonough et al. |
| 2010/0161057 A1 | 6/2010 | Berry et al. |
| 2010/0191241 A1 | 7/2010 | McCormack et al. |
| 2010/0211104 A1 | 8/2010 | Moumene et al. |
| 2010/0286783 A1 | 11/2010 | Lechmann et al. |
| 2011/0004247 A1 | 1/2011 | Lechmann et al. |
| 2011/0022089 A1 | 1/2011 | Assell et al. |
| 2011/0054613 A1 | 3/2011 | Hansen |
| 2011/0077686 A1 | 3/2011 | Mishra et al. |
| 2011/0082548 A1 | 4/2011 | Assell et al. |
| 2011/0098756 A1 | 4/2011 | Brannon |
| 2011/0112644 A1 | 5/2011 | Zilberstein et al. |
| 2011/0144755 A1 | 6/2011 | Baynham et al. |
| 2011/0184470 A1 | 7/2011 | Gorek et al. |
| 2011/0190821 A1 | 8/2011 | Chin et al. |
| 2011/0245930 A1 | 10/2011 | Alley et al. |
| 2011/0295327 A1 | 12/2011 | Moskowitz et al. |
| 2011/0307061 A1 | 12/2011 | Assell et al. |
| 2012/0010659 A1 | 1/2012 | Angert et al. |
| 2012/0010662 A1 | 1/2012 | O'Neil et al. |
| 2012/0010669 A1 | 1/2012 | O'Neil et al. |
| 2012/0029545 A1 | 2/2012 | Nelson et al. |
| 2012/0065613 A1 | 3/2012 | Pepper et al. |
| 2012/0130496 A1 | 5/2012 | Duffield et al. |
| 2012/0143334 A1 | 6/2012 | Boyce et al. |
| 2012/0179259 A1 | 7/2012 | Mcdonough et al. |
| 2012/0215259 A1 | 8/2012 | Cannestra |
| 2012/0245637 A1 | 9/2012 | Kraus et al. |
| 2012/0245689 A1 | 9/2012 | Gimbel et al. |
| 2012/0265250 A1 | 10/2012 | Ali |
| 2012/0277801 A1 | 11/2012 | Marik et al. |
| 2012/0283776 A1 | 11/2012 | Mishra |
| 2012/0296431 A1 | 11/2012 | Kim et al. |
| 2012/0323242 A1 | 12/2012 | Tsuang et al. |
| 2013/0006364 A1 | 1/2013 | McCormack et al. |
| 2013/0012994 A1 | 1/2013 | McCormack et al. |
| 2013/0013070 A1 | 1/2013 | McCormack et al. |
| 2013/0018474 A1 | 1/2013 | McCormack et al. |
| 2013/0023889 A1 | 1/2013 | Blain et al. |
| 2013/0023995 A1 | 1/2013 | McCormack et al. |
| 2013/0023996 A1 | 1/2013 | McCormack et al. |
| 2013/0030440 A1 | 1/2013 | McCormack et al. |
| 2013/0030532 A1 | 1/2013 | McCormack et al. |
| 2013/0110168 A1 | 5/2013 | McCormack et al. |
| 2013/0110243 A1 | 5/2013 | Patterson et al. |
| 2013/0123922 A1 | 5/2013 | McCormack et al. |
| 2013/0123923 A1 | 5/2013 | Pavlov et al. |
| 2013/0144389 A1 | 6/2013 | Bonutti |
| 2013/0226239 A1 | 8/2013 | Altarac et al. |
| 2013/0238095 A1 | 9/2013 | Pavento et al. |
| 2013/0253649 A1 | 9/2013 | Davis |
| 2013/0274763 A1 | 10/2013 | Drapeau et al. |
| 2013/0310839 A1 | 11/2013 | McCormack et al. |
| 2013/0310878 A1 | 11/2013 | McCormack et al. |
| 2013/0310943 A1 | 11/2013 | McCormack et al. |
| 2013/0317548 A1 | 11/2013 | Malone |
| 2013/0338720 A1 | 12/2013 | Kleiner |
| 2014/0012318 A1 | 1/2014 | Goel |
| 2014/0025113 A1 | 1/2014 | McCormack et al. |
| 2014/0066758 A1 | 3/2014 | Marik et al. |
| 2014/0100657 A1 | 4/2014 | McCormack et al. |
| 2014/0114415 A1 | 4/2014 | Tyber |
| 2014/0135930 A1 | 5/2014 | Georges |
| 2014/0172103 A1 | 6/2014 | O'neil et al. |
| 2014/0228959 A1 | 8/2014 | Niemiec et al. |
| 2014/0296916 A1 | 10/2014 | Mccormack et al. |
| 2014/0379087 A1 | 12/2014 | McCormack |
| 2015/0025635 A1 | 1/2015 | Laubert |
| 2015/0088200 A1 | 3/2015 | Lins |
| 2015/0100129 A1 | 4/2015 | Waugh et al. |
| 2015/0201977 A1 | 7/2015 | Mccormack et al. |
| 2015/0230834 A1 | 8/2015 | Cannestra |
| 2015/0328005 A1 | 11/2015 | Padovani et al. |
| 2015/0328010 A1 | 11/2015 | Martynova et al. |
| 2015/0342617 A1* | 12/2015 | Kunz .................. A61C 3/02 433/215 |
| 2015/0342648 A1 | 12/2015 | Mccormack et al. |
| 2015/0342649 A1 | 12/2015 | Mccormack et al. |
| 2016/0008040 A1 | 1/2016 | Mccormack et al. |
| 2016/0242754 A1 | 8/2016 | Mccormack et al. |
| 2016/0250035 A1 | 9/2016 | De Villiers et al. |
| 2016/0317316 A1 | 11/2016 | Mccormack et al. |
| 2016/0331553 A1 | 11/2016 | Liou et al. |
| 2017/0027713 A1 | 2/2017 | Kleiner |
| 2017/0135733 A1 | 5/2017 | Donner et al. |
| 2017/0189199 A1 | 7/2017 | Maier et al. |
| 2017/0216044 A1 | 8/2017 | McCormack |
| 2017/0281360 A1 | 10/2017 | Seifert |
| 2017/0348027 A1 | 12/2017 | Mccormack et al. |
| 2017/0354444 A1 | 12/2017 | Mccormack et al. |
| 2017/0360571 A1 | 12/2017 | Mesiwala |
| 2018/0161077 A1 | 6/2018 | Mccormack et al. |
| 2018/0168772 A1* | 6/2018 | Abboud .............. A61C 8/0089 |
| 2018/0303623 A1 | 10/2018 | Shoshtaev |
| 2018/0303631 A1 | 10/2018 | Phan et al. |
| 2019/0083271 A1 | 3/2019 | Donner et al. |
| 2019/0209151 A1 | 7/2019 | Mccormack et al. |
| 2019/0239932 A1 | 8/2019 | Mccormack et al. |
| 2019/0240041 A1 | 8/2019 | Mccormack et al. |
| 2019/0247099 A1 | 8/2019 | Mccormack et al. |
| 2019/0307571 A1 | 10/2019 | Mccormack |
| 2019/0307572 A1 | 10/2019 | Mccormack et al. |
| 2019/0350626 A1 | 11/2019 | Mccormack et al. |
| 2020/0085475 A1 | 3/2020 | Mccormack et al. |
| 2020/0155205 A1 | 5/2020 | Tanaka et al. |
| 2020/0289285 A1 | 9/2020 | Siemionow et al. |
| 2020/0375633 A1 | 12/2020 | Mccormack et al. |
| 2020/0405502 A1 | 12/2020 | Gephart et al. |
| 2021/0022881 A1 | 1/2021 | Mccormack et al. |
| 2021/0059833 A1 | 3/2021 | Tanaka et al. |
| 2021/0378720 A1 | 12/2021 | Mccormack et al. |
| 2022/0031297 A1 | 2/2022 | Mccormack et al. |
| 2022/0151663 A1 | 5/2022 | Mccormack et al. |
| 2022/0211513 A1 | 7/2022 | Mccormack et al. |
| 2022/0287742 A1 | 9/2022 | Mccormack et al. |
| 2022/0313448 A1 | 10/2022 | Mccormack et al. |
| 2022/0323117 A1 | 10/2022 | Phan et al. |
| 2023/0139017 A1 | 5/2023 | McCormack et al. |
| 2023/0149179 A1 | 5/2023 | McCormack et al. |
| 2023/0181327 A1 | 6/2023 | Tanaka et al. |
| 2024/0024121 A1 | 1/2024 | Tanaka et al. |
| 2024/0032974 A1 | 2/2024 | Tanaka et al. |
| 2024/0099746 A1 | 3/2024 | McCormack et al. |
| 2024/0122629 A1 | 4/2024 | McCormack et al. |

FOREIGN PATENT DOCUMENTS

| | | |
|---|---|---|
| JP | H11508781 A | 8/1999 |
| JP | 2004523288 A | 8/2004 |
| JP | 2008509735 A | 4/2008 |
| JP | 2008522787 A | 7/2008 |
| JP | 2012501234 A | 1/2012 |
| JP | 2014516268 A | 7/2014 |
| WO | 9641582 A1 | 12/1996 |
| WO | 99/49818 A1 | 10/1999 |
| WO | 00/35388 A1 | 6/2000 |
| WO | 0053126 A1 | 9/2000 |
| WO | 01/01895 A1 | 1/2001 |
| WO | 2002/038062 A2 | 5/2002 |
| WO | 0234120 A2 | 5/2002 |
| WO | 02076335 A2 | 10/2002 |
| WO | 2005032358 A2 | 4/2005 |
| WO | 2006058221 A2 | 6/2006 |
| WO | 2006130791 A2 | 12/2006 |
| WO | 2007120903 A2 | 10/2007 |
| WO | 2008083349 A1 | 7/2008 |
| WO | 2008127978 A2 | 10/2008 |
| WO | 2008153732 A1 | 12/2008 |
| WO | 2009089367 A2 | 7/2009 |

(56) References Cited

FOREIGN PATENT DOCUMENTS

| WO | 2009148619 | A2 | 12/2009 |
|----|------------|----|---------|
| WO | 2010030994 | A2 | 3/2010 |
| WO | 2010074714 | A2 | 7/2010 |
| WO | 2010107692 | A1 | 9/2010 |
| WO | 2011050140 | A1 | 4/2011 |
| WO | 2013043584 | A2 | 3/2013 |
| WO | 2014188280 | A2 | 11/2014 |
| WO | 2016049784 | A1 | 4/2016 |
| WO | 2017066475 | A1 | 4/2017 |

OTHER PUBLICATIONS

Atul Goel, Facetal distraction as treatment for single- and multilevel cervical spondylotic radiculopathy and myelopathy: a preliminary report, J Neurosurg Spine, Jun. 2011, pp. 689-696.

Press Release, Interventional Spine, Inc., Interventional Spine, Inc. Introduces the PERPOS Fusion Facet Prep Kit, Oct. 14, 2008, 1 Page.

Press Release, minSURG Corp., Orthopedic Development Corporation's TruFUSE Procedure Tops 1,750 Patients in First Year, Sep. 24, 2007, 1 Page.

Providence Medical Technology, "Cavux Cervical Cages", first available Oct. 5, 2016. (hllps://web.archive.org/web/20161005063842/https:/providencemt.com/cavux-cervical-cages/).

Spinal News International, "FDA clears Renovis Surgical 3D-printed titanium standalone cervical cage", first available Apr. 11, 2016. https://spinalnewsinternational.com/fda-clears-renovis-surgical-3d-printed-titanium-standalone-cervical-cage/.

Providence Medical Technology, "Posterior Cervical Stabilization System (PCSS)", first available Jun. 21, 2020. (hllps://web.archive.org/web/20200621181620/hllps:/providencemt.com/pcss/).

Research Gate, "DTRAX Posterior Cervical Cage", first available Jul. 2016. (hllps://www.researchgate.net/figure/DTRAX-Posterior-Cervical-Cage-Note-The-cervical-cages-are-manufactured-from-implant_fig3_305314436).

Press Release, Interventional Spine, Inc., FDA Grants Conditional Approval to Interventional Spine's PercuDyn System IDE Application, Jul. 1, 2008, 1 Page.

Stein, et al., "Percutaneous Facet Joint Fusion: Preliminary Experience," Journal of Vascular and Interventional Radiology, Jan.-Feb. 1993, pp. 69-74, vol. 4, No. 1.

\* cited by examiner

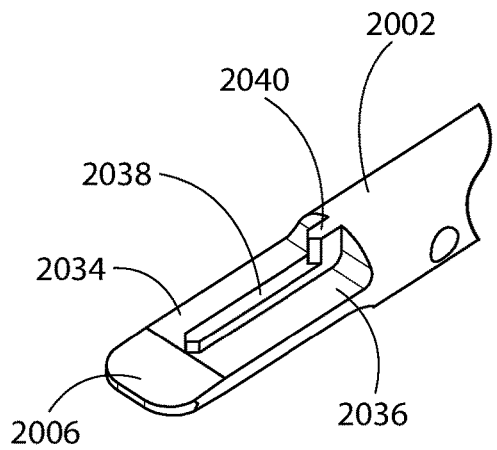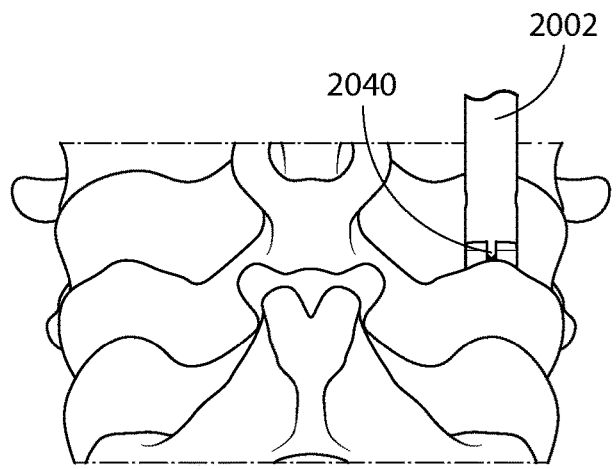
FIG. 55A          FIG. 55B
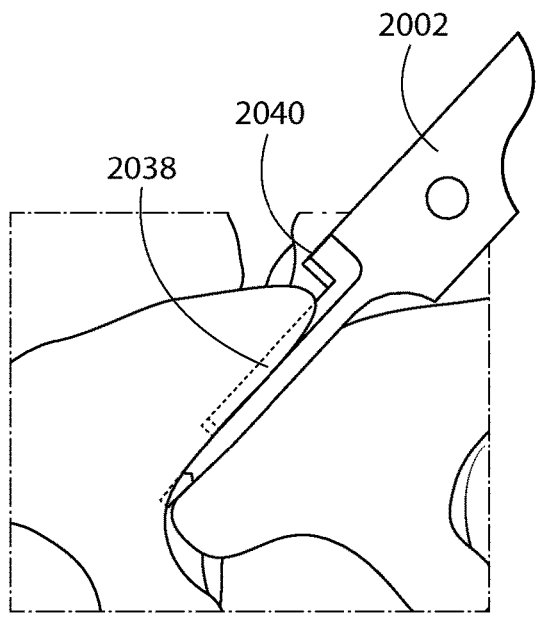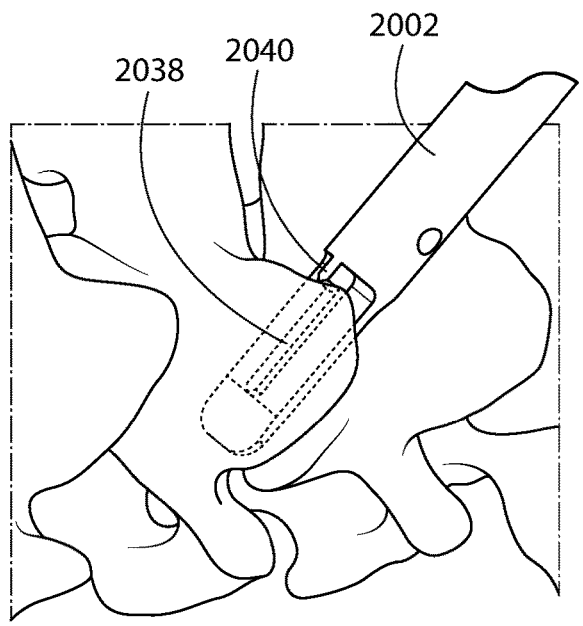
FIG. 55C          FIG. 55D

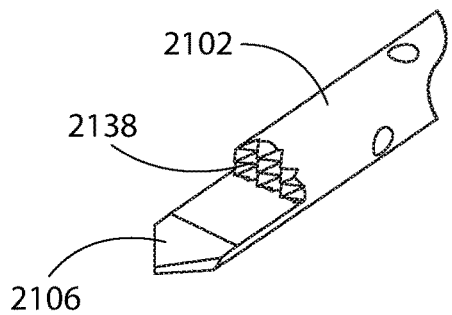
FIG. 56
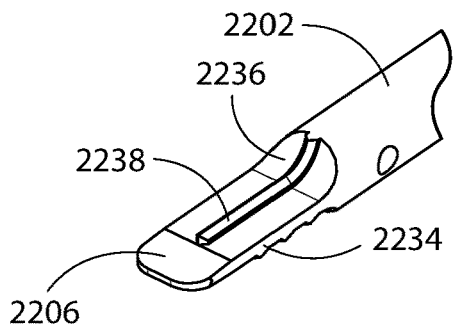 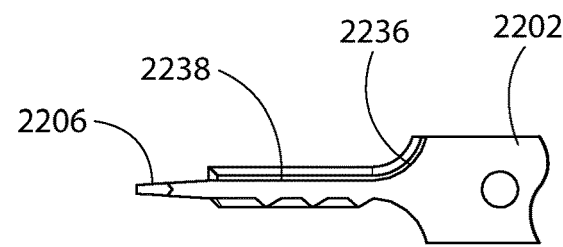
FIG. 57A  FIG. 57B
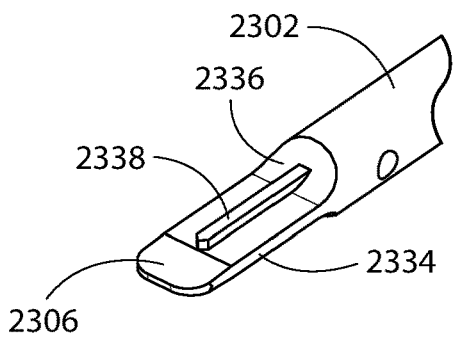 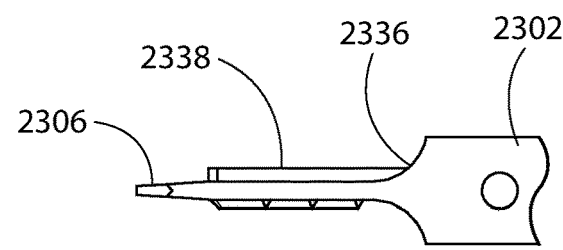
FIG. 58A  FIG. 58B
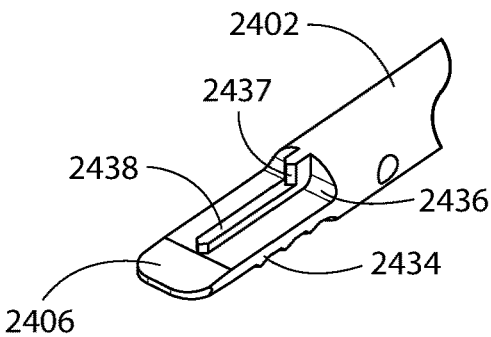 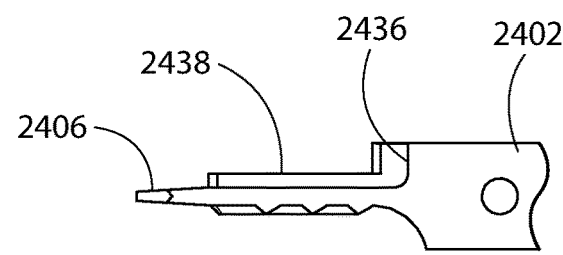
FIG. 59A  FIG. 59B

VERTEBRAL JOINT ACCESS AND DECORTICATION DEVICES AND METHODS OF USING

CROSS REFERENCE TO RELATED APPLICATIONS

The present application is a U.S. National Stage Application of International Patent Application no. PCT/US2019/052172, filed Sep. 20, 2019, which claims the benefit of priority to U.S. Application No. 62/864,103, filed Jun. 20, 2019 and titled Vertebral Joint Access and Decortication Tools and to U.S. Application No. 62/734,512, filed Sep. 21, 2018 and titled Devices and Methods for Accessing a Spinal Facet Joint and Decorticating Bone, and which are hereby incorporated by reference.

FIELD

This present disclosure relates generally to spinal distraction, and more specifically to devices and methods related to accessing a spinal facet joint and decorticating bone of a spinal facet joint.

BACKGROUND

Chronic neck and back problems cause pain and disability for a large segment of today's population. Adverse spinal conditions may be characteristic of age. Conditions such as Degenerative Disc Disease (DDD) and spinal stenosis can result in a reduction of foraminal area (i.e. the available space for the passage of nerves and blood vessels), which may compress cervical nerve roots and cause radicular pain. Both neck extension and ipsilateral rotation, in contrast to neck flexion, may further reduce the foraminal area and contribute to pain, nerve root compression, and neural injury. Spinal fusion, in which two adjacent vertebrae are fused together using plates, screws and other implants is often performed in an attempt to increase space ("spinal distraction") and/or reduce motion between the two adjacent vertebrae being operated on and to thus prevent impingement of the spinal cord or nerve roots branching from the spinal cord and passing through openings in the vertebral column. Unfortunately, most techniques and devices used for performing spinal fusion are relatively invasive and involve a number of risks and difficult recovery and rehabilitation.

One of the reasons that spinal fusion surgery is often very invasive is that, due to the position of the spinal cord in back of (posterior to) the central vertebral bodies of the spine, many of the procedures require entering the patient through the front of the body (an "anterior approach") and dissecting through various tissues to gain access to the spine. Fusion procedures are often performed on the cervical spine, which requires dissecting through the neck, or the lumbar spine, which requires dissecting through the abdomen. In either case, cutting through the anterior tissues of the patient to reach the spine is not without risk.

Therefore, it is desirable to have improved devices, systems, and methods for treating spinal stenosis. Ideally, such devices, systems, and methods would allow for minimally invasive or less invasive access and fixation, as well as helping ensure proper placement of the fixation devices. At least some of these objects will be met by the examples described herein.

BRIEF SUMMARY

The various examples described herein provide devices and methods related to decorticating bone of a spinal facet joint. In one aspect a spinal facet joint apparatus is provided. The apparatus may include a guide tube for insertion into a spinal facet joint; and a decortication tool slidably and rotatably received within the guide tube to decorticate bone of the spinal facet joint. In some aspects, one or more of the components of the apparatus may be included as part of a kit.

Optionally, the guide tube may include a cutout or scallop feature formed on a bottom or lower portion of the distal end of the guide tube. The cutout or scallop feature may be configured to further expose the decortication tool to decorticate areas outside of or adjacent to the spinal facet joint. The guide tube may include a hard stop feature adjacent a distal end. The hard stop feature may be configured to prevent a distal end of the guide tube from being inserted into the spinal canal.

Optionally, the guide tube may include a curve feature positioned proximal to the hard stop. The curve feature may be configured to provide a visualization landmark to aid in positioning the distal end of the guide tube. The guide tube may define a working cannula that includes a shape with at least one of a center hole, a concentric hole, or a four corner cutout. The working cannula may be configured to allow a variety of instruments to be used in conjunction with the guide tube. The guide tube may include forks having teeth formed on the distal end of the guide tube. A distal end of the guide tube may include a visualization hole configured to provide a visualization landmark to aid in positioning the distal end of the guide tube.

Optionally, the decortication tool may include a decorticator rasp. The decortication tool may include a decorticator burr having a first burr and a second burr, each burr including unidirectional cutting flutes. The decorticator burr may have a first burr and a second burr, each burr including bi-directional cutting flutes. The decortication tool may include an intra facet decorticator burr having a tip formed of at least one of a bullet, snub-nosed, pointed, or blunt shape. The decorticator burr may have an intra facet burr and an outer facet burr, wherein a vertical face connecting the intra facet burr and the outer facet burr is fluted.

Optionally, the decortication tool may include a decorticator burr having an intra facet burr and an outer facet burr that form a step drill. The decortication tool may include an intra facet decorticator burr comprising a tip formed as a tapered oval. The decortication tool may include an intra facet decorticator burr having a tip shaped as a prolate spheroid.

Optionally, the apparatus may include an access chisel having a distal portion and a proximal portion connected by a tubular shaft. The distal portion may have a control feature to prevent the access chisel from advancing further into the facet joint, and provide stabilization for medial/lateral movement for improved controlled and targeted decortication.

Optionally, the apparatus may include a multi-use instrument. The instrument may include a body including opposing first and second sides, and opposing first and second surfaces. The instrument may include a cavity defined in the body, the cavity being open to the second surface. The instrument may include a bar attached to the second side of the body, wherein a portion of the bar extends beyond the second surface of the body. A portion of the access chisel may be received within the cavity defined in the body of the instrument. The second surface of the body may engage the guide tube to advance the guide tube along the access chisel and into the spinal facet joint. In some aspects, one or more of the components of the apparatus may be included as part of a kit.

Optionally, the apparatus may include an outer decorticator configured to decorticate at least one of a superior and inferior vertebrae lateral mass of the spinal facet joint. The outer decorticator may include a distal end formed with a plurality of bi-directional or uni-directional teeth. In some aspects, one or more of the components of the apparatus may be included as part of a kit.

In another aspect, a vertebral facet joint access chisel apparatus is provided. The apparatus may include an access chisel configured to provide access to a target location in a vertebral facet joint. The access chisel may include a distal portion and a proximal portion connected by a tubular shaft. The distal portion may have a control feature to prevent the access chisel from advancing further into the facet joint, and provide stabilization for medial/lateral movement for improved controlled and targeted decortication.

Optionally, the control feature may include a scalloped feature or hard stop feature configured to prevent the access chisel from advancing into a spinal canal. The control feature may include a blade positioned on an upper surface of a tongue, the blade configured to provide stability and minimize unwanted medial/lateral movement. The control feature may include an anti-backout feature on an underside of a tongue. The anti-backout feature may be configured to prevent the unintentional backout of the access chisel from the facet joint. The control feature may include a notch feature at the distal tip, the notch configured to provide stability when the chisel is positioned at or near an entry point of the facet joint.

In another aspect, a decortication tool for decorticating bone is provided. The decortication tool may include a shaft with proximal and distal end portions, a handle connected to the proximal end portion of the shaft, and a decortication head coupled to the distal end portion of the shaft.

Optionally, the decortication tool may include a sheath slidably connected to the shaft. The sheath may include a plurality of cannulas defined therethrough. The shaft may be slidably received within one of the plurality of cannulas. In some examples, a cutout may be defined through the handle. The cutout may be C-shaped and radially spaced from a centerline of the shaft.

Optionally, the decortication head may include a burr. The burr may include a plurality of geometries. The burr may include a first round geometry and a second tapering geometry extending from the first round geometry. In some examples, the burr may include a single round burr.

Optionally, the decortication head may include a rasp. The decortication head may articulate relative to the shaft. The decortication head may pivot between a first position in which the decortication head is aligned with a centerline of the shaft, and a second position in which the decortication head is pivoted towards the shaft. In some examples, the decortication head may rotate relative to the shaft. The decortication head may oscillate back and forth to decorticate bone. The decortication head may rotate about an axis perpendicular to the shaft. In some examples, the rasp may define at least a portion of a terminal end surface of the decortication head.

Optionally, the decortication tool may be part of a spinal system for implanting a spinal implant within a spinal facet joint. The system may include a guide tube for insertion into a spinal facet joint. The decortication tool may be slidably and rotatably received within the guide tube to decorticate bone of the spinal facet joint. In some examples, the system may include an access chisel for insertion into a spinal facet joint. The decortication tool may include a cannula through which the access chisel is slidably received. The decortication tool may be movable along and about the access chisel to decorticate bone of the spinal facet joint. The decortication tool may be rotated about the access chisel to decorticate bone of the spinal facet joint.

In another aspect, a multi-use instrument for use in or with a spinal system is provided. The multi-use instrument may include a body including opposing first and second sides and opposing first and second surfaces. The instrument may include a cavity defined in the body. The cavity may be open to the second surface of the body. The instrument may include a bar attached to the second side of the body. A portion of the bar may extend beyond the second surface of the body.

Optionally, the cavity may be open to the first side of the body. The instrument may include a slot defined in the first side along a length of the body, the slot being in communication with the cavity. The instrument may include an alignment window defined in the first side of the body, the alignment window being in communication with the cavity.

Optionally, the instrument may include a channel defined in the first side of the body. The channel may be sized to match a profile of a fastener or knob. The channel may be shaped such that a fastener or knob is positionable in a plurality of positions along the length of the channel.

Optionally, the bar may include a convexly-shaped terminal edge. The bar may taper in width from adjacent to the body to the terminal edge.

Optionally, the instrument may be part of a spinal system for implanting a spinal implant within a spinal facet joint. The system may include an access chisel for insertion into a spinal facet joint. The system may include a guide tube slidably coupled to the access chisel. A portion of the access chisel may be received within the cavity defined in the body of the instrument. The second surface of the body may engage the guide tube to advance the guide tube along the access chisel and into the spinal facet joint. In some examples, the access chisel may include an alignment mark. The instrument may advance the guide tube along the access chisel and into the spinal facet joint until the alignment mark of the access chisel aligns with the alignment window defined in the body of the instrument.

In some aspects, a vertebral facet joint access and decortication apparatus is described. The apparatus includes an access chisel configured to provide access to a target location in a vertebral facet joint, an outer decorticator configured to decorticate at least one of a superior and inferior vertebrae lateral mass of the target location, a guide tube configured to further distract the target location, and a decorticating tool configured to decorticate an articular surface of at least one of the superior or inferior vertebrae of the target location. In some aspects, one or more of the components of the apparatus may be included as part of a kit.

In some aspects, the access chisel includes a scalloped feature or hard stop feature configured to prevent the access chisel from advancing into the spinal canal. In some aspects, the access chisel includes a blade positioned on an upper surface of a tongue, the blade configured to provide stability and minimize unwanted medial/lateral movement. In some aspects, the access chisel includes an anti-backout feature on an underside of a tongue, the anti-backout feature configured to prevent the unintentional backout of the access chisel from the facet joint. In some aspects, the access chisel includes a notch feature at the distal tip, the notch configured to provide stability when the chisel is docked to the entry of the facet joint.

In some aspects, the outer decorticator includes a distal end formed by a plurality of bi-directional or uni-directional teeth.

In some aspects, the guide tube includes a hard stop feature adjacent a distal end, the hard stop feature configured to prevent a distal end of the guide tube from being inserted into the spinal canal. In some aspects, the guide tube includes a curve feature positioned proximal to the hard stop, the curve feature configured to provide a visualization landmark to aid in positioning the distal end of the guide tube. In some aspects, the guide tube defines a working cannula that includes a shape with at least one of a center hole, a concentric hole, or a four corner cutout, the working cannula shape configured to allow a variety of instruments to be used in conjunction with the guide tube. In some aspects, the guide tube includes forks having teeth formed on the distal end of the guide tube. In some aspects, the guide tube includes a cutout or scallop feature formed on a bottom or lower portion of the distal end of the guide tube, the cutout or scallop feature configured to further expose the decorticator tool to decorticate areas outside of or adjacent the target location. In some aspects, a distal end of the guide tube includes a visualization hole configured to provide a visualization landmark to aid in positioning the distal end of the guide tube.

In some aspects, the decorticating tool comprises a decorticator rasp. In some aspects, the decorticating tool comprises a decorticator burr comprising a first burr and a second burr, each burr including unidirectional cutting flutes. In some aspects, the decorticating tool comprises a decorticator burr comprising a first burr and a second burr, each burr including bi-directional cutting flutes. In some aspects, the decorticating tool comprises an intra facet decorticator burr comprising a tip formed of at least one of a bullet, snub-nosed, pointed, or blunt shape. In some aspects, the decorticating tool comprises a decorticator burr comprising an intra facet burr and an outer facet burr, wherein a vertical face connecting the intra facet burr and the outer facet burr is fluted. In some aspects, the decorticating tool comprises a decorticator burr comprising an intra facet burr and an outer facet burr that form a step drill. In some aspects, the decorticating tool comprises an intra facet decorticator burr comprising a tip formed as a tapered oval.

In some aspects, one or more of the components of the apparatus may be included as part of a kit.

In some aspects, a decorticating tool comprising an intra facet decorticator burr comprising a tip shaped as a prolate spheroid is described.

In some aspects, a method of decorticating a facet joint is described. The steps of the method include inserting a tip of an access chisel into a target facet joint location. In some aspects, the method may include advancing an outer decorticator over the access chisel. In some aspects, the method may include decorticating superior and/or inferior lateral masses of the target location. In some aspects, the method may include removing the outer decorticator while leaving the chisel tip positioned in the target location. The method may include advancing a guide tube over the access chisel. In some aspects, the method may include positioning forks of the guide tube adjacent an outside of the chisel tip and further distracting the target location. In some aspects, the method may include removing the access chisel through a shaft of the guide tube. In some aspects, the method may include advancing a decorticator rasp through the guide tube. In some aspects, the method may include decorticating an articular surface of the target location using the decorticator rasp. In some aspects, the method may include removing the decorticator rasp through the guide tube. In some aspects, the method may include advancing a decorticator burr through the guide tube. In some aspects, the method may include further decorticating the articular surfaces of the target location using the decorticator burr. In some aspects, the method may include removing the decorticator burr through the guide tube. In some aspects, the target facet joint location is a cervical facet joint.

In some aspects, a method of accessing and decorticating a facet joint in preparation for a facet joint implant is described. Optionally, the method includes making an incision and exposing targeted bony elements at a target location in the facet joint. In some aspects, the method includes inserting an access chisel tip of an access chisel into the target location. In some aspects, the method includes slidably inserting an outer decorticator over the access chisel. In some aspects, the method includes decorticating superior and/or inferior lateral masses of the target location. In some aspects, the method optionally includes slidably removing the outer decorticator while leaving the chisel tip positioned in the target location. In some aspects, the method includes slidably inserting a guide tube over the access chisel. In some aspects, the method includes positioning forks of the guide tube adjacent an outside of the chisel tip and further distracting the target location. In some aspects, the method optionally includes slidably removing the access chisel through a shaft of the guide tube. In some aspects, the method includes slidably inserting a decorticator rasp through the guide tube. In some aspects, the method includes decorticating an articular surface of the target location using the decorticator rasp. In some aspects, the method optionally includes slidably removing the decorticator rasp through the guide tube. In some aspects, the method includes slidably inserting a decorticator burr through the guide tube. In some aspects, the method optionally includes further decorticating the articular surfaces of the target location using the decorticator burr. In some aspects, the method optionally includes slidably removing the decorticator burr through the guide tube. Optionally, the method may also include providing or applying spinal instrumentation as appropriate. In some aspects, the spinal instrumentation is a facet joint implant. In some aspects, the target location is a cervical facet joint.

Additional examples and features are set forth in part in the description that follows, and will become apparent to those skilled in the art upon examination of the specification or may be learned by the practice of the disclosed subject matter. A further understanding of the nature and advantages of the present disclosure may be realized by reference to the remaining portions of the specification and drawings, which form part of the disclosure. One of skill in the art will understand that each of the various aspects and features of the disclosure may advantageously be used separately in some instances, or in combination with other aspects and features of the disclosure in other instances.

BRIEF DESCRIPTION OF THE DRAWINGS

The accompanying drawings, which are incorporated into and constitute a part of the specification, illustrate examples of the disclosure and, together with the general description above and the detailed description below, serve to explain the principles of these examples.

FIG. 55A is a perspective view of an embodiment of an access chisel.

FIGS. 55B-55D are rear, side, and perspective views of the access chisel of FIG. 55A positioned within the facet space.

FIG. 56 is a perspective view of an embodiment of an access chisel.

FIGS. 57A and 57B are a perspective and side view of an embodiment of an access chisel.

FIGS. 58A and 58B are a perspective and side view of an embodiment of an access chisel.

FIGS. 59A and 59B are a perspective and side view of an embodiment of an access chisel.

DETAILED DESCRIPTION

Figure 1:
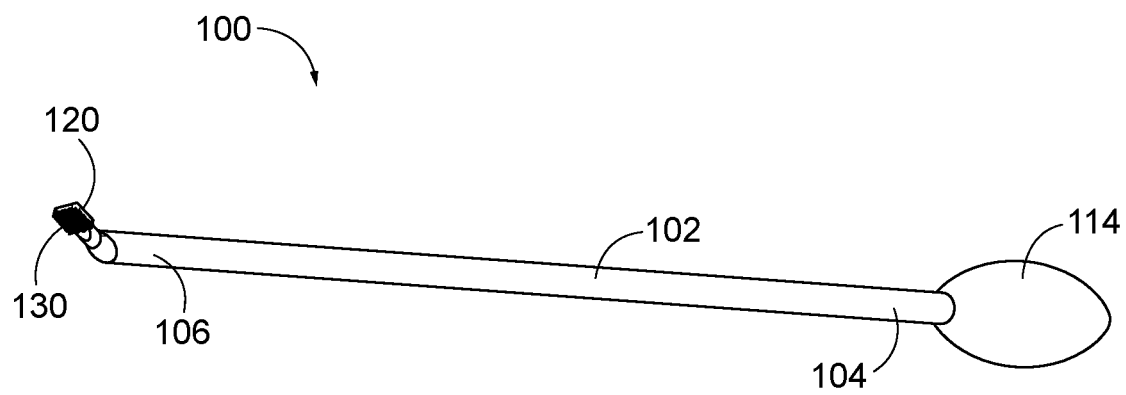
FIG. 1 is a perspective view of a decortication tool according to some examples of the present disclosure.
Figure 2:
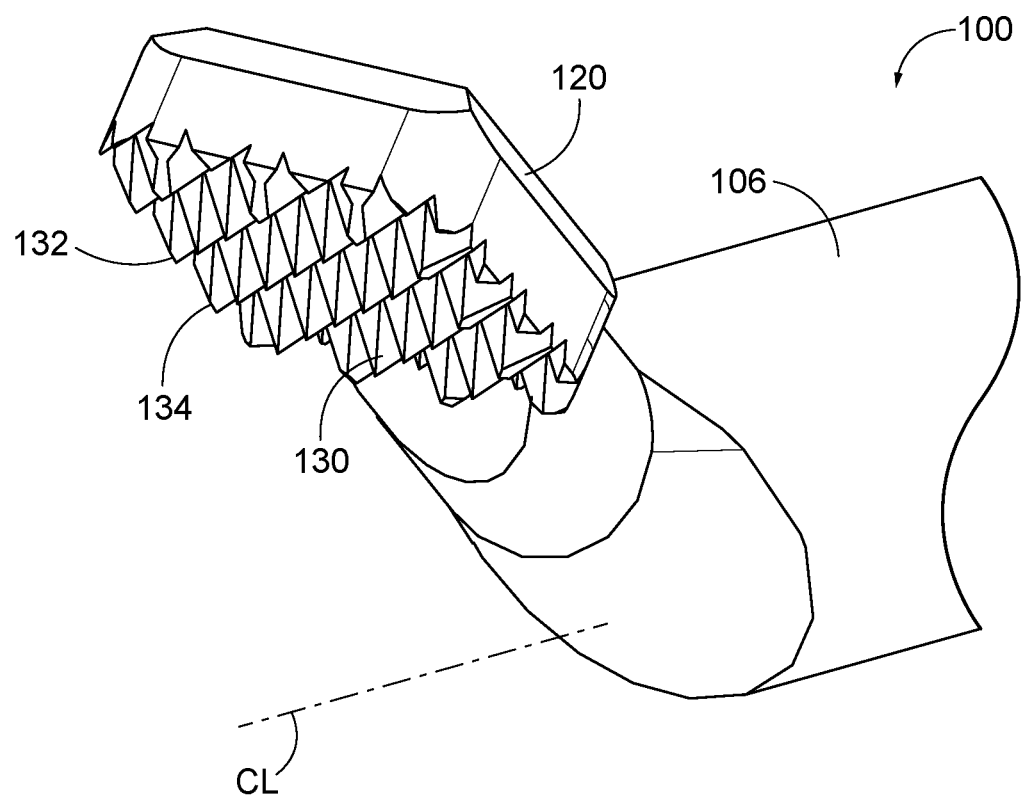
FIG. 2 is an enlarged detail view of a decortication head of the decortication tool of FIG. 1.

Aspects of the present disclosure generally involve devices and methods for treating spinal stenosis, or the narrowing of one or more areas of the intervertebral joint space between two adjacent vertebrae (i.e., a facet joint). This narrowing can put pressure on the spinal cord or the nerves that branch out from the narrowed area, thus causing pain, tingling, numbness and/or weakness.

As such, the present disclosure includes discussion of a spinal system for distracting a facet joint of the spine to remedy this condition. The system may include one or more tools and an implant for distracting and maintaining the distracted position of the facet joint. For instance, the facet joint may be distracted and prepped (e.g., decorticated) for receipt of an implant, thereby forcibly maintaining the distraction of the facet joint to relieve symptoms associated with spinal stenosis. To promote healing and bone growth around the implant, the surfaces of the facet joint to receive the implant may be decorticated prior to insertion of the implant.

Several examples of devices and systems for access and/or decortication are described. Some of the devices, systems, and methods described herein may include or be performed using one or more components of the DTRAX® Spinal System or the CORUS™ Spinal System, from Providence Medical Technology, Inc. (www.providencemt.com).

Turning to the figures, illustrative examples of the present disclosure will now be discussed in detail. FIGS. 1-6 illustrate a first example of a decortication tool 100 for decorticating bone of a spinal facet joint. Referring to FIGS. 1-6, the decortication tool 100 includes a shaft 102 with a proximal end portion 104, a distal end portion 106, and a centerline CL extending between the proximal and distal end portions 104, 106. A handle 114 is connected to the proximal end portion 104 of the shaft 102. A decortication head 120, which may be referred to as a decorticator, is coupled to the distal end portion 106 of the shaft 102. As explained below, a user may manipulate the decortication tool 100, such as via the handle 114, to decorticate bone using the decortication head 120. In other examples, the decortication tool is manipulated via the shaft. For instance, the decortication tool 100 may be positioned adjacent to or at least partially within a spinal facet joint to engage the decortication head 120 of the decortication tool 100 with bone mass or tissue of one or more adjacent vertebrae. Once the decortication head 120 engages a desired bone mass or tissue, the decortication head 120 may be moved (e.g., rotated, slid, rocked back and forth, or otherwise maneuvered) to decorticate the surface of the bone, as explained in detail below.

With continued reference to FIGS. 1-6, the decortication head 120 may include or be defined by a rasp 130. In such examples, the rasp 130 is positioned within or near the facet space, whereupon the decortication tool 100 is moved to decorticate one or more bony surfaces via the rasp 130. The rasp 130 may include many configurations. For example, the rasp 130 may include a rough surface 132 defined by a plurality of teeth or projections 134 designed to decorticate bone when moved linearly along or rotated against a bony surface.

Depending on the particular application, the decortication head 120 or rasp 130 may articulate relative to the shaft 102. For example, at least a portion of the decortication head 120 may pivot between a plurality of positions, such as between a first position (see FIG. 3) and a second position (see FIGS. 4-6). In the first position, which may be referred to as a closed position, the decortication head 120 may be aligned with the centerline CL of the shaft 102. For instance, the decortication head 120 may extend parallel to or coextensive with the centerline CL of the shaft 102 when positioned in the first position. As explained more fully below, the first position may allow the decortication tool 100 to be positioned in or adjacent to the facet space. For instance, the first position of the decortication head 120 may allow the decortication tool 100 to be guided to the facet space using a guide apparatus (e.g., a guide tube or access chisel).

In the second position, which may be referred to as an open position, the decortication head 120 may be pivoted towards the shaft 102. For example, the decortication head 120 may pivot upwards from the first position and towards the second position. In such examples, the decortication head 120 may pivot downwards from the second position and towards the first position. As detailed below, the second position may allow the decortication tool 100 to decorticate bone surfaces within the facet space. For example, once guided to the facet space, the decortication head 120 may be articulated to the second position such that the decortication head 120 may decorticate bone by movement of the decortication head 120. In particular, the decortication head 120 may be rotated medial and lateral (FIG. 5) or moved back and forth (FIG. 6) to decorticate bone.

The decortication head 120 may be articulated between positions in many manners. In one example, the decortication head 120 may be articulated by placing downward pressure on the shaft 102, which may be pliable. Additionally or alternatively, the decortication head 120 may be articulated by mechanical features incorporated into the design of the decortication tool 100. For instance, the decortication tool 100 may include one or more gear trains, lever systems, or the like, such as within the shaft 102, to cause the decortication head 120 to move between positions. In such examples, the handle 114 may be manipulated, such as pushed, pulled, or rotated, among others, to move the decortication head 120 between the first and second positions. Such examples are illustrative only, and the decortication head 120 may be articulated between positions in many configurations.

Figure 7:
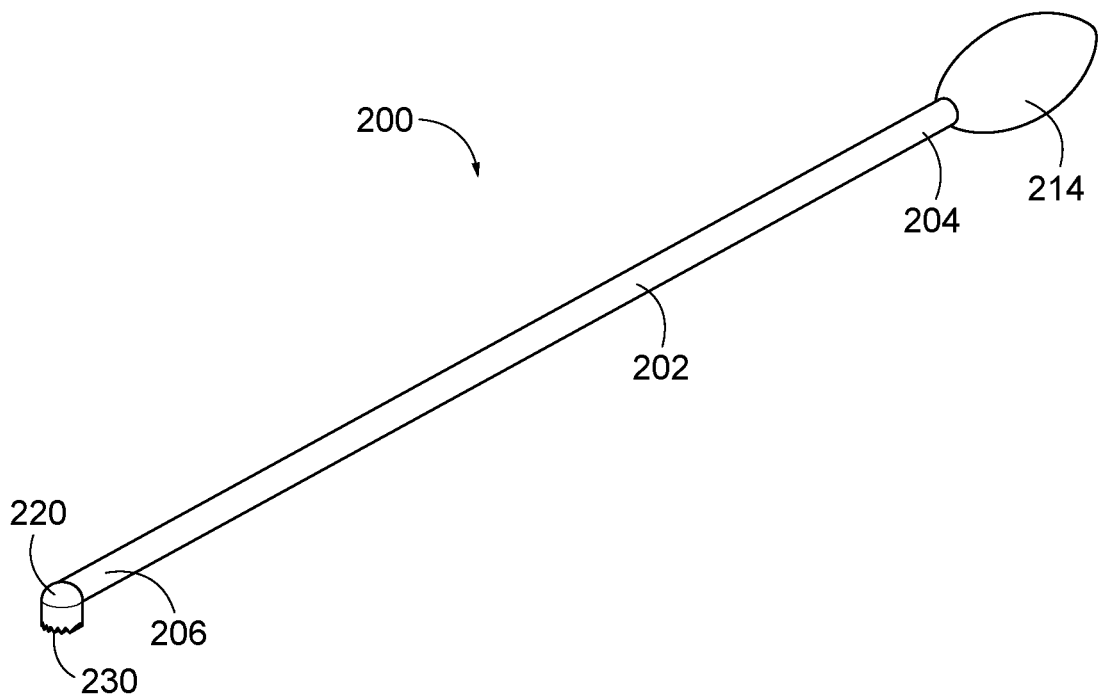
FIG. 7 is a perspective view of an additional decortication tool according to some examples of the present disclosure.
Figure 8:
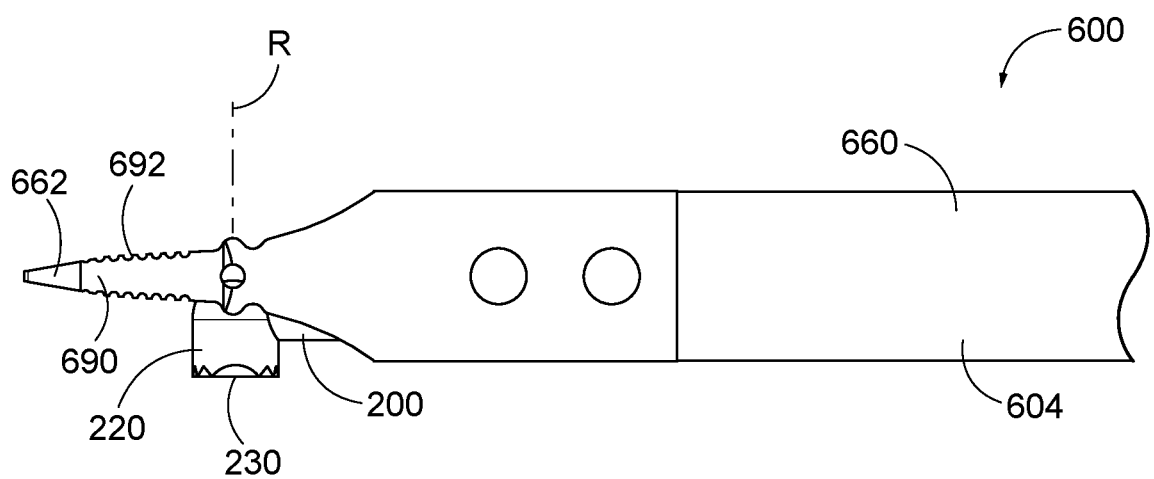
FIG. 8 is an enlarged, fragmentary elevation view of the decortication tool of FIG. 7.
Figure 9:
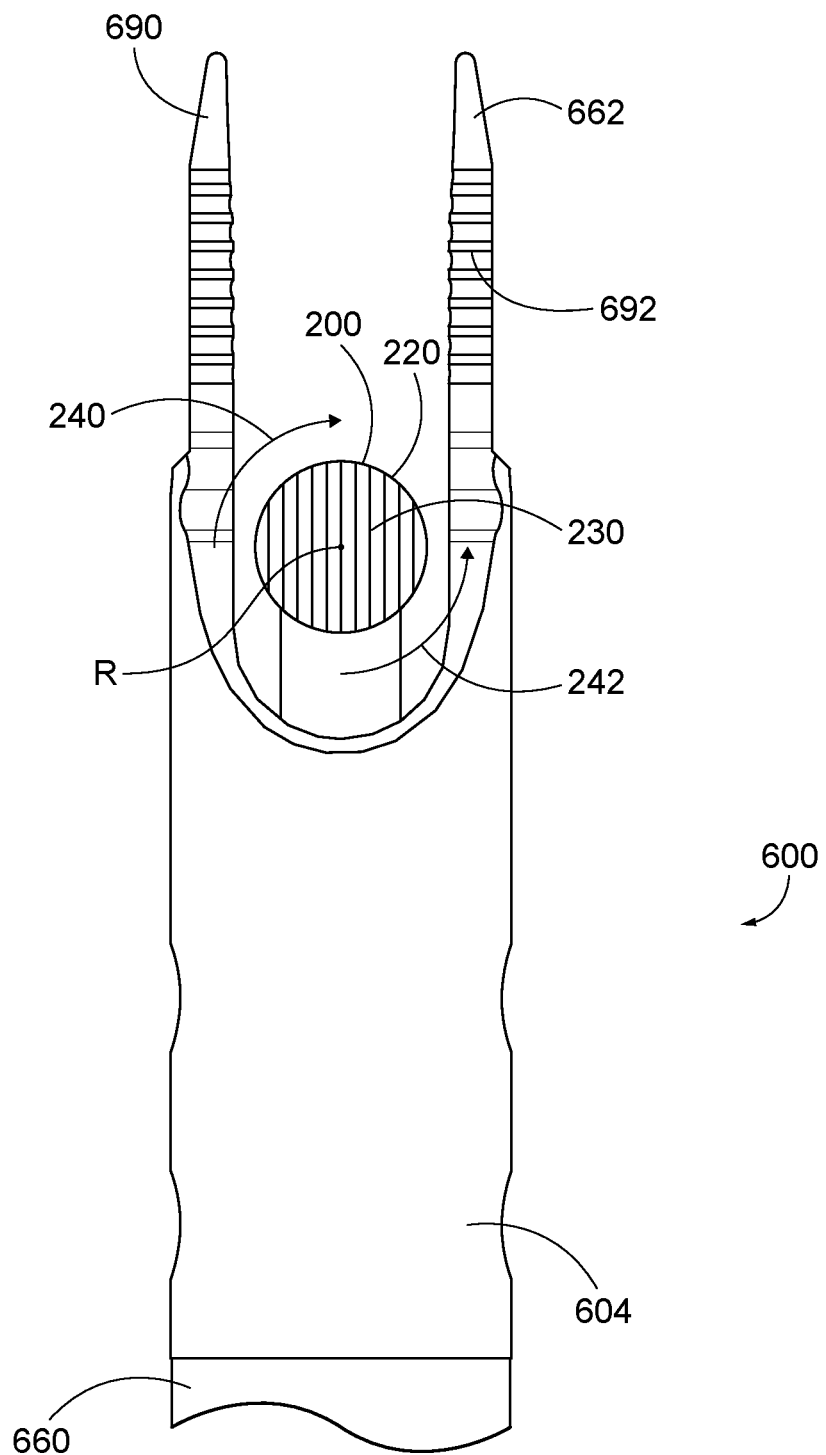
FIG. 9 is an enlarged, fragmentary plan view of the decortication tool of FIG. 7.
Figure 10:
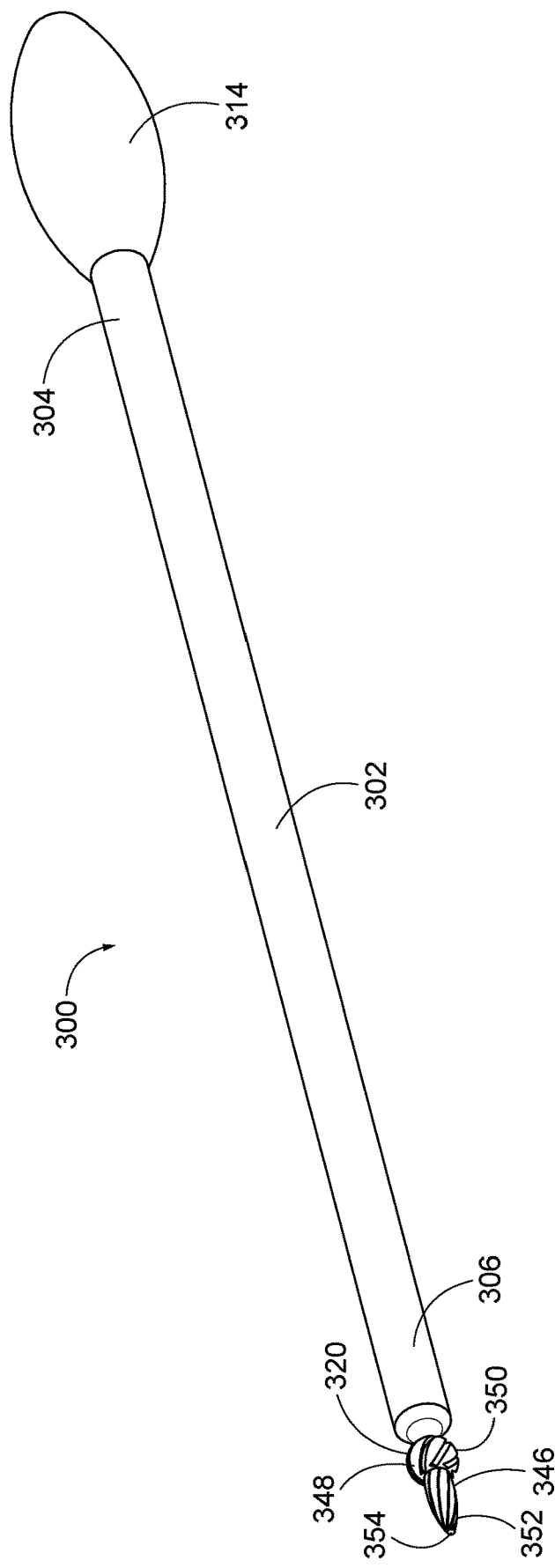
FIG. 10 is a perspective view of an additional decortication tool according to some examples of the present disclosure.

FIGS. 7-9 illustrate an additional decortication tool 200 for decorticating bone of a spinal facet joint. Except as otherwise noted below, the decortication tool 200 is similar to the decortication tool 100 of FIGS. 1-6 described above. Thus, like features may not be described when they would be apparent to those of skill in the art in light of the description above and in view of FIGS. 7-9. For ease of reference, like features include appropriately incremented reference numbers.

Referring to FIGS. 7-9, the decortication tool 200 includes a shaft 202, a handle 214 connected to a proximal end portion 204 of the shaft 202, and a decortication head 220 coupled to a distal end portion 206 of the shaft 202. As shown, the decortication head 220 includes or is defined by a rasp 230. The rasp 230 may be configured similar to or different from the rasp 130 described above. The decortication head 220 or rasp 230 may rotate relative to the shaft 202. Depending on the particular application, the decortication head 220 may rotate in one direction or in two directions. For instance, the decortication head 220 may rotate in only a first direction 240 (e.g., a clockwise rotation), in only a second direction 242 (e.g., a counter-clockwise rotation), or in both the first and second directions 240, 242. In one example, the decortication head 220 may oscillate back and forth in the first and second directions 240, 242 to decorticate bone.

As shown in FIGS. 8 and 9, the decortication head 220 may rotate about a rotational axis R. The rotational axis R may extend in many angles relative to the shaft 202. For instance, the rotational axis R may extend substantially perpendicular to the shaft 202. As described herein, perpendicular may include angles between about 80 degrees and about 100 degrees relative to the centerline CL of the shaft 202. The decortication head 220 may be fixed relative to the shaft 202. In some examples, the decortication head 220 may be pivoted to a desired angle relative to the shaft 202. For instance, the decortication head 220 may be pivoted such that the rotational axis R extends between about 0 degrees and about 180 degrees relative to the centerline CL of the shaft 202.

The decortication head 220 may be rotated relative to the shaft 202 in many manners. In one example, the decortication tool 200 may include mechanical features incorporated into its design, such as one or more gear trains, lever systems, or the like. In such examples, the mechanical features may couple the handle 214 to the decortication head 220 such that manipulation of the handle 214 causes the decortication head 220 to rotate. In particular, the handle 214 may be rotated, pushed, pulled, twisted, or the like to cause the decortication head 220 to rotate. Such examples are illustrative only, and the decortication head 220 may be rotated relative to the shaft 202 in many configurations.

FIGS. 10-13 illustrate an additional decortication tool 300 for decorticating bone of a spinal facet joint. Except as otherwise noted below, the decortication tool 300 is similar to the decortication tools 100 and 200 of FIGS. 1-9 described above. Thus, like features may not be described when they would be apparent to those of skill in the art in light of the description above and in view of FIGS. 10-13. For ease of reference, like features include appropriately incremented reference numbers.

Referring to FIGS. 10-13, the decortication tool 300 includes a shaft 302, a handle 314 connected to a proximal end portion 304 of the shaft 302, and a decortication head 320 coupled to a distal end portion 306 of the shaft 302. As shown, the decortication head 320 includes or is defined by a burr 346. In such examples, the burr 346 is positioned within or near the facet space, whereupon the decortication tool 300 is rotated to decorticate one or more bony surfaces via the burr 346. The burr 346 may include many configurations. For instance, the burr 346 may be defined by one or more cutting edges 348 designed to decorticate bone when the burr 346 is rotated against or moved linearly along a bony surface.

Figure 12:
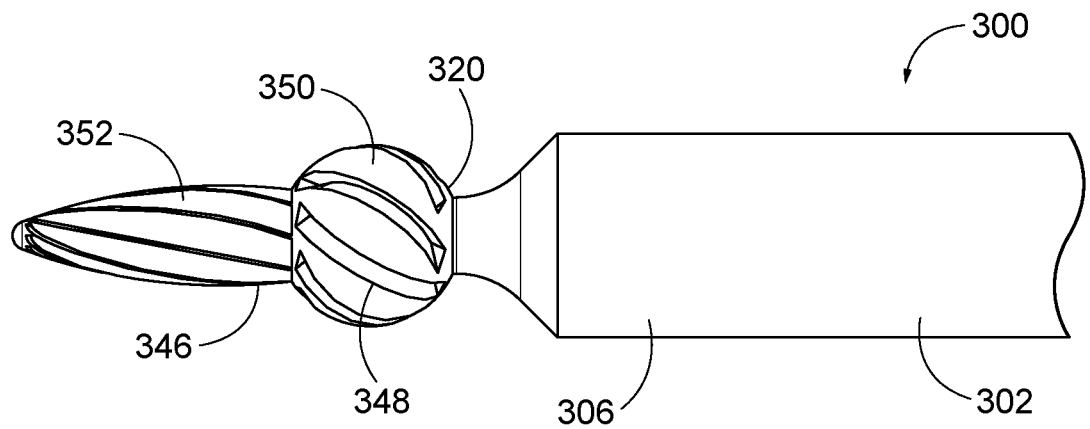
FIG. 12 is an enlarged, fragmentary elevation view of the decortication tool of FIG. 10.
Figure 13:
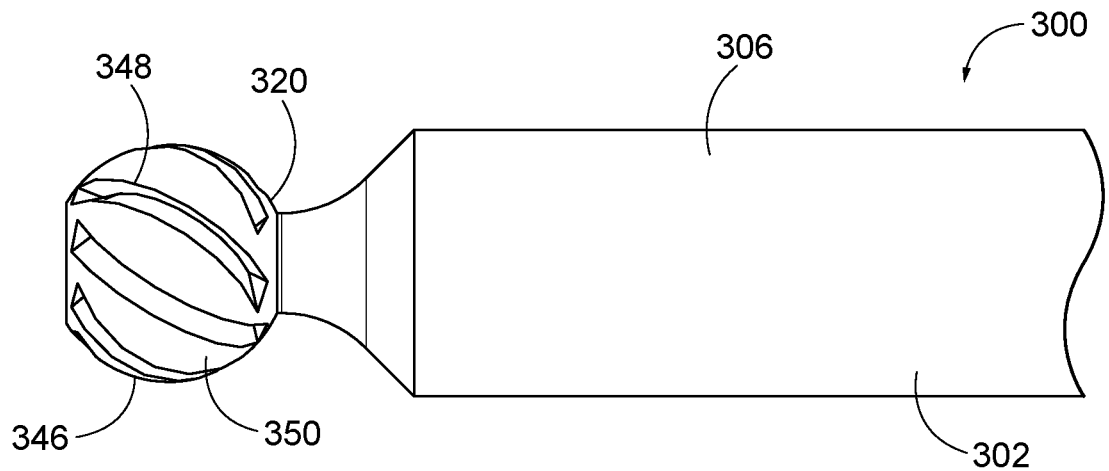
FIG. 13 is another enlarged, fragmentary elevation view of the decortication tool of FIG. 10.

The burr 346 may include many configurations. For instance, as shown in FIG. 12, the burr 346 may include a complex shape with a plurality of geometries. As one example, the burr 346 may include a first geometry or burr 350 and a second geometry or burr 352 extending from the first geometry 350. Depending on the particular application, the first geometry 350 may be substantially round in two-dimensional space, or substantially spherical in three-dimensional space. The second geometry 352 may be different than the first geometry 350. In one example, the second geometry 352 includes a tapering geometry extending from the first geometry 350 to a point-like tip 354. For instance, the second geometry 352 may include a shape similar to a missile or bullet shape. In such examples, the second geometry 352 may be sized and shaped to position a portion of the burr 346 into the facet joint to decorticate one or more bony surfaces inside the facet space. The first geometry 350 may be designed such that a portion of the burr 346 sits outside the facet joint to decorticate one or more bony surfaces outside the facet space. In this manner, the burr 346 may be arranged to decorticate bony surfaces both inside and outside the facet space in a simultaneous manner.

FIGS. 14-24 illustrate an additional decortication tool 400 for decorticating bone of a spinal facet joint. Except as otherwise noted below, the decortication tool 400 is similar to the decortication tools 100, 200, and 300 of FIGS. 1-13 described above. Thus, like features may not be described when they would be apparent to those of skill in the art in light of the description above and in view of FIGS. 14-24. For ease of reference, like features include appropriately incremented reference numbers.

Figure 14:
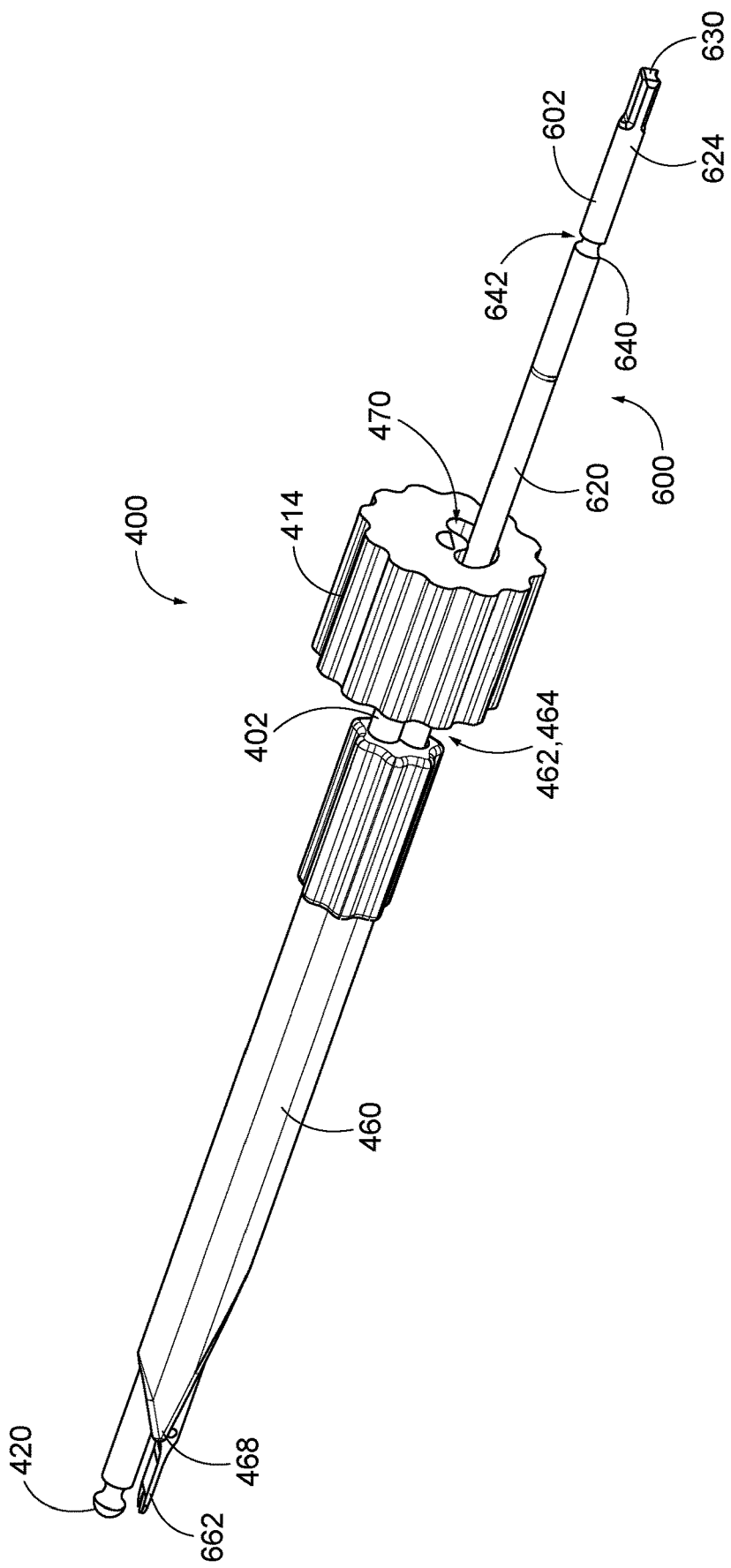
FIG. 14 is a perspective view of an additional decortication tool according to some examples of the present disclosure.
Figure 15:
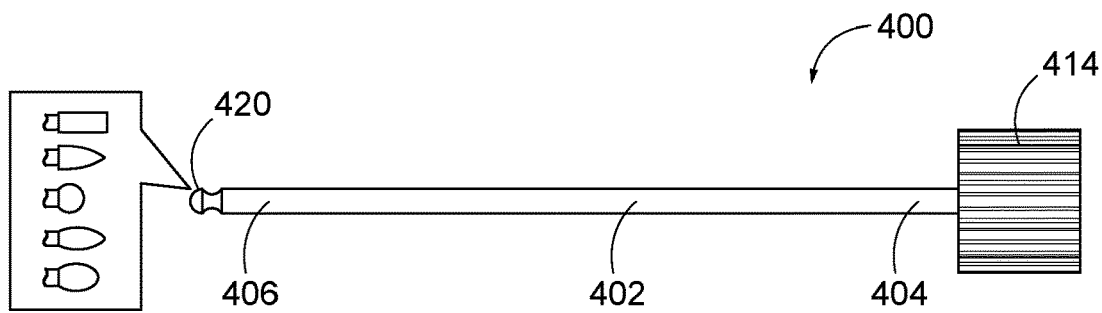
FIG. 15 is an elevation view of the decortication tool of FIG. 14.
Figures 17, 18:
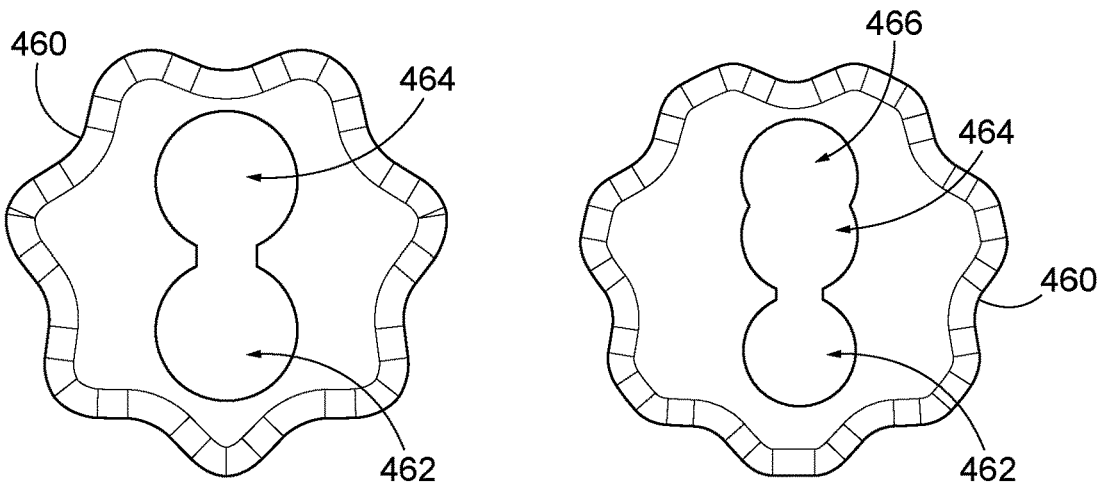
FIG. 17 is an elevation view of a sheath of the decortication tool of FIG. 14 according to some examples of the present disclosure.
FIG. 18 is an elevation view of an additional sheath of the decortication tool of FIG. 14 according to some examples of the present disclosure.
Figure 19:
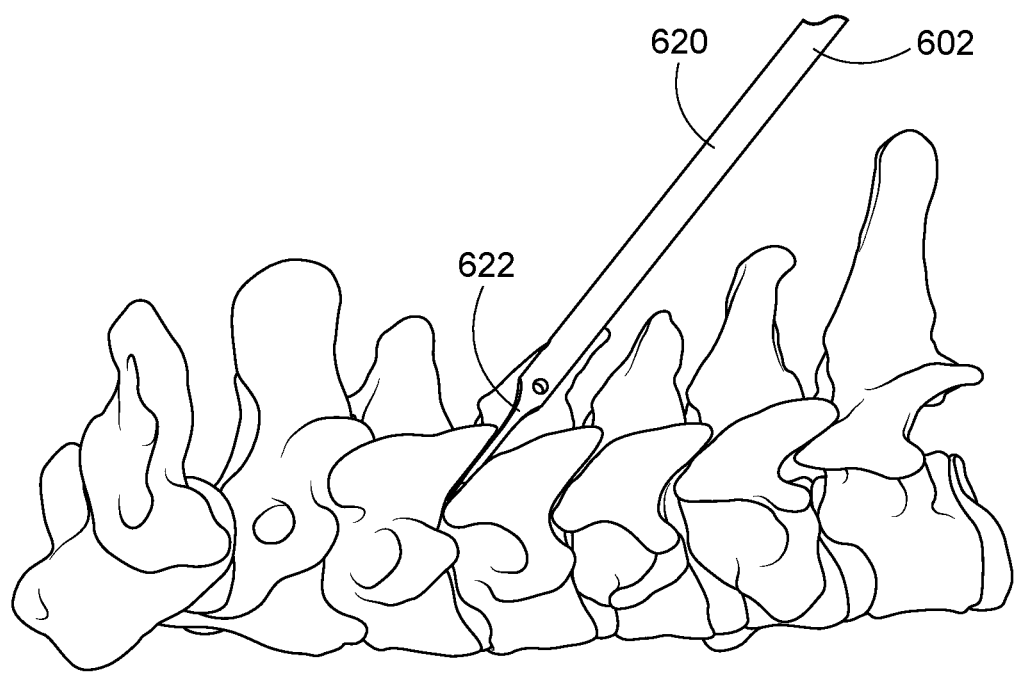
FIG. 19 is an elevation view of an access chisel anchored in a spinal facet joint according to some examples of the present disclosure.

Referring to FIGS. 14 and 15, the decortication tool 400 includes a shaft 402, a handle 414 connected to a proximal end portion 404 of the shaft 402, and a decortication head 420 coupled to a distal end portion 406 of the shaft 402. The decortication tool 400 may include a sheath 460 through which the shaft 402 is slidably received. As shown in FIGS. 17 and 18, the sheath 460 may include a plurality of cannulas defined therethrough. For instance, the sheath 460 may include a first cannula 462 and a second cannula 464 above the first cannula 462. In some examples, the sheath 460 may include additional cannulas, such as a third cannula 466 above the second cannula 464. In such examples, the shaft 402 may be slidably received within one of the cannulas. In particular, as explained below, the shaft 402 may be slidably received within the second cannula 464, or the third cannula 466 (if equipped). In some examples, the sheath 460 may include a tip 468.

Figure 16:
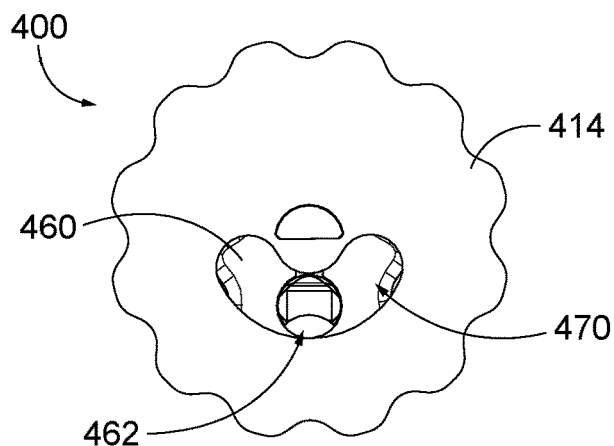
FIG. 16 is another elevation view of the decortication tool of FIG. 14.

With reference to FIG. 16, the handle 414 may include a cutout 470 defined therethrough. As shown, the cutout 470 may be C-shaped and radially spaced from the centerline CL of the shaft 402. In this manner, the handle 414 may accommodate another tool associated with the sheath 460. For instance, as detailed more fully below, a guide element or fixation device, such as an access chisel or the like, may be inserted within the first cannula 462 of the shaft 402. In such examples, the shaft 402 may be inserted within the second cannula 464 of the sheath 460. To accommodate a portion of the guide element extending beyond the sheath 460, the guide element may be received within the cutout 470 of the handle 414 as the decortication head 420 is moved towards the facet joint. In addition, the cutout 470 may allow user manipulation of the handle 414 to move the decortication head 420 without interfering with or dislodging the guide element or fixation device. For instance, the shape of the cutout 470 may allow rotation of the handle 414 (and decortication head 420) without moving the guide element or fixation device. If additional reach is needed to decorticate bone, the shaft 402 may be inserted within the third cannula 466. Additional cannulas may be incorporated into the sheath 460 if additional reach for the decortication head 420 is needed.

FIGS. 25-29 illustrate an additional decortication tool 500 for decorticating bone of a spinal facet joint. Except as otherwise noted below, the decortication tool 500 is similar to the decortication tools 100, 200, 300, and 400 of FIGS. 1-24 described above. Thus, like features may not be described when they would be apparent to those of skill in the art in light of the description above and in view of FIGS. 25-29. For ease of reference, like features include appropriately incremented reference numbers.

Figure 25:
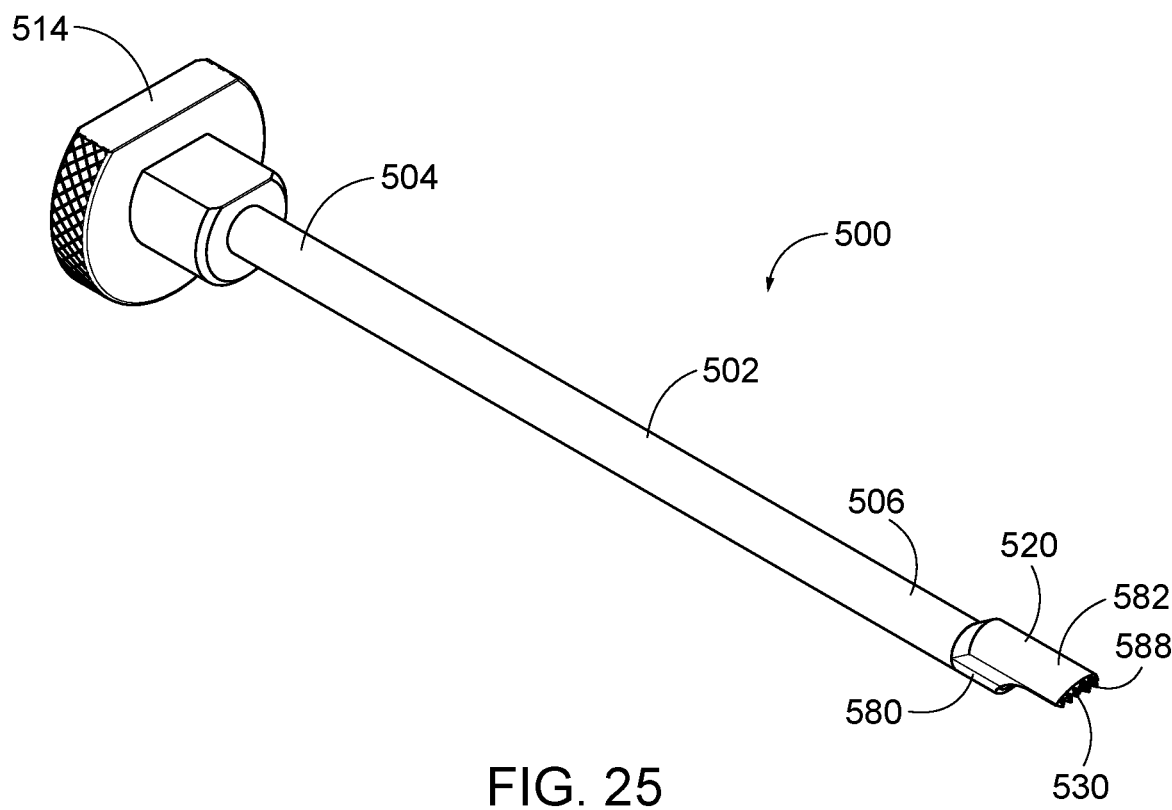
FIG. 25 is a perspective view of an additional decortication tool according to some examples of the present disclosure.
Figure 26:
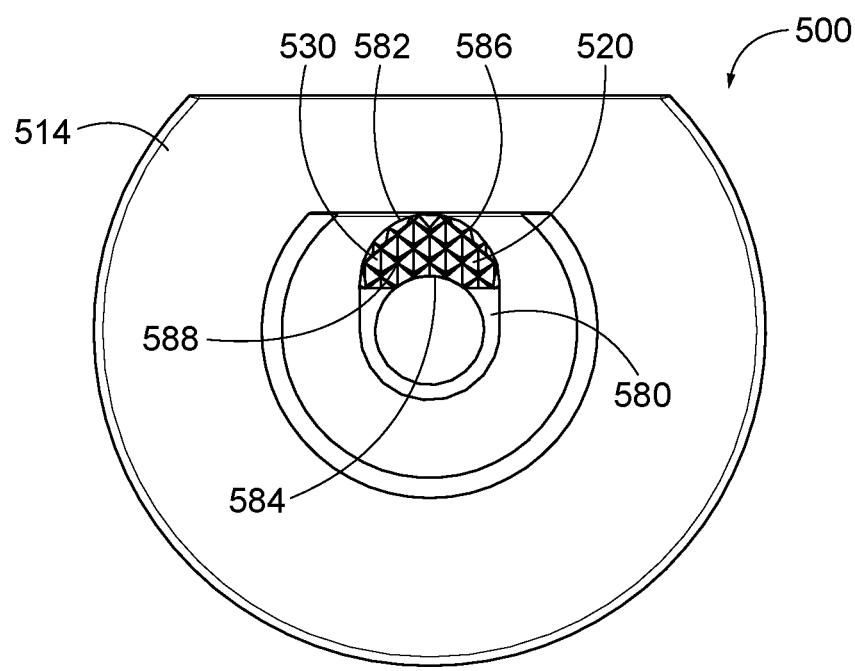
FIG. 26 is an elevation view of the decortication tool of FIG. 25.

Referring to FIGS. 25 and 26, the decortication tool 500 includes a shaft 502, a handle 514 connected to a proximal end portion 504 of the shaft 502, and a decortication head 520 coupled to a distal end portion 506 of the shaft 502. The shaft 502 may be hollow defining a bore 576 extending through the handle 514, shaft 502, and decortication head 520.

As shown, the decortication head 520 may be formed integrally with or fixed to the distal end portion 506 of the shaft 502. The decortication head 520 may include first and second portions 580, 582. The first portion 580 may be connected to the distal end portion 506 of the shaft 502. The second portion 582 may extend from the first portion 580 and parallel to the centerline CL of the shaft 502. In one example, the second portion 582 is radially spaced from the centerline CL of the shaft 502. For example, the second portion 582 may include a substantially C-shaped profile with inner and outer surfaces 584, 586 defining respective arc segments or lengths spaced radially from the centerline CL of the shaft 502. The arc lengths of the inner and outer surfaces 584, 586 may be less than a full circumference around the centerline CL of the shaft 502, less than one-half the circumference around the centerline CL of the shaft 502, or less than one-quarter the circumference around the centerline CL of the shaft 502. In this manner, the second portion 582 may not extend completely around the centerline CL of the shaft 502.

Depending on the particular application, the decortication head 520 may include or be defined as a rasp 530. For example, the rasp 530 may define at least a portion of a terminal end surface 588 of the second portion 582 of the decortication head 520. In such examples, the second portion 582 of the decortication head 520 is positioned within or near the facet space, whereupon the decortication tool 500 is rotated to decorticate one or more bony surfaces via the rasp 530.

System—General

Figure 94:
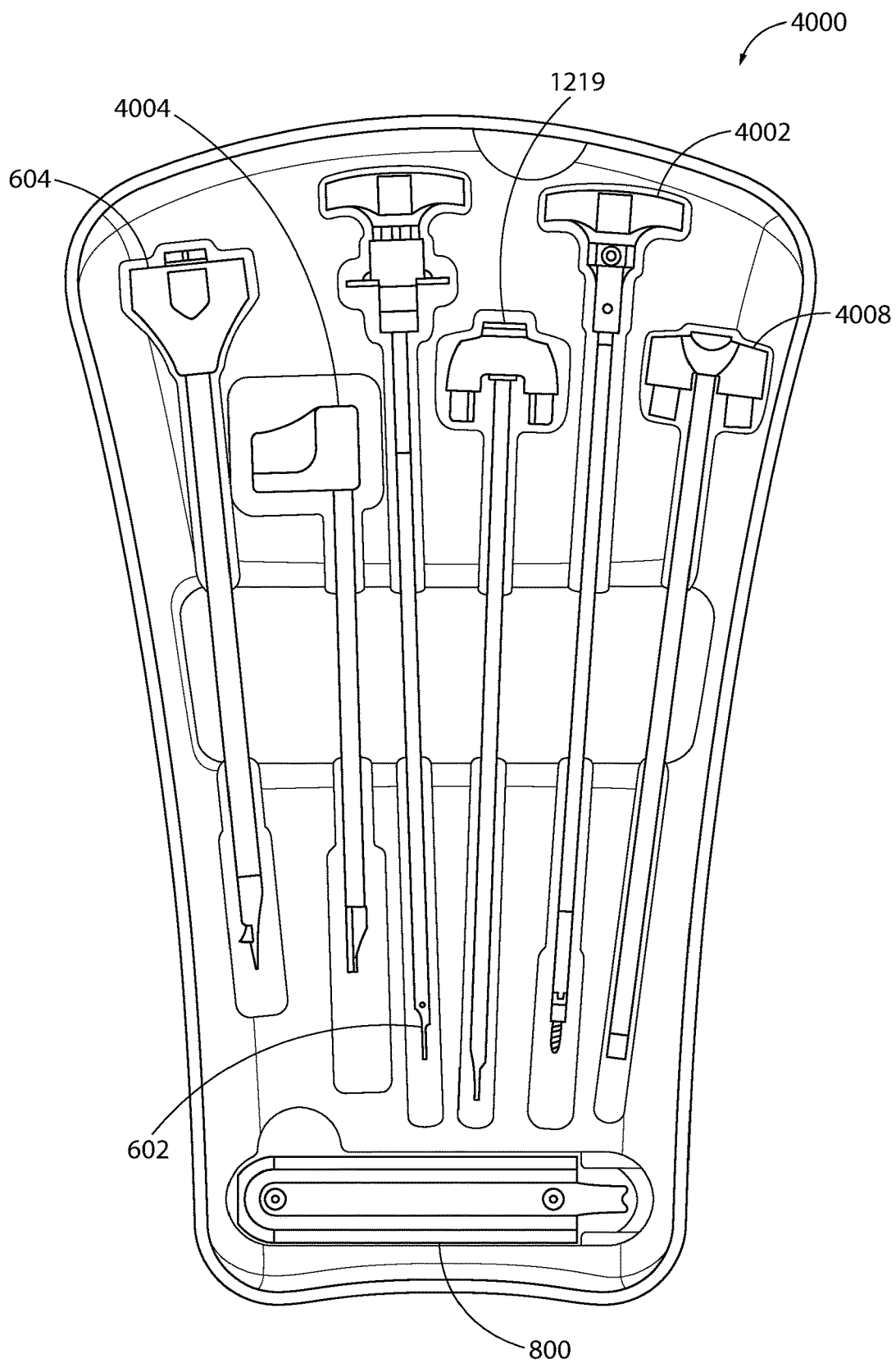
FIG. 94 illustrates a spinal instrumentation kit, which may include various tools or devices disclosed herein.

Referring to FIGS. 1-29, the decortication tools 100, 200, 300, 400, 500 may be utilized as part of a spinal system 600 and provided in a spinal system kit 4000 as shown in FIG. 94. The spinal system 600 may include any combination of the following elements: an access chisel 602, a guide tube 604, and one or more of the decortication tools 100, 200, 300, 400, or 500 described above. In such examples, the components of the spinal system 600 may allow a user (e.g., surgeon) to decorticate bone of a spinal facet joint in preparation for a spinal implant. In some examples, the spinal system 600 may include additional components for implanting the spinal implant within the facet space of a spinal facet joint. For example, the spinal system 600 may include a delivery device 610, a driver assembly, a malleting tool, or other instruments, as explained more fully below.

In some examples, the spinal system 600 may be included in a kit 4000, as shown in FIG. 94. In some examples, the kit includes some or all of an access chisel 602, a guide tube 604, a decortication tool 4002, 4004 which may be similar to the decortication tools 100, 200, 300, 400, or 500 described above, a rasp 1219 as described in FIG. 72, a tamp 4008 to tamp bone graft material, and a multi-use instrument 800 as described in FIGS. 30 and 31. In some examples, the kit 4000 may also include some or all of a delivery device 610 and/or a driver assembly to deliver/drive a spinal implant, a malleting tool (in addition to or instead of the multi-use tool), or other instruments.

With reference to FIGS. 19, 21, 27, 28, and 33, the access chisel 602 will be discussed in detail. The access chisel 602 can include many configurations allowing at least partial insertion of the access chisel 602 into a spinal facet joint. For example, the access chisel 602 may include a shaft portion 620, a tip portion 622, and a head portion 624. The shaft portion 620 may have a generally cylindrical cross-section, such as tubular or otherwise. The tip portion 622 may by chamfered such that the access chisel 602 may be driven into and/or otherwise anchored in the spinal facet joint. Depending on the application, the tip portion 622 may have one or more chamfers, such as a single chamfer, a double chamfer, or more than two chamfers. In some examples, the tip portion 622 may be coped to define a tip or point. The head portion 624 may be arranged to facilitate user manipulation of the access chisel 602. For instance, the head portion 624 may be generally solid with an end surface 630 for malleting the access chisel 602 into position. In some examples, the head portion 624 may include an alignment mark 640. For example, a groove 642 may be defined on the head portion 624 at a distance away from the end surface 630. The groove 642 may extend circumferentially around the head portion 624. As explained below, the alignment mark 640 (groove 642) may align with a corresponding alignment feature of another tool or instrument to define a seated position of the access chisel 602 and/or the other tool or instrument.

Referring now to FIGS. 3-6, 11, and 34, the guide tube 604 will be discussed in more detail. Like the access chisel 602, the guide tube 604 can include many configurations allowing at least partial insertion of the guide tube 604 into a spinal facet joint. In one example, the guide tube 604 includes a tubular shaft 660, an anchoring mechanism 662 at a distal end 664 of the tubular shaft 660, and a handle 668 at a proximal end 670 of the tubular shaft 660. The tubular shaft 660 may have an annularly-shaped cross section with an inner radius defining an internal bore 680. The inner radius may allow insertion of other spinal instruments and tools within the guide tube 604. For instance, the internal bore 680 may be sized and shaped to allow insertion of the access chisel 602 therein. In such examples, the guide tube 604 may be movably and/or slidably coupled to the access chisel 602. For instance, the guide tube 604 may slide along and/or rotate about the shaft portion 620 of the access chisel 602.

Figure 11:
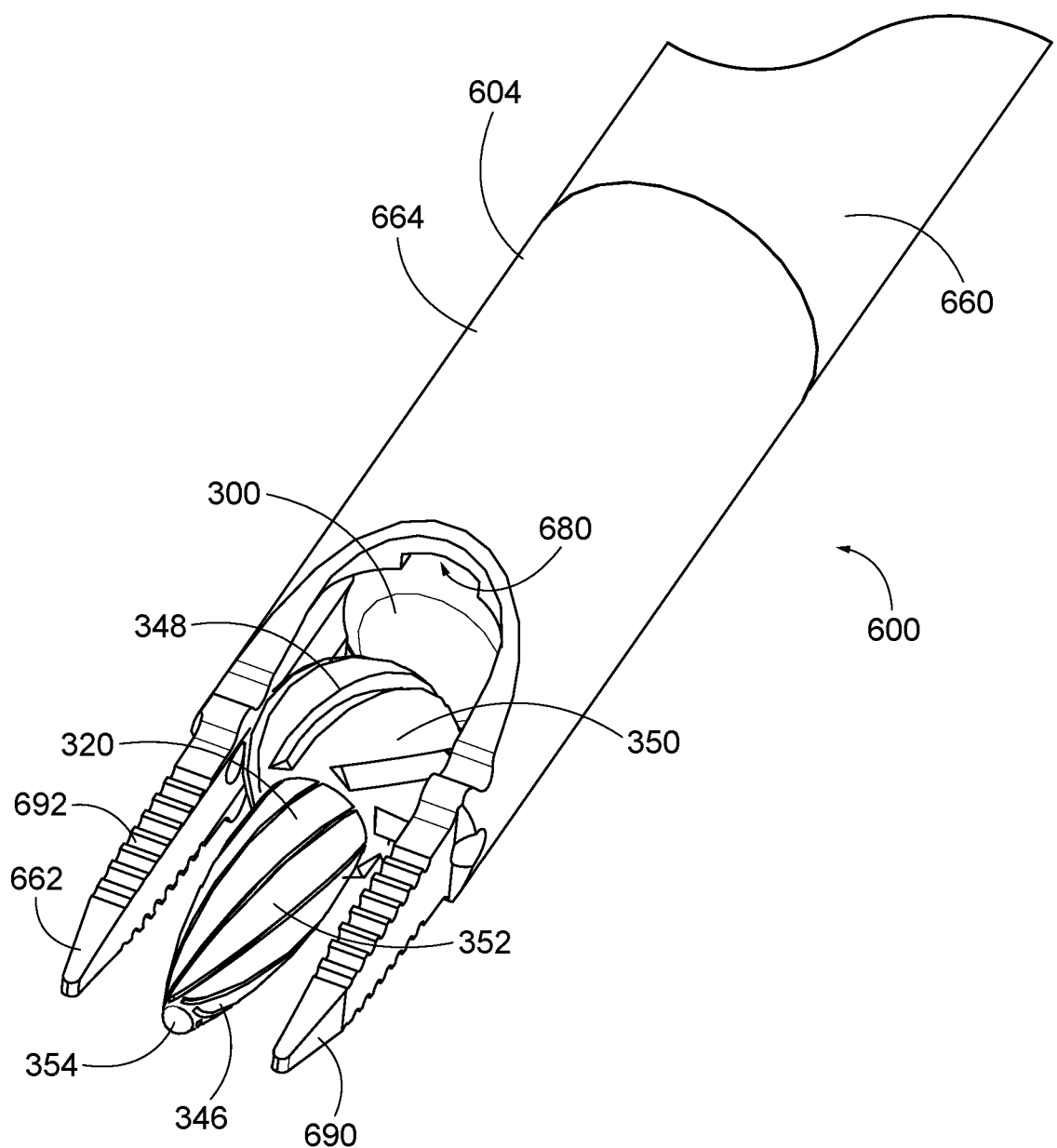
FIG. 11 is an enlarged, fragmentary view of the decortication tool of FIG. 10.

The anchoring mechanism 662 of the guide tube 604 allows the guide tube 604 to be driven into and/or otherwise anchored in a spinal facet joint. For instance, the anchoring mechanism 662 may include one or more anchoring forks 690 arranged to fix the guide tube 604 in a desired position within the spinal facet joint. As shown in FIG. 11, the anchoring forks 690 may be arranged such that the decortication head 320 is positioned and moves between two or more forks 690. The forks 690 may have a general V-shape to facilitate insertion and/or anchoring of the forks 690 within the spinal facet joint. In some examples, the forks 690 may include a plurality of serrations 692 to facilitate anchoring of the guide tube 604 within the spinal facet joint.

Figure 3:
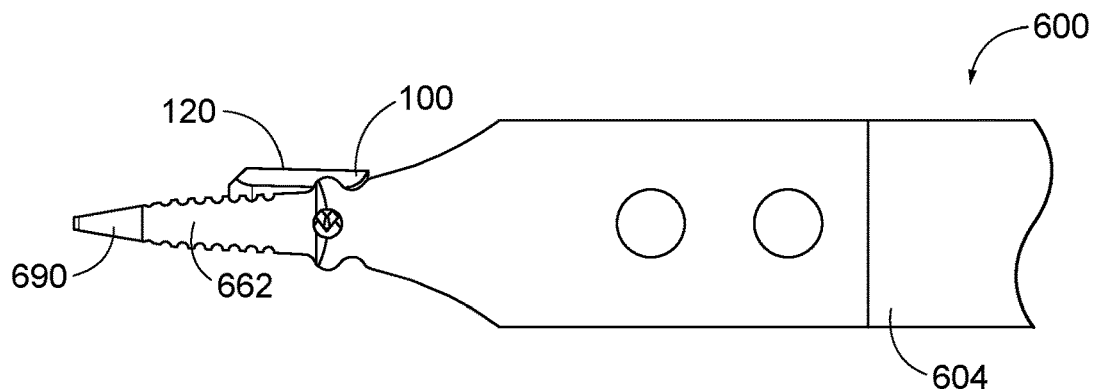
FIG. 3 is an enlarged, fragmentary view of the decortication tool of FIG. 1 in a first position according to some examples of the present disclosure.

Referring to FIGS. 3-6, the decortication tool 100 may be utilized with the guide tube 604. In such examples, the guide tube 604 is inserted posteriorly into a spinal facet joint. As the guide tube 604 is inserted into the facet joint, the anchoring mechanism 662 fixes the guide tube 604 in position relative to (e.g., at least partially within) the facet joint. Once the guide tube 604 is anchored or otherwise positioned, the decortication tool 100 is inserted through the internal bore 680 of the guide tube 604. For instance, as shown in FIG. 3, the decortication head 120 may be positioned in its first position to allow slidable insertion of the decortication tool 100 within the guide tube 604.

Figure 4:
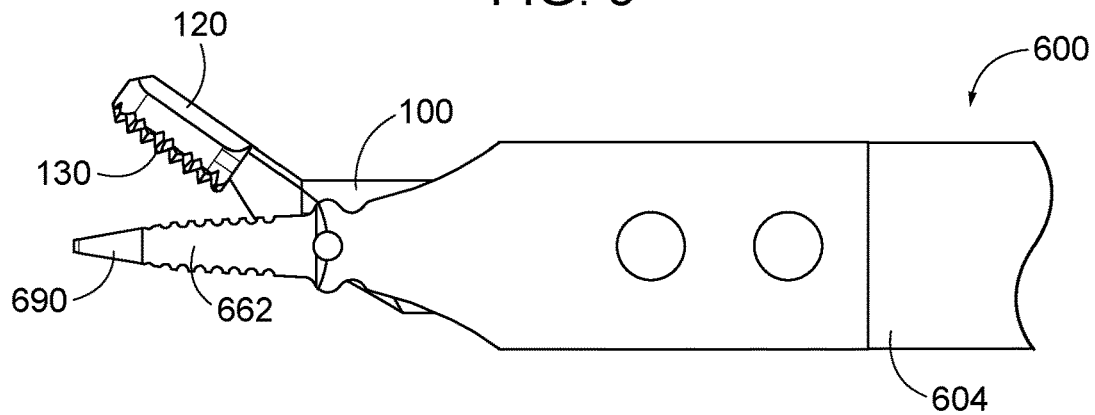
FIG. 4 is an enlarged, fragmentary view of the decortication tool of FIG. 1 in a second position according to some examples of the present disclosure.
Figures 5, 6:
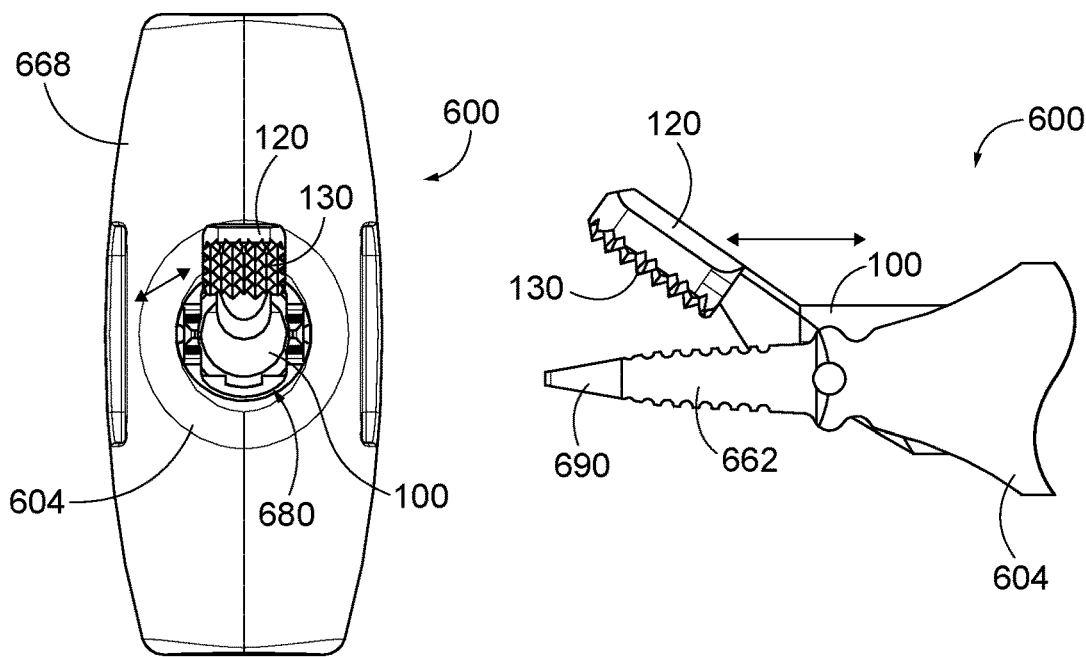
FIG. 5 is a front elevation view of the decortication tool of FIG. 1 in the second position and showing a first movement of the decortication tool to decorticate bone.
FIG. 6 is a side elevation view of the decortication tool of FIG. 1 in the second position and showing a second movement of the decortication tool to decorticate bone.

Referring to FIG. 4, once the decortication head 120 reaches the facet space or joint, the decortication head 120 may be moved to its second position to begin decortication of one or more bony surfaces of the facet joint. For example, as shown in FIGS. 5 and 6, respectively, the decortication head 120 may be rotated left to right (medial, lateral) or moved back and forth to decorticate bone via the rasp 130. As noted above, movement of the decortication head 120 may be accomplished by user manipulation of the handle 114 and/or shaft 102 of the decortication tool 100. With the anchoring mechanism 662 anchored to the facet joint, the decortication head 120 may move relative to the guide tube 604 in decorticating bone.

Referring to FIGS. 8 and 9, the decortication tool 200 may also be utilized with the guide tube 604. In such examples, the guide tube 604 is inserted posteriorly into a spinal facet joint. As the guide tube 604 is inserted into the facet joint, the anchoring mechanism 662 fixes the guide tube 604 in position relative to (e.g., at least partially within) the facet joint. Once the guide tube 604 is anchored or otherwise positioned, the decortication tool 200 is inserted through the guide tube 604. Once the decortication head 220 reaches the facet space, the decortication head 220 may be rotated, such as back and forth, to decorticate bone tissue. As one example, the decortication head 220 may be rotated to decorticate the space below the facet joint, though the decortication head 220 may be positioned to decorticate other locations of the facet joint.

Referring to FIG. 11, the decortication tool 300 may also be utilized with the guide tube 604. In such examples, the guide tube 604 is inserted posteriorly into a spinal facet joint. As the guide tube 604 is inserted into the facet joint, the anchoring mechanism 662 fixes the guide tube 604 in position relative to (e.g., at least partially within) the facet joint. Once the guide tube 604 is anchored or otherwise positioned, the decortication tool 300 is inserted through the guide tube 604 until the decortication head 320 reaches the facet space. Once in position, the decortication head 320 may be rotated such that the one or more burrs decorticate desired bone tissue. For example, as noted above, the first geometry 350 may be positioned within the facet joint to decorticate inside the facet space. The second geometry 352 may be positioned outside the facet joint to decorticate the space outside the facet joint simultaneously with the first geometry 350.

Figure 20:
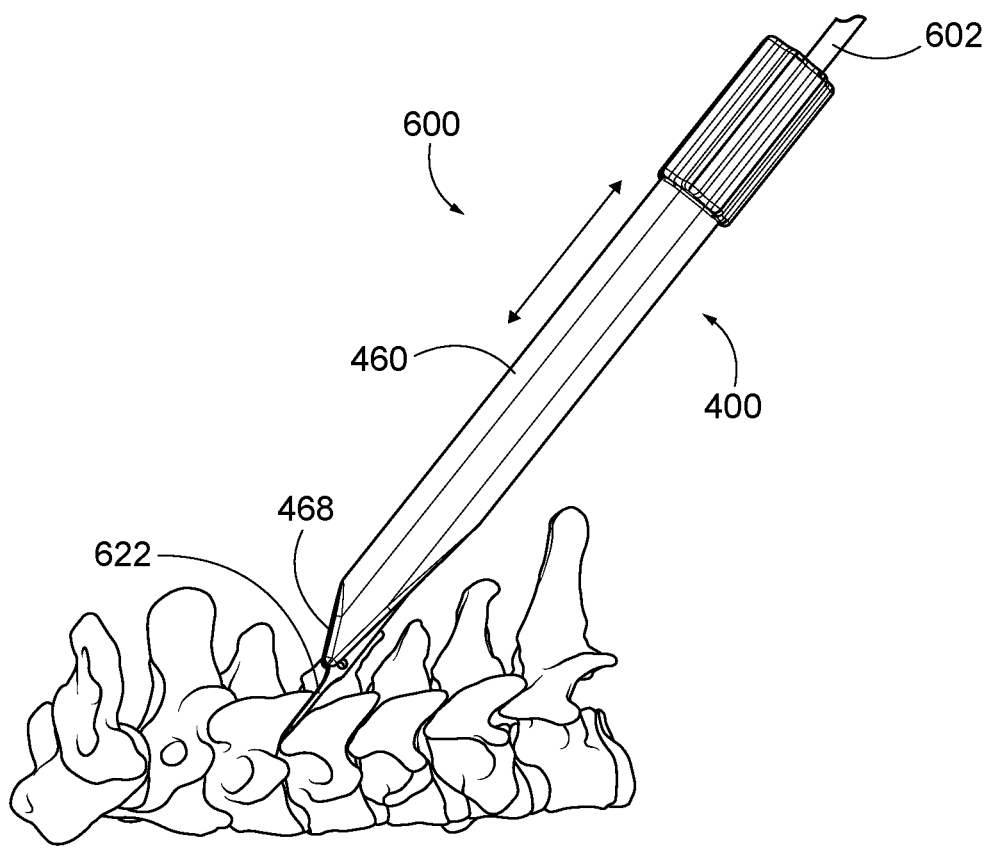
FIG. 20 is an elevation view of the sheath of the decortication tool of FIG. 14 slid along the access chisel of FIG. 19.

Referring to FIGS. 19-24, the decortication tool 400 may be utilized with the access chisel 602. In such examples, the access chisel 602 is inserted posteriorly into a spinal facet joint. As the access chisel 602 is inserted into the facet joint, the tip portion 622 of the access chisel 602 may fix the access chisel 602 in position relative to (e.g., at least partially within) the facet joint. Once the access chisel 602 is anchored or otherwise positioned in the facet joint, the sheath 460 of the decortication tool 400 is inserted over the access chisel 602. For instance, as shown in FIG. 20, the access chisel 602 may be slidably received within the first cannula 462 of the sheath 460. Once the access chisel 602 is slidably received within the first cannula 462, the sheath 460 may be moved along the access chisel 602 until the tip 468 of the sheath 460 is positioned at, within, or near the facet space.

Figure 21:
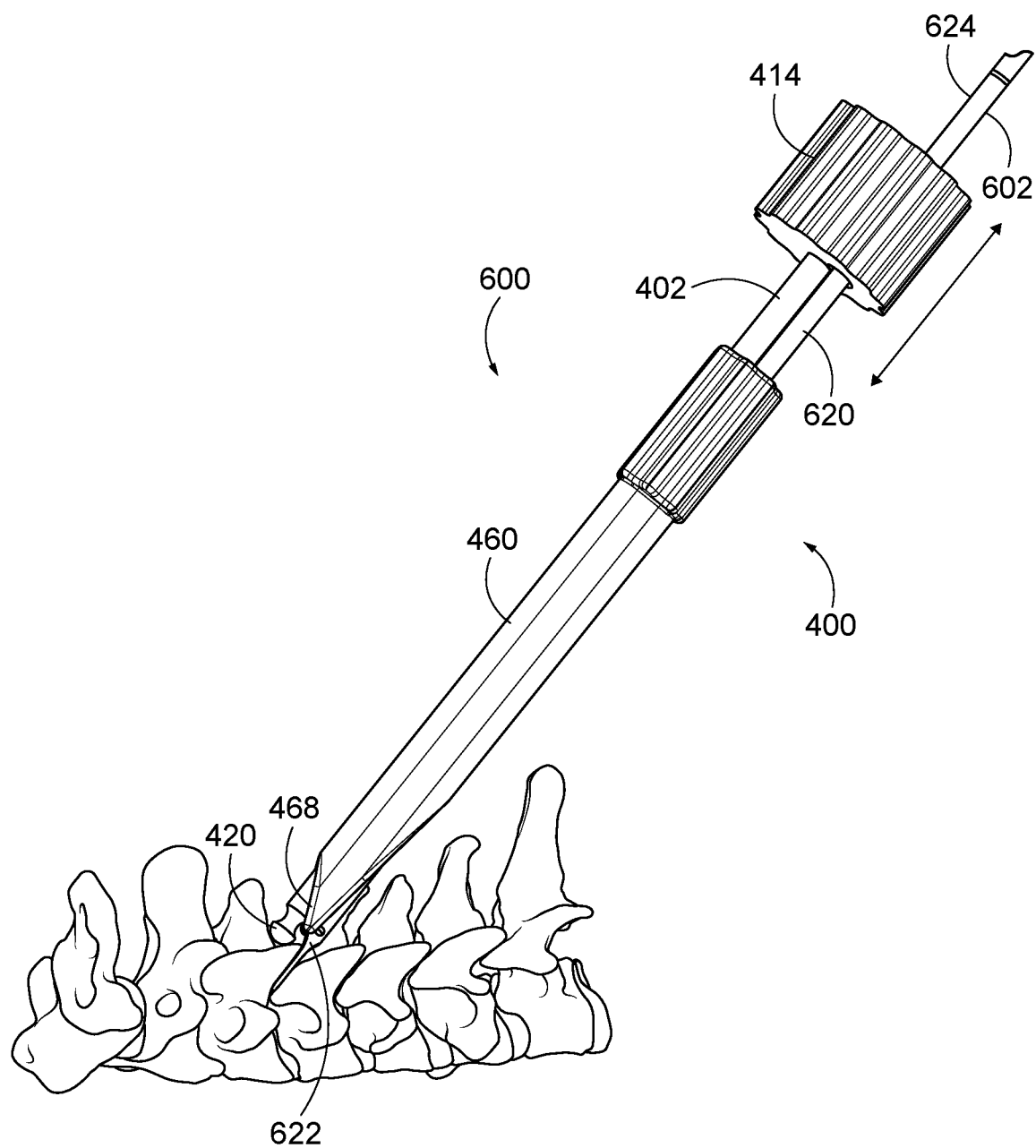
FIG. 21 is an elevation view of the decortication tool of FIG. 14 slid within the sheath.

Referring to FIG. 21, once the sheath 460 is positioned as desired, the shaft 402 of the decortication tool 400 may inserted within the second cannula 464 of the sheath 460. The shaft 402 may be slid down the second cannula 464 of the sheath 460 until the decortication head 420 reaches the facet joint. As the shaft 402 is slid down the second cannula 464 of the sheath 460, a portion of the access chisel 602 (e.g., the head portion 624) may be received within the cutout 470 of the handle 414.

Figure 22:
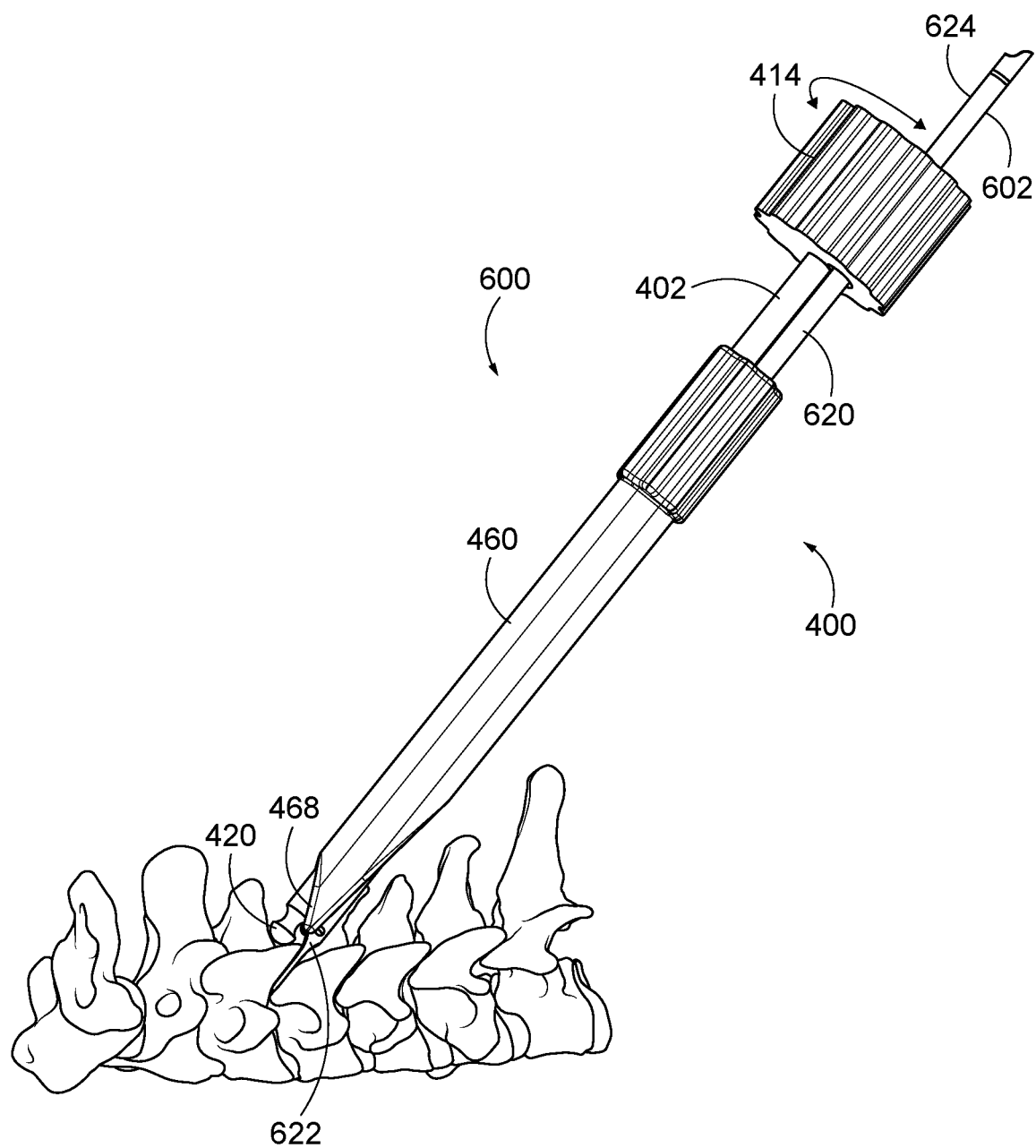
FIG. 22 is an elevation view of the decortication tool of FIG. 14 and showing a first movement of the decortication tool to decorticate bone.
Figure 23:
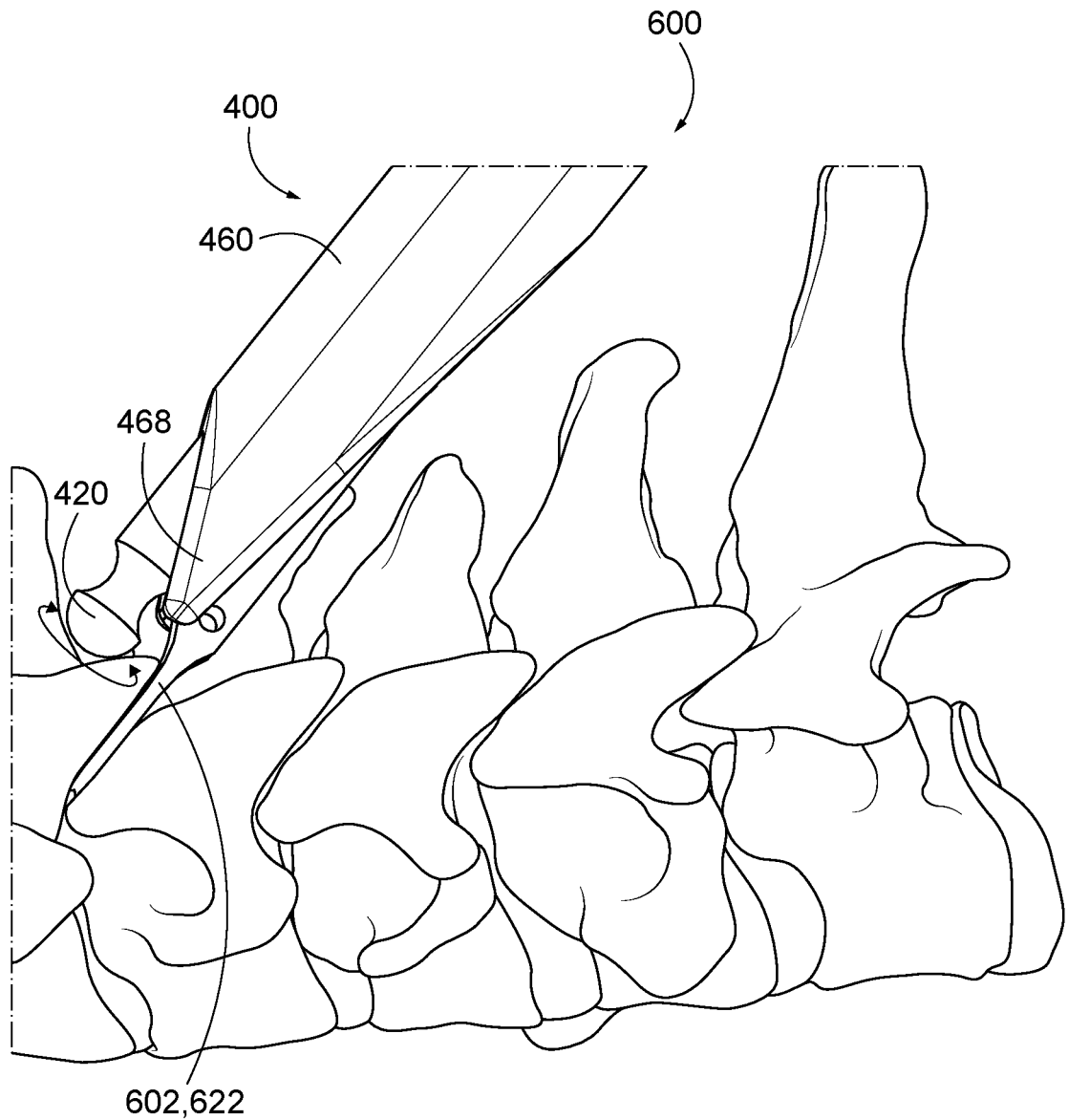
FIG. 23 is an enlarged, detail view of FIG. 22.
Figure 24:
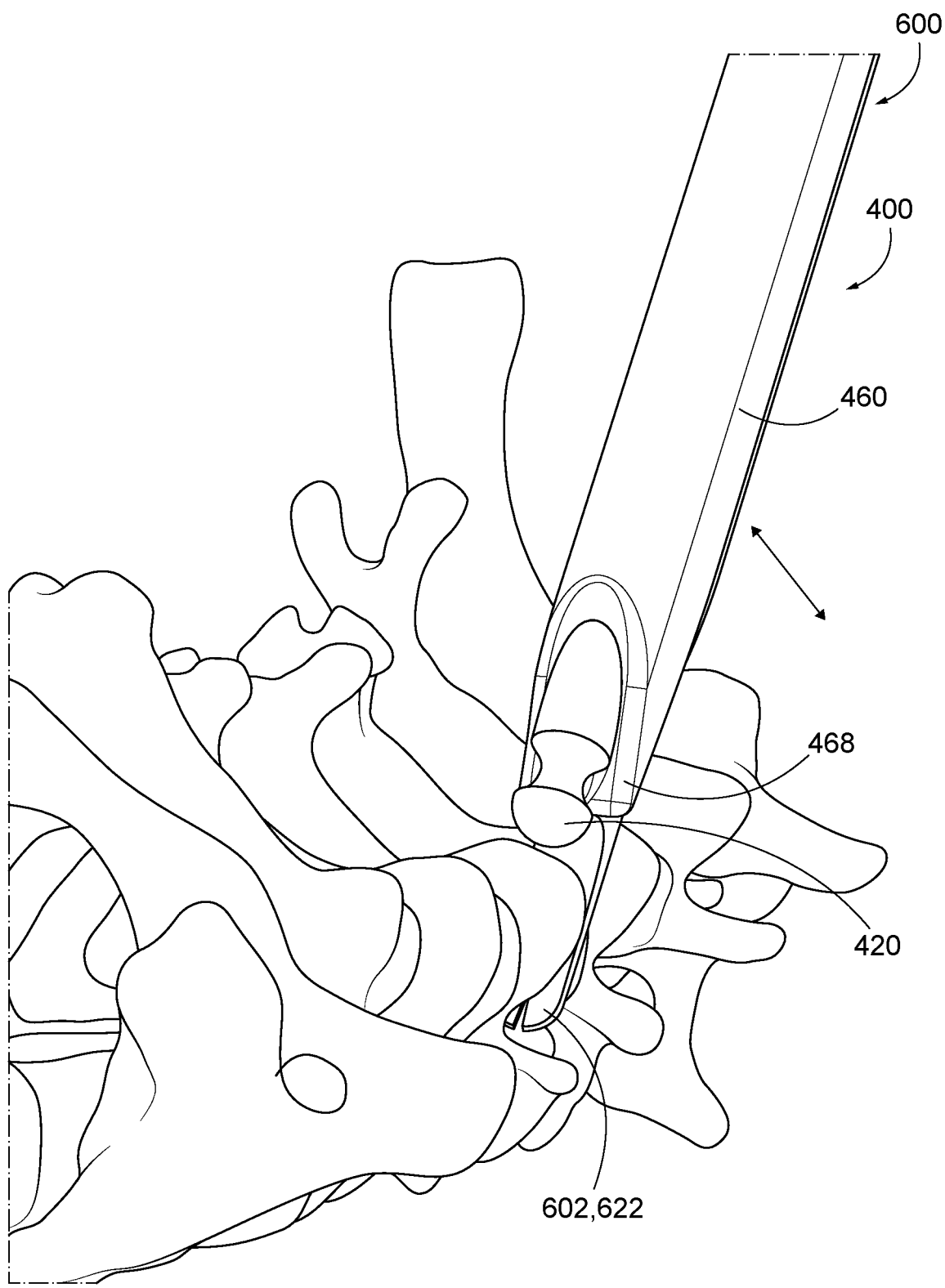
FIG. 24 is a fragmentary view of the decortication tool of FIG. 14 and showing a second movement of the decortication tool to decorticate bone.

Referring to FIGS. 22-24, once the decortication head 420 reaches the facet joint, the decortication tool 400 may be moved such that the decortication head 420 decorticates bony tissue of the facet joint. For example, the handle 414 may be moved to rotate the decortication head 420. As noted above, the shape of the cutout 470 within the handle 414 may allow movement (e.g., rotation) of the handle 414 without dislodging the access chisel 602 from the facet joint. Additionally or alternatively, the sheath 460 may be rotated medial to lateral to decorticate bone to the left or right. If additional reach or decortication is needed, the shaft 402 of the decortication tool 400 may be inserted within another cannula of the sheath 460, such as within the third cannula 466.

Figure 27:
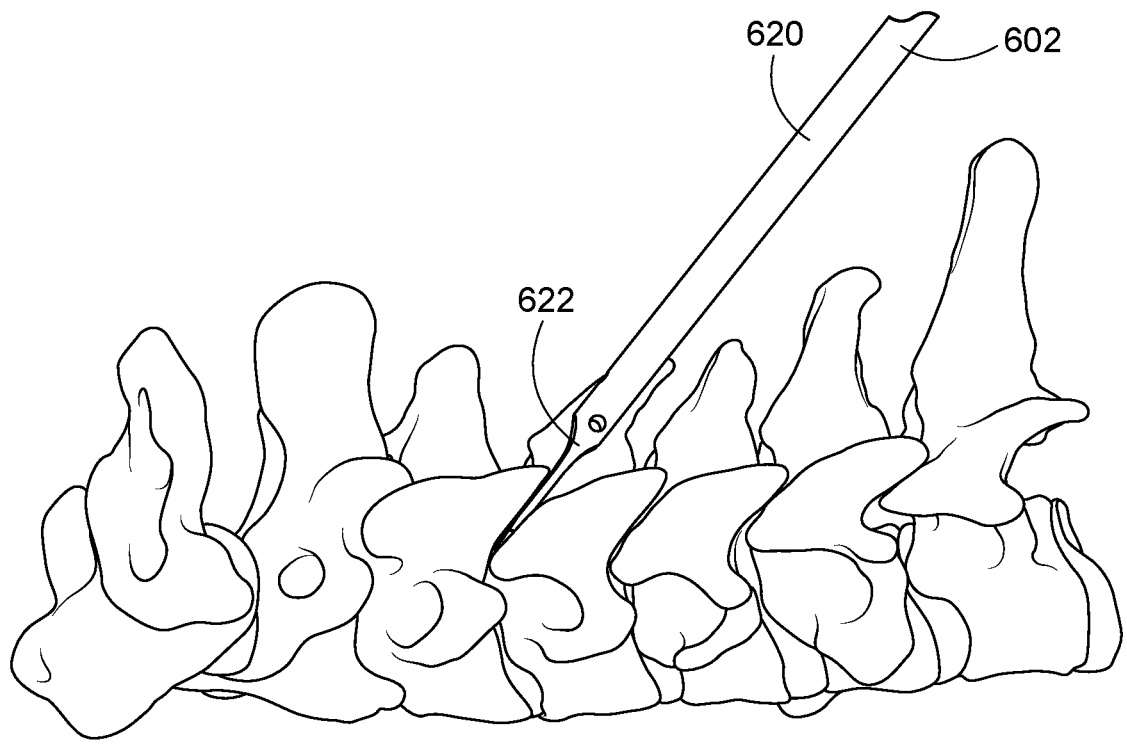
FIG. 27 is an elevation view of an access chisel anchored in a spinal facet joint according to some examples of the present disclosure.
Figure 28:
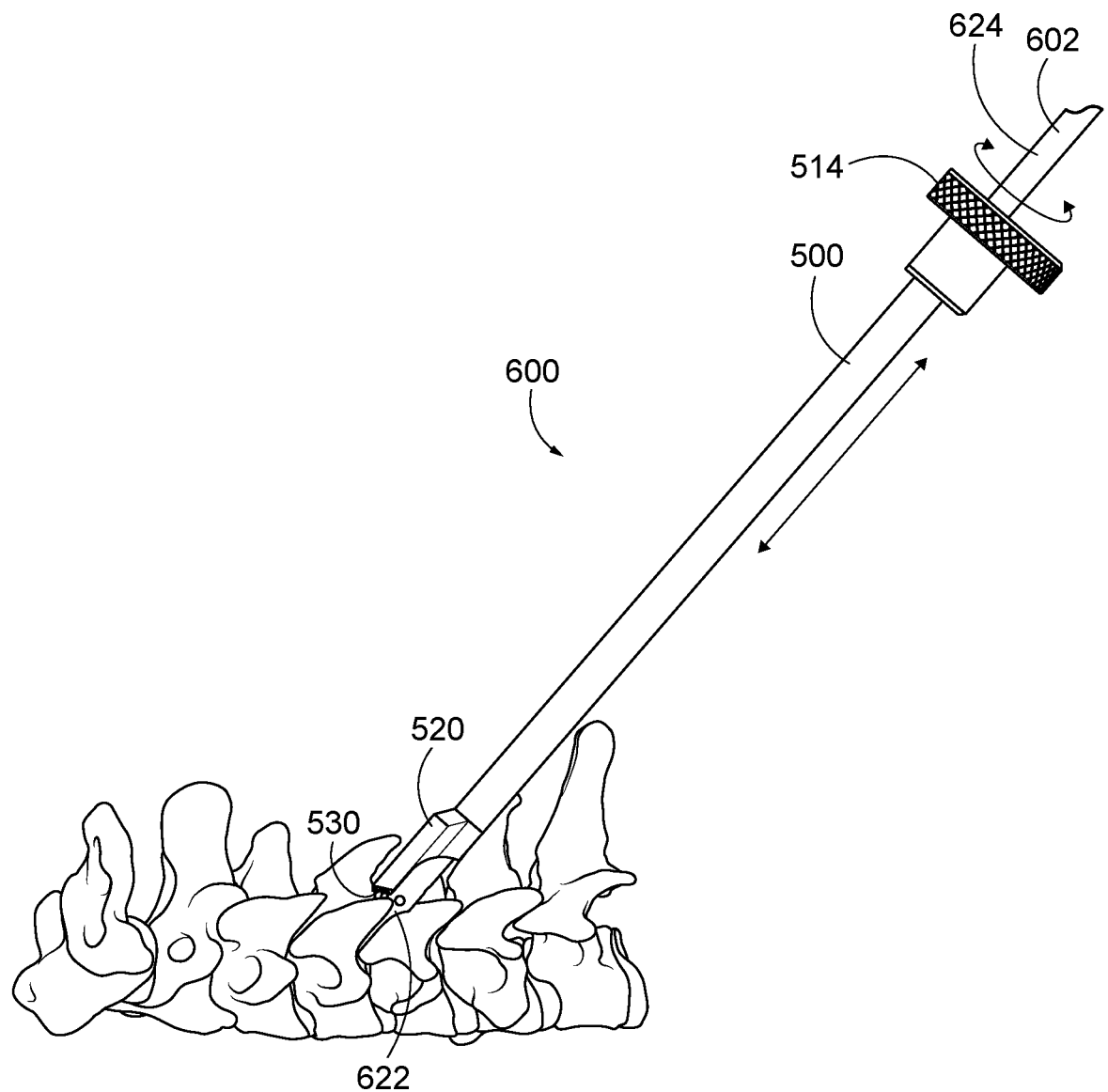
FIG. 28 is an elevation view of the decortication tool of FIG. 25 slid along the access chisel of FIG. 26.
Figure 29:
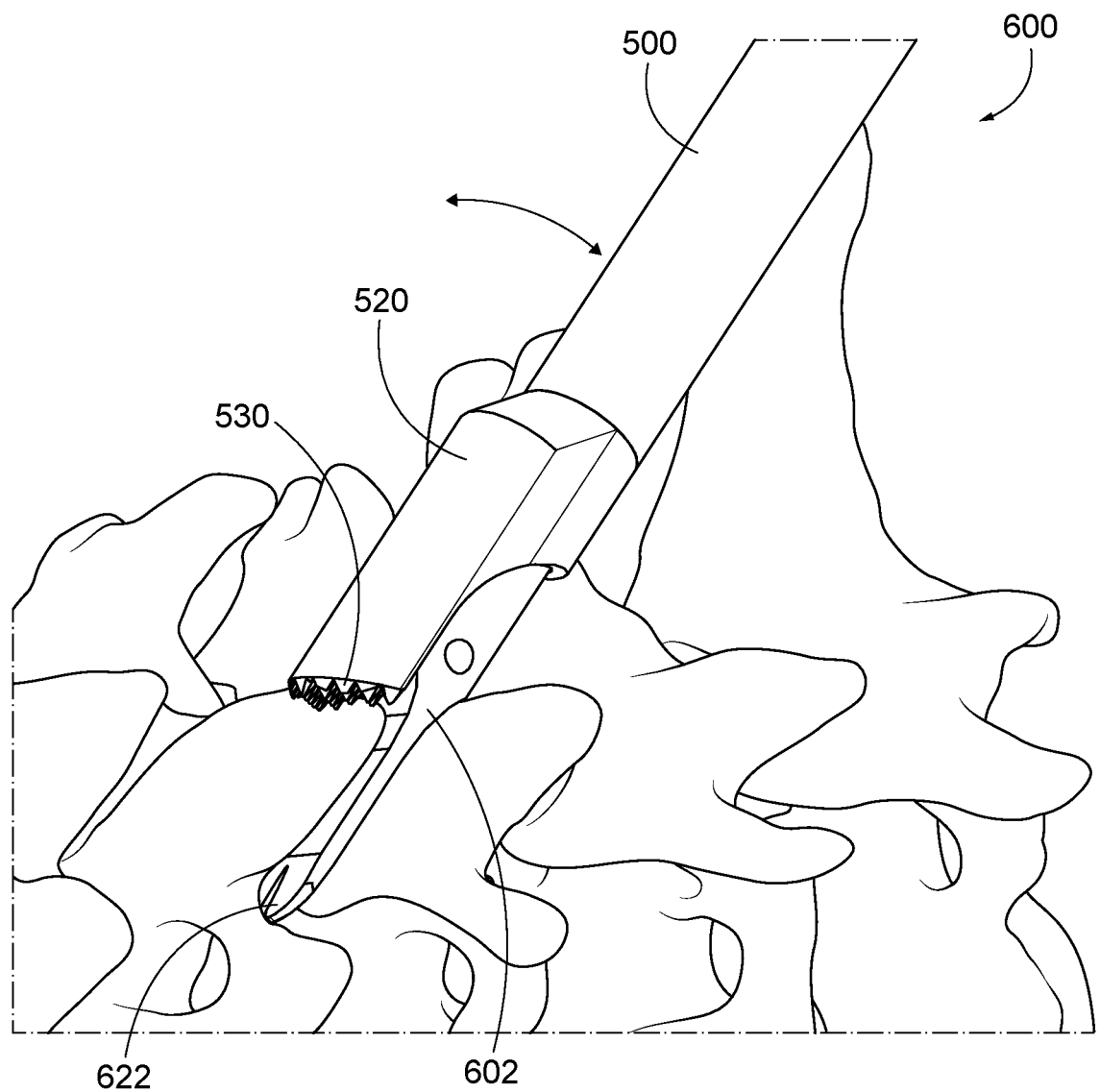
FIG. 29 is an enlarged view of the configuration of FIG. 28 and showing a first movement of the decortication tool to decorticate bone.

Referring to FIGS. 27-29, the decortication tool 500 may also be utilized with the access chisel 602. In such examples, the access chisel 602 is inserted posteriorly into a spinal facet joint. As the access chisel 602 is inserted into the facet joint, the tip portion 622 of the access chisel 602 may fix the access chisel 602 in position relative to (e.g., at least partially within) the facet joint. Once the access chisel 602 is anchored or otherwise positioned in the facet joint, the decortication tool 500 is positioned about the access chisel 602 and moved along the access chisel 602 until the decortication head 520 reaches the facet space. For example, the access chisel 602 may be slidably and rotatably received within the bore 576 of the decortication tool 500.

Once the decortication head 520 reaches the facet space, the decortication tool 500 may be moved to decorticate bone. For instance, the decortication tool 500 may be rotated back and forth via the handle 514 such that the rasp 530 defined on the terminal end surface 588 of the decortication head 520 decorticates bone above the facet joint, though the decortication head 520 may be positioned to decorticate other locations of the facet joint. Additionally or alternatively, the decortication tool 500 may be rotated medial or lateral with the access chisel 602 to decorticate bone to the left or right.

Once the facet joint is sufficiently decorticated, a spinal implant may be inserted within the facet space to fuse the two adjacent vertebrae together. As noted above, the decortication of bone tissue may promote healing and bone growth around the spinal implant. In this manner, the spinal implant may be fused with bony tissue of the two adjacent vertebrae to fixedly secure the vertebrae together. The spinal implant may include many configurations. As one example, the spinal implant may be similar to the spinal implant disclosed in U.S. patent application Ser. No. 15/489,163, the disclosure of which is hereby incorporated by reference in its entirety.

The spinal implant may be inserted within the facet space in many configurations. For example, the spinal system 600 may include a delivery device 610. In such examples, the spinal implant may be coupled to the delivery device 610 and inserted within the facet space, such as via the guide tube 604. As one example, the delivery device 610 may be similar to the device disclosed in U.S. patent application Ser. No. 15/489,163, the disclosure of which is hereby incorporated by reference in its entirety.

FIGS. 30-40 illustrate various views of a multi-use instrument 800 for use in a spinal system, such as spinal system 600. Referring to FIGS. 30-40, the multi-use instrument 800, which may be referred to as a multi-assist instrument or simply an instrument, may include a body 802 with opposing first and second sides 804, 806 and opposing first and second surfaces 808, 810. Depending on the particular application, the first and second sides 804, 806 may define front and rear sides of the body 802, though other configurations are contemplated. Similarly, the first and second surfaces 808, 810 may define top and bottom surfaces of the body 802, though other configurations are contemplated. The body 802 may be referred to as a handle, and as such, includes a form factor designed to fit comfortably in a user's hand.

The body 802 may include many configurations. For example, the body 802 may be at least partially hollow with a cavity 820 defined therein. In such examples, the cavity 820 may be open to the second surface 810 of the body 802. In some examples, the cavity 820 may also be open to the first side 804 of the body 802. The body 802 may include a slot 822 defined in the first side 804 along a length of the body 802 between the first and second surfaces 808, 810. As shown, the slot 822 may be in communication with the cavity 820. In one example, the body 802 includes an alignment window 824 defined in the first side 804 of the body 802. Similar to the slot 822, the alignment window 824 may be in communication with the cavity 820. As shown, the alignment window 824 may extend generally perpendicular to the slot 822.

In some examples, the body 802 may include a channel 830 defined in its first side 804 to define an indented space along the body. For instance, the channel 830 may be defined in the first side 804 from adjacent to the first surface 808 to adjacent to the second surface 810. In such examples, the slot 822 and alignment window 824 may be defined along the bottom of the channel 830. As explained below, the channel 830 may be sized to match a profile of a fastener or knob, similar to a socket of a socket wrench assembly. For instance, the head of a fastener or knob may be at least partially inserted within the channel 830 and the body 802 used to tighten and/or loosen the fastener or knob through rotation of the body 802. Depending on the particular application, the channel 830 may be shaped such that a fastener or knob is positionable in a plurality of positions along the length of the channel 830 between the first and second surfaces 808, 810. For instance, the fastener or knob may be positioned within the channel 830 adjacent to the first surface 808, adjacent to the second surface 810, or anywhere in between the first and second surfaces 808, 810.

Figure 30:
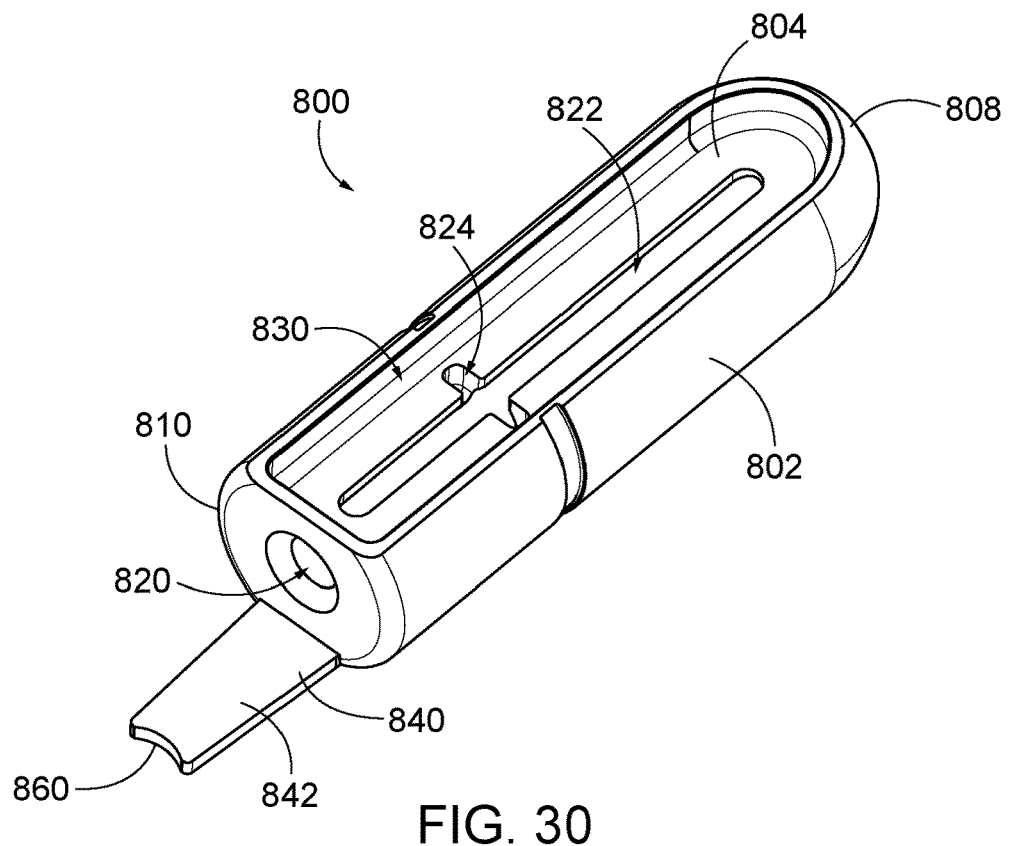
FIG. 30 is a perspective view of a multi-use instrument according to some examples of the present disclosure.
Figure 31:
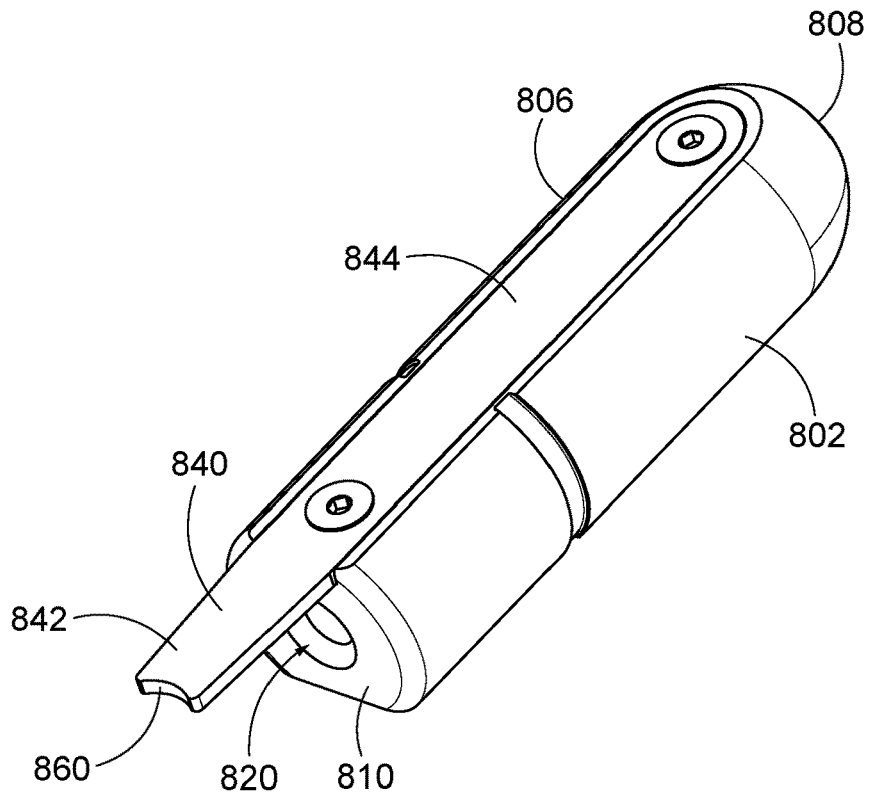
FIG. 31 is another perspective view of the multi-use instrument of FIG. 30.
Figure 32:
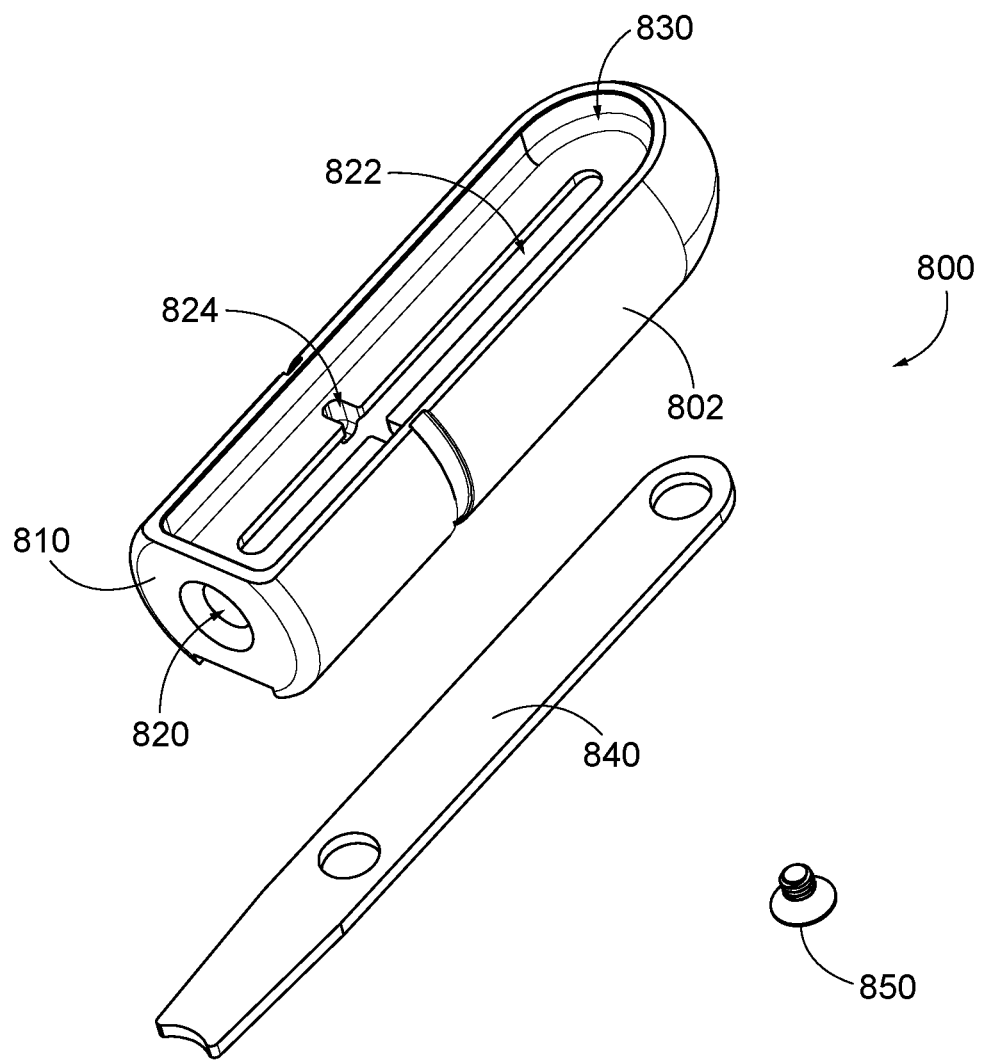
FIG. 32 is an exploded view of the multi-use instrument of FIG. 30.
Figure 32:

Referring to FIGS. 30-32, the instrument 800 may include a bar 840 attached to the second side 806 of the body 802. As shown, a first portion 842 of the bar 840 extends beyond the second surface 810 of the body 802. In such examples, a second portion 844 of the bar 840 is attached to the body 802. The bar 840 may be attached to the body 802 in many configurations. For example, the bar 840 may be attached to the body 802 using one or more fasteners 850, though other configurations are contemplated, including adhesive, heat or sonic welding, or corresponding retention features, among others. In some examples, the bar 840 may be formed integrally with the body 802.

The bar 840 may include many configurations. For instance, the bar 840 may be formed from flat stock. In some examples, the bar 840 may include a convexly-shaped terminal edge 860. In such examples, the bar 840 may taper in width from adjacent to the body 802 to the terminal edge 860.

Figure 33:
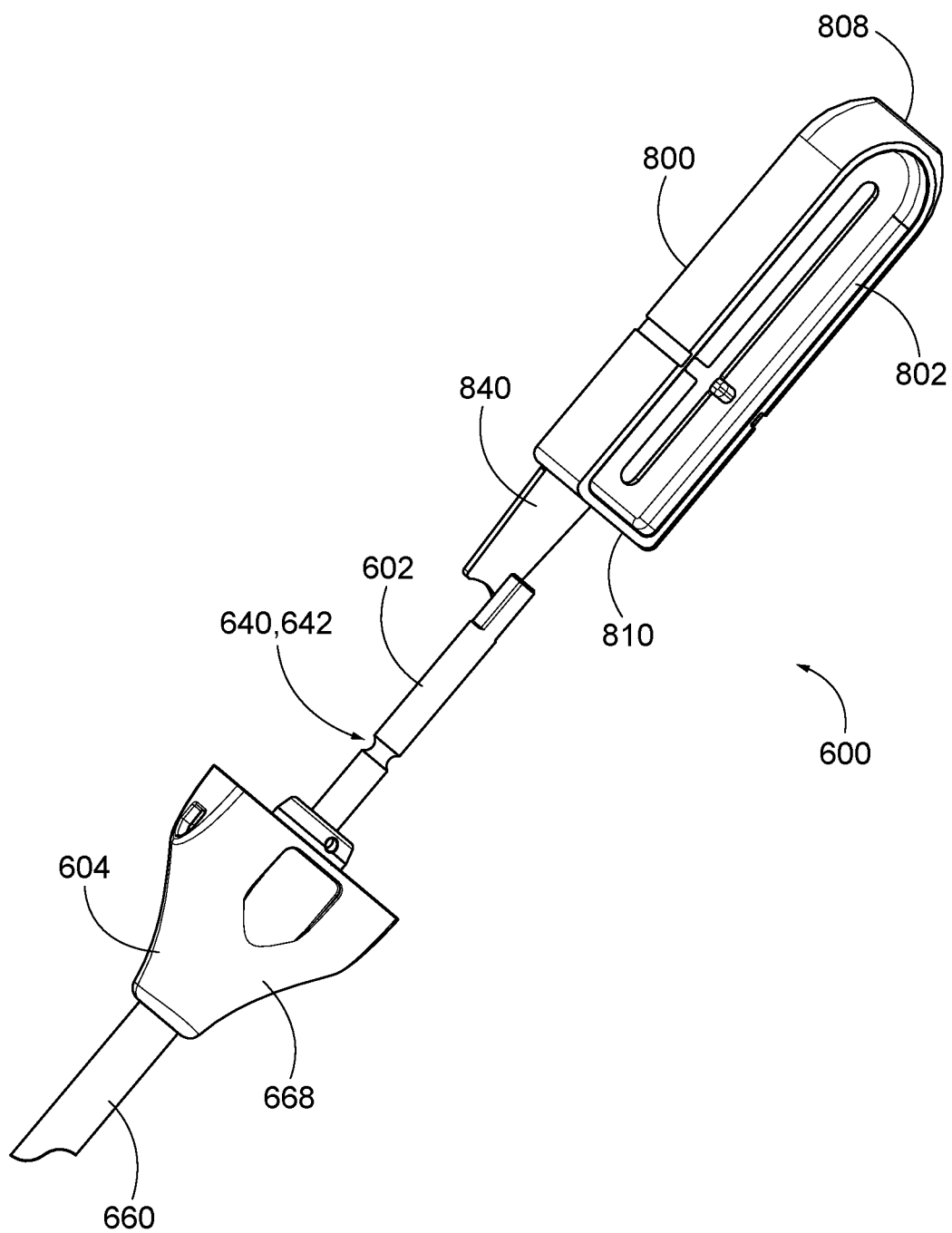
FIG. 33 is a perspective view of the multi-use instrument of FIG. 30 positioned adjacent to an access chisel and a guide tube according to some examples of the present disclosure.
Figure 34:
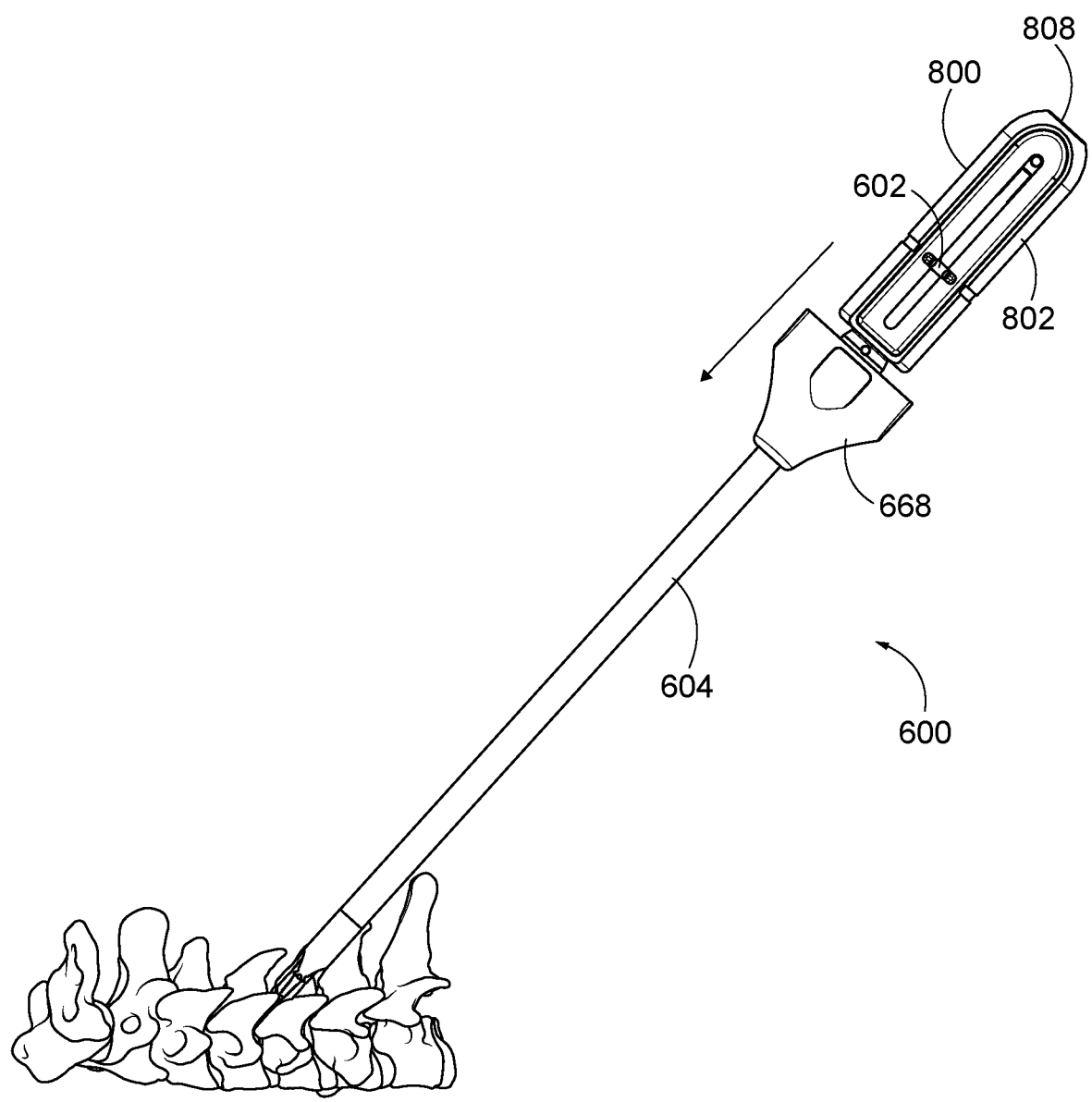
FIG. 34 is a perspective view of the multi-use instrument of FIG. 30 engaged with the access chisel and the guide tube.
Figure 35:
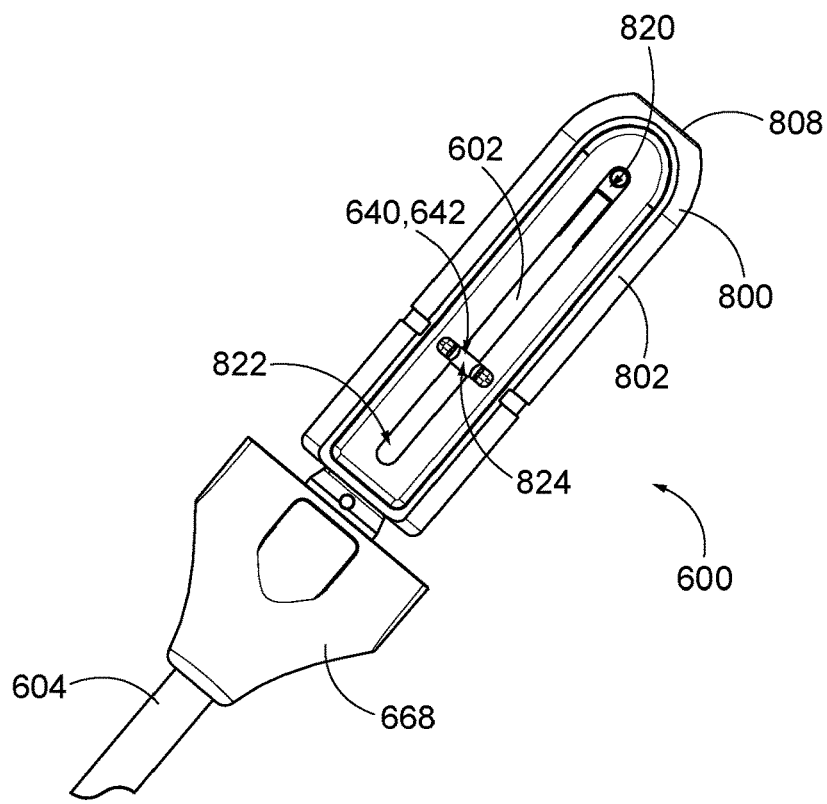
FIG. 35 is an enlarged view of FIG. 33 and showing the multi-use instrument of FIG. 30 aligned with the access chisel.

As noted above, the instrument 800 may be utilized as part of the spinal system 600. In such examples, the instrument 800 may be used to manipulate various components of the spinal system 600. For instance, as shown in FIGS. 33-35, the instrument 800 may be used to advance the guide tube 604 over the access chisel 602 and into the spinal facet joint. In particular, the second surface 810 of the body 802 may engage the handle 668 of the guide tube 604 to push the guide tube 604 along the access chisel 602. In such examples, the first portion 842 of the bar 840 extending beyond the body 802 may engage a lateral side surface of the handle 668 to stabilize the instrument 800 relative to the guide tube 604, or vice versa. Depending on the particular application, force may be applied to the first surface 808 of the instrument 800, such as using a surgical mallet, to advance the guide tube 604 along the access chisel 602.

As the guide tube 604 advances along the access chisel 602, the head portion 624 of the access chisel 602 may be received within the cavity 820 of the body 802. In such examples, the head portion 624 of the access chisel 602 may be visible through at least the slot 822 and alignment window 824 of the body 802. In this manner, the guide tube 604 may be advanced along the access chisel 602 until the guide tube 604 is in a desired position relative to the access chisel 602 as determined by a visible position of the access chisel 602 within the cavity 820. In particular, the guide tube 604 may be fully deployed when the alignment mark 640 of the access chisel 602 aligns with the alignment window 824 defined in the body 802 of the instrument 800 (see FIG. 35).

Figure 36:
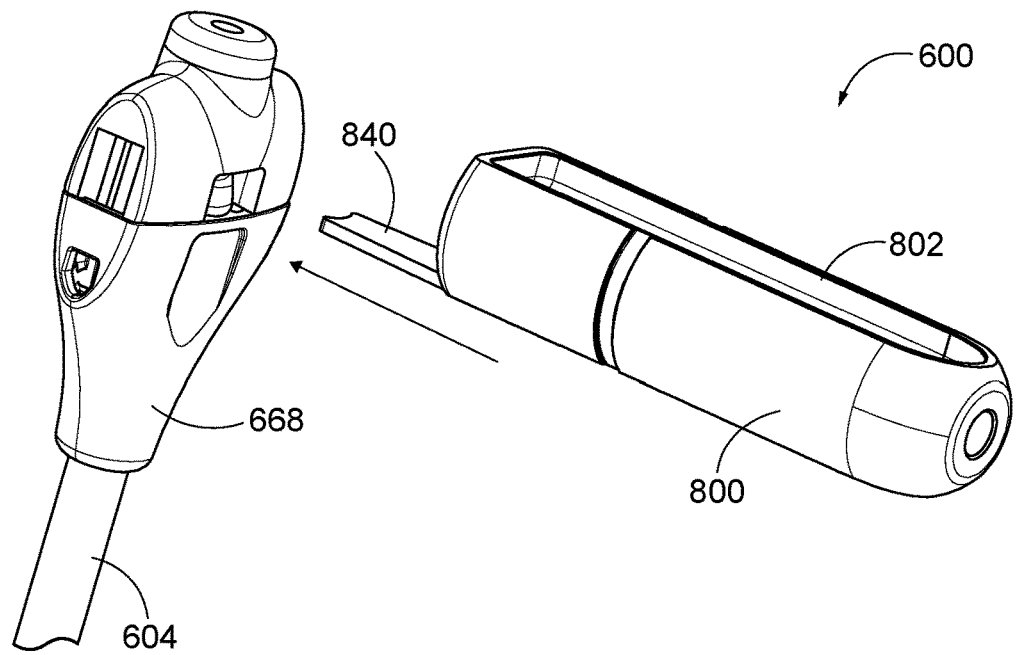
FIG. 36 is a perspective view of the multi-use instrument of FIG. 30 positioned adjacent to a spinal instrument according to some examples of the present disclosure.
Figure 37:
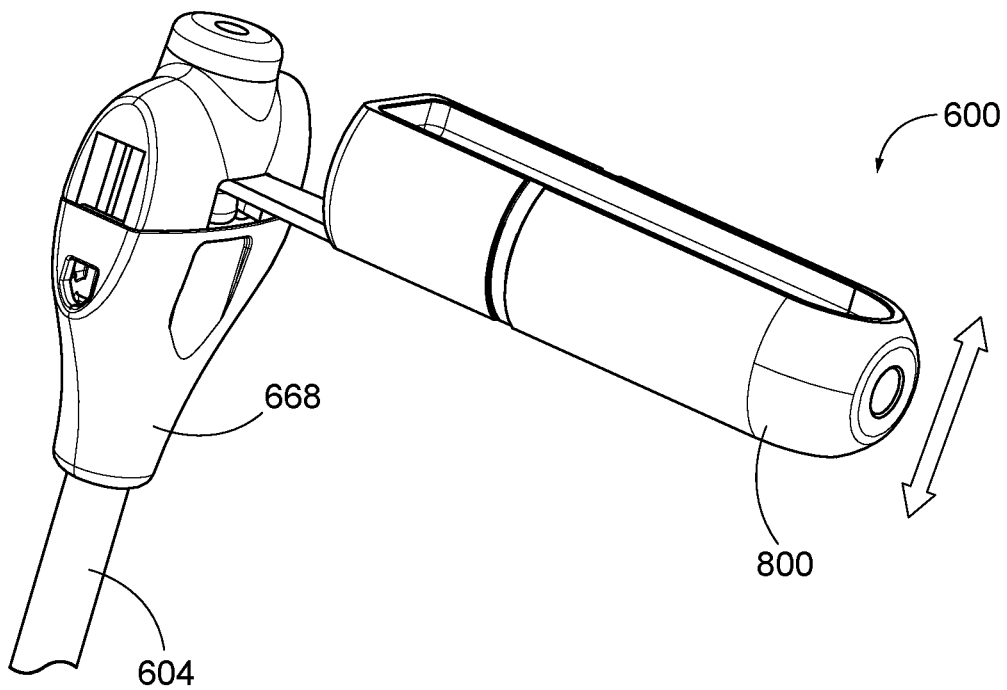
FIG. 37 is a perspective view of the multi-use instrument of FIG. 30 positioned to separate first and second components of the spinal instrument of FIG. 36 according to a first method.
Figure 38:
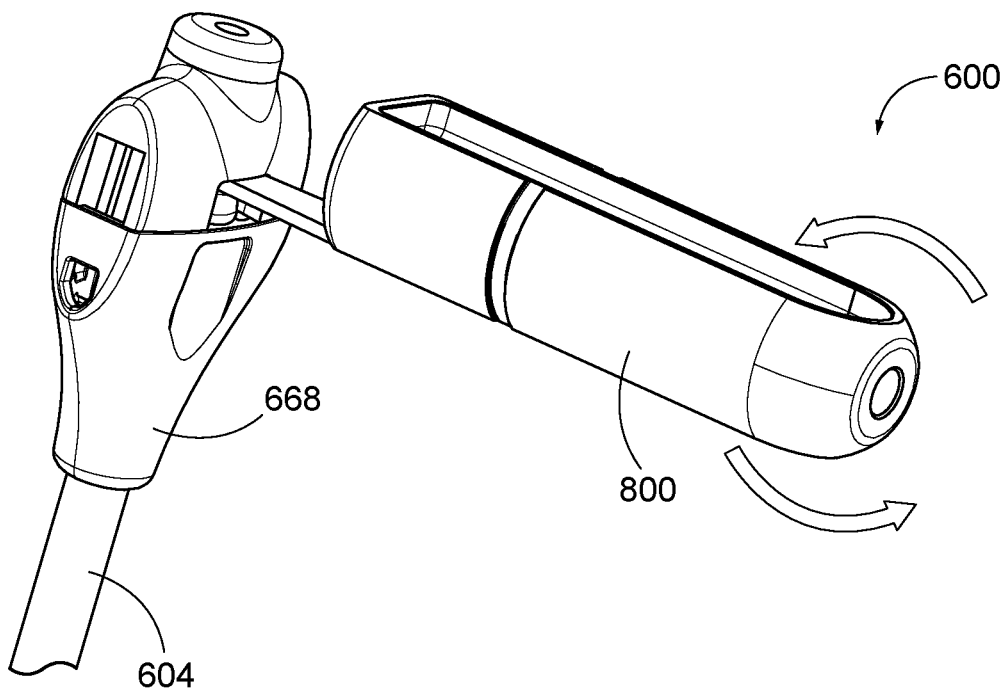
FIG. 38 is a perspective view of the multi-use instrument of FIG. 30 positioned to separate first and second components of the spinal instrument of FIG. 36 according to a second method.

Referring to FIGS. 36-40, the instrument 800 may be used in other manners. For example, as shown in FIGS. 36-38, the bar 840 of the instrument 800 may be inserted between the handle 668 of the guide tube 604 and the handle 114, 214, 314, 414, or 514 of the decortication tool 100, 200, 300, 400, or 500 to separate the components. For instance, either a bending moment (FIG. 37) or a rotational force (FIG. 38) can be applied to the instrument 800 to separate the handle 114, 214, 314, 414, or 514 of the decortication tool 100, 200, 300, 400, or 500 from the handle 668 of the guide tube 604. The bar 840 may be used to separate other components of the spinal system 600. For instance, the bar 840 may be used to separate the guide tube 604 from a chisel rasp or other instrument of the spinal system 600. Once the components are separated by the instrument 800, the instrument 800 may be used to reposition the components as desired. For instance, once the components are separated, the instrument 800 may be used to tap the guide tube 604 back into place, if needed.

Figure 39:
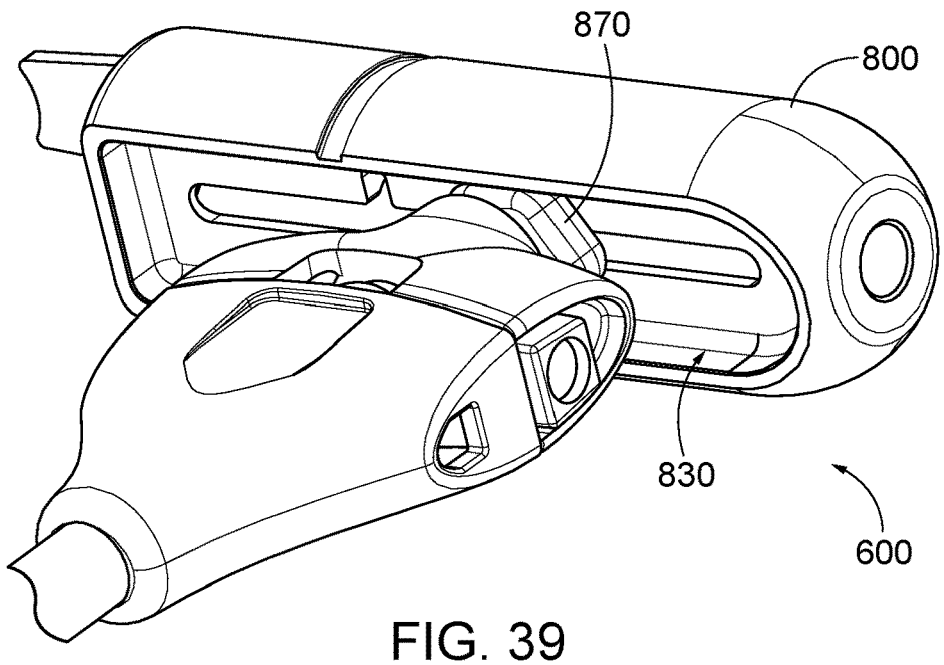
FIG. 39 is a perspective view of the multi-use instrument of FIG. 30 engaged with a spinal instrument according to some examples of the present disclosure.
Figure 40:
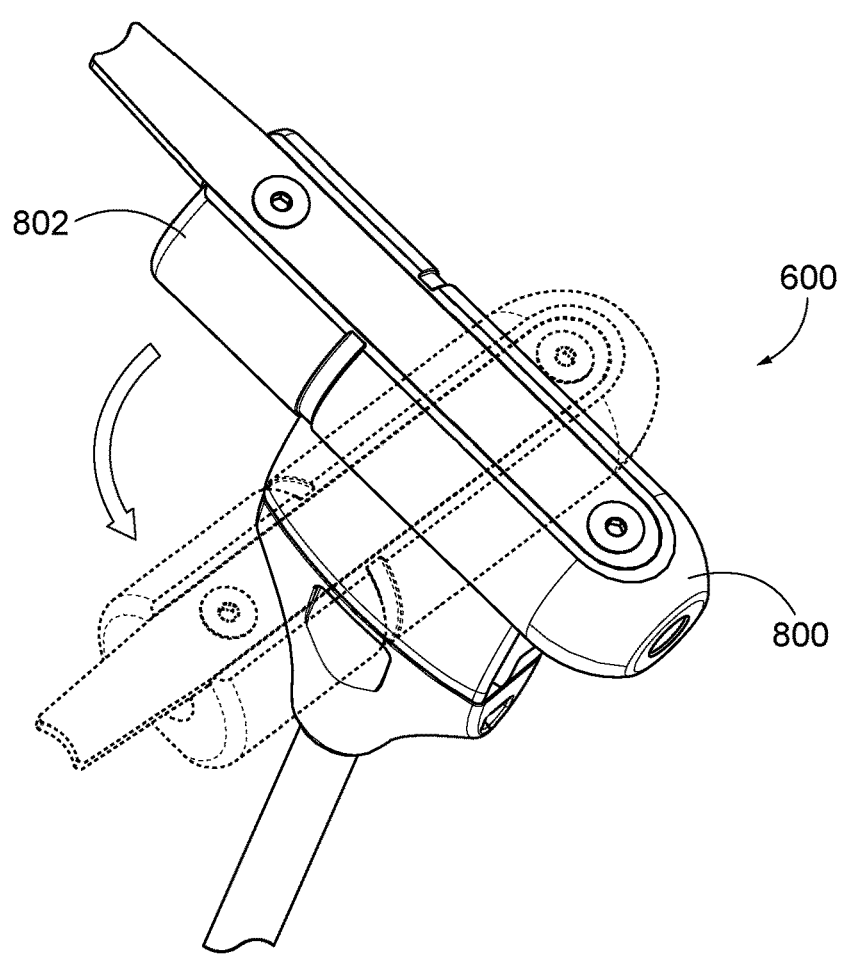
FIG. 40 is a perspective view of the multi-use instrument of FIG. 30 and showing movement of the multi-use instrument to loosen a knob of the spinal instrument of FIG. 39.

As shown in FIGS. 39 and 40, the instrument 800 may be used to loosen a fastener or knob of a spinal system tool. For instance, the delivery device 610 may include a knob 870. Rotation of the knob 870 may perform a function of the spinal system 600, such as selectively delivering a spinal implant within the facet joint. In such examples, the knob 870 may be positioned within the channel 830 of the instrument 800, such as anywhere along the length of the channel 830 between the first and second surfaces 808, 810. Once the knob 870 is positioned within the channel 830, the instrument 800 may be rotated to loosen the knob 870 to deliver the spinal implant within the facet joint. In this manner, the instrument 800 may act like a socket or wrench in loosening the knob 870.

Figures 41A, 41B:
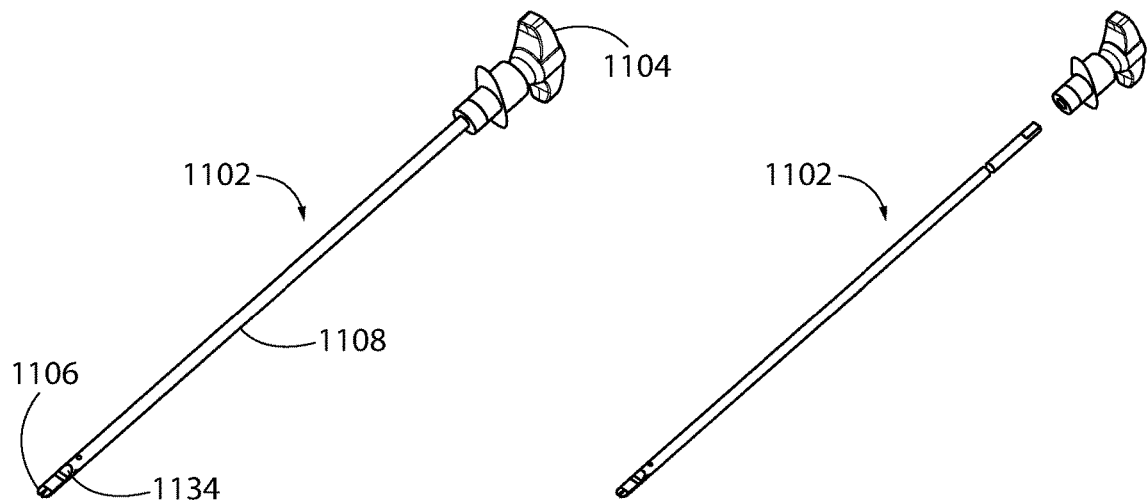
FIG. 41A is a perspective view of an embodiment of an access chisel instrument.
FIG. 41B is an exploded view of the access chisel instrument of FIG. 41A.
Figure 42:
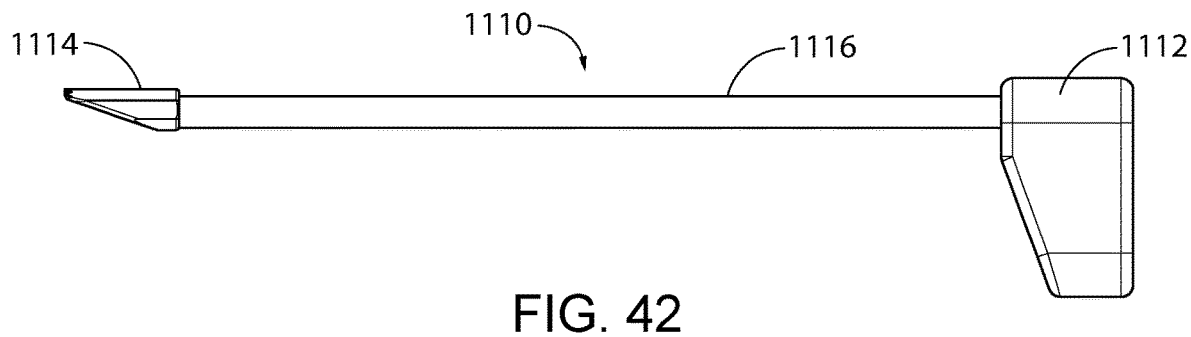
FIG. 42 is a side view of an embodiment of an outer decorticator instrument.
Figure 43:
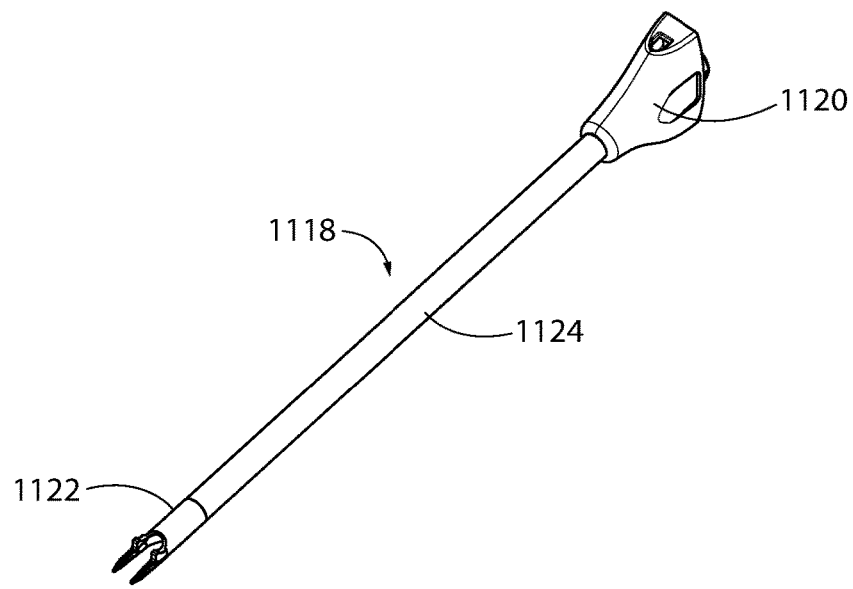
FIG. 43 is a perspective view of an embodiment of a guide tube instrument.
Figure 44:
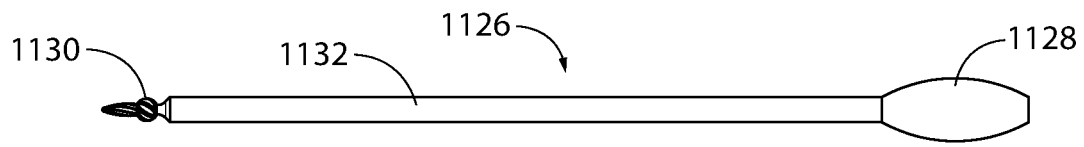
FIG. 44 is a side view of a decorticator burr instrument.

FIGS. 41A-44 include various views of tools that may be included in vertebral joint access, preparation, and delivery, including a chisel, outer decorticator, guide tube, and decorticator burr, the tools including features for improved controlled and targeted decortication and some or all of which may be included as part of spinal system 600. FIG. 41A is a perspective view of an embodiment of an access chisel 1102 instrument. FIG. 41B is an exploded view of the access chisel 1102 instrument of FIG. 41A. FIG. 42 is a side view of an embodiment of an outer decorticator 1110 instrument. FIG. 43 is a perspective view of an embodiment of a guide tube 1118 instrument. FIG. 44 is a side view of a decorticator burr 1126 instrument.

As shown in FIGS. 41A-41B, the chisel 1102 may include a proximal portion 1104 that includes a handle, a distal portion that includes a chisel tip 1106, such as a chamfered tip forming a nose of the chisel 1102, and a tongue 1134. The distal portion and the proximal portion 1104 may be connected by a tubular shaft 1108.

As shown in FIG. 42, the outer decorticator 1110 may include a proximal portion 1112 formed to engage a handle or otherwise allow a practitioner to directly or indirectly (such as through a robotic arm) grasp the proximal portion 1112 to rotate the outer decorticator 1110 to operate the outer decorticator 1110. A tubular shaft 1116 connects the proximal portion 1112 to a distal portion 1114. The distal portion 1114 may be shaped with a decorticator or rough surface that may be used to roughen or abrade the surface of a target deployment area. In some examples, the shaft 1116 of the outer decorticator 1110 is hollow, with a larger inner diameter than an outer diameter of the shaft 1108 of the chisel 1102. In use, the shaft 1116 of the outer decorticator 1110 may be slid over the shaft 1108 of the chisel 1102. The distal portion 1114 of the outer decorticator 1110 may be larger than the outside diameter of the shaft 1116. This aspect may provide more stability when engaging the outer decorticator 1110 to the targeted area for improved controlled and targeted decortication.

As shown in FIG. 43, the guide tube 1118 may include a tubular shaft 1124 connecting a proximal portion 1120 that is connected to forks 1122 formed at the distal end of the guide tube 1118. The shaft 1124 may be hollow, with an inner diameter that is larger than the outer diameter of the chisel shaft 1108. In use, the guide tube 1118 may be slid over the chisel 1102 to position the forks 1122 within the target facet joint space. Once the forks 1122 are positioned, the chisel 1102 may be removed by sliding the chisel tip 1106 and shaft 1108 of the chisel 1102 through the hollow shaft 1124 of the guide tube 1118.

As shown in FIG. 44, the decorticator burr 1126 may include a proximal portion 1128, a burred end 1130 formed at a distal portion opposite the proximal end 1128, and a tubular shaft 1132 connecting the proximal portion 1128 and burred end 1130. The outer diameter of the shaft 1132 may be smaller than the inner diameter of the guide tube shaft 1124. In use, the burred end 1130 of the decorticator burr 1126 may be inserted into the proximal portion 1120 of the guide tube 1118, and slid through the shaft 1124 until it extends between and/or past the forks 1122 of the guide tube 1118.

In some examples, the vertebral joint access and preparation devices described in FIGS. 41A-44 may be utilized to deliver a vertebral joint implant. It can be appreciated that the practitioner may use a robotic arm or other robotic surgical instrument to perform any, some or all of these steps as described here and elsewhere in the application. In some examples, a practitioner may make an incision in a patient and expose targeted bony elements. The practitioner may then insert the access chisel 1102, inserting the chisel tip 1106 into the target location. The practitioner may then slidably insert the outer decorticator 1110 (may also be referred to as the trephine) over the access chisel to decorticate superior and inferior lateral masses of the target location. After the superior and inferior lateral masses are decorticated, the outer decorticator 1110 may be slidably removed, leaving the chisel 1102 with its chisel tip 1106 positioned in the target location.

The guide tube 1118 is inserted over the access chisel 1102, positioning the forks 1122 adjacent the outside of the chisel tip 1106. The access chisel 1102 is then slidably removed, sliding within the shaft 1124 of the guide tube 1118. In some examples, a decorticator rasp may then be slidably inserted inside the guide tube 1118 to decorticate the articular surfaces of the target location using the rasp. The decorticator rasp may then be slidably removed from within the guide tube 1118, and the decorticator burr 1126 may then be slidably inserted through the guide tube, with the burred end 1130 extending between and/or past the distal end with forks 1122 to further decorticate the articular surfaces of the target location. The decorticator burr 1126 may then be removed from within the guide tube 1118. Other spinal instrumentation may then be used, including but not limited to applying bone graft, inserting an implant, or various combinations thereof. In some embodiments, the insertion of the implant may further distract the joint or target delivery location. In some examples, after the implant is delivered, the tool may be removed, and the implant remains in the joint or target delivery location.

Figure 45A:
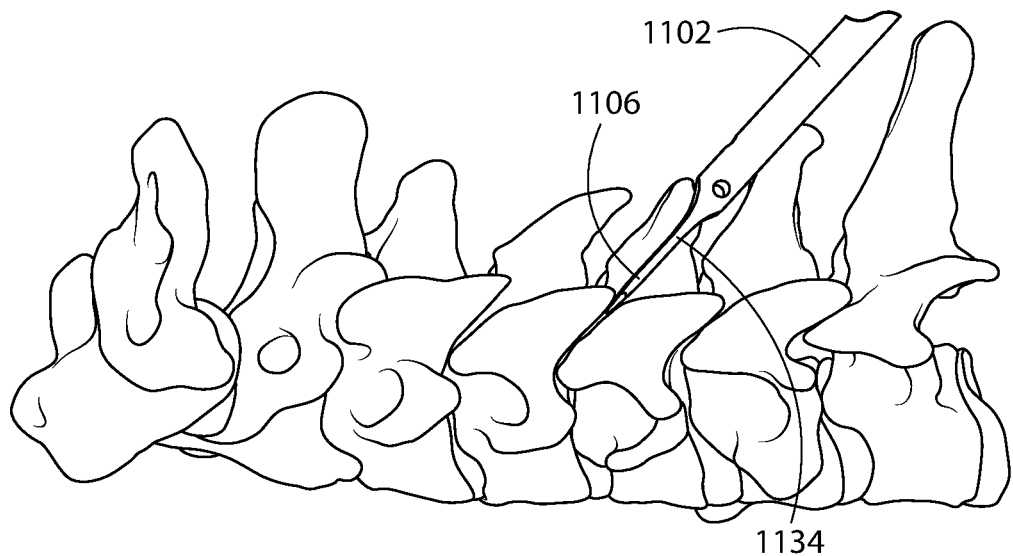
FIG. 45A is a side view of an access chisel introduced into a surgical site and docked near one of two vertebra forming a facet joint.
Figure 45B:
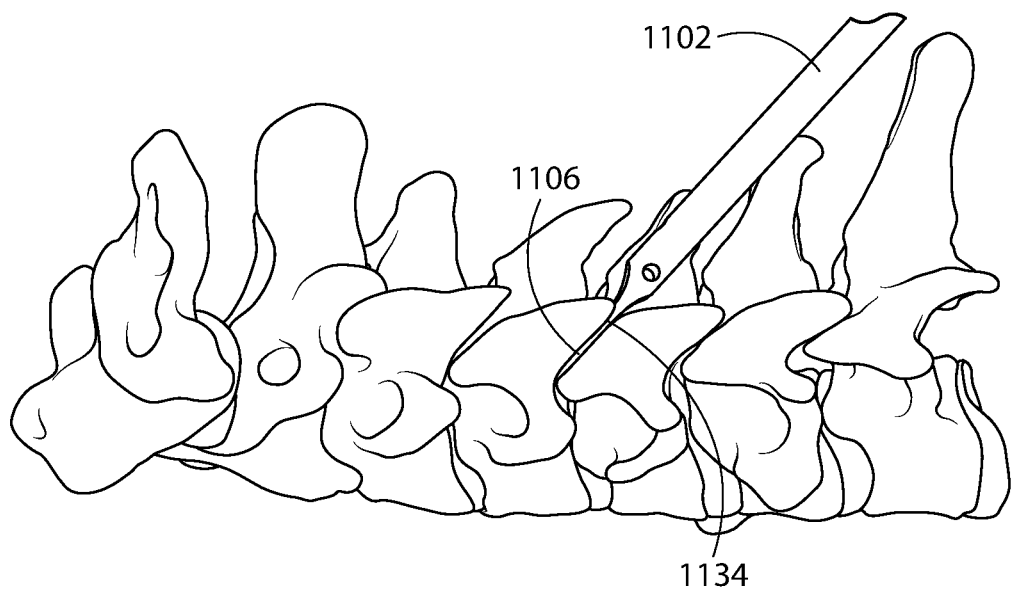
FIG. 45B is a side view of the access chisel of FIG. 45A as it is introduced into the facet space.

FIG. 45A is a side view of an access chisel introduced into a surgical site and docked onto an entry space of a facet joint (i.e. at a superior or inferior vertebra, the vertebrae together forming the facet joint). FIG. 45B is a side view of the access chisel of FIG. 45A docked onto the facet entrance and introduced into the facet joint space. As shown in FIGS. 45A-45B, the chisel 1102 is introduced into the surgical site and is positioned at the facet joint or "docks" onto the entry space of the facet joint. Once the chisel 1102 is docked onto the facet joint entrance, the nose of the chisel tip 1106 is used to break the facet capsule. The tongue 1134 of the chisel 1102 is then introduced into the facet joint space, as shown in FIG. 45B.

Various features and embodiments of access chisels similar to or different than access chisel 1102 are now described. In some embodiments, the chisel may include a single or doubly chamfered nose at a distal end or may have a coped distal end or a combination of coping and chamfering. The tip or nose may include a roughened surface on one or more sides to aid in anchoring or docking the chisel in the facet joint. Additionally, this roughened surface may allow for roughening or decorticating the inner surfaces of the facet joint. The tip or nose may have a length adapted to extend substantially across the facet joint. The tip or nose may include a notch feature, such as notch 3107 of FIG. 66, to provide stability when the chisel is docked to the entry of the facet joint.

Figure 46:
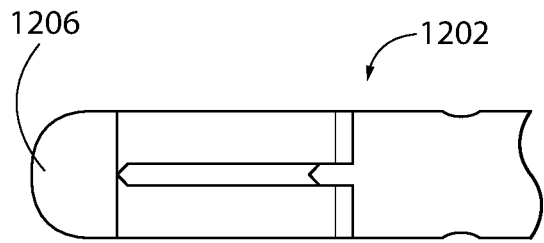
FIGS. 46-51 are top views of the nose portion of various embodiments of an access chisel.
Figure 47:
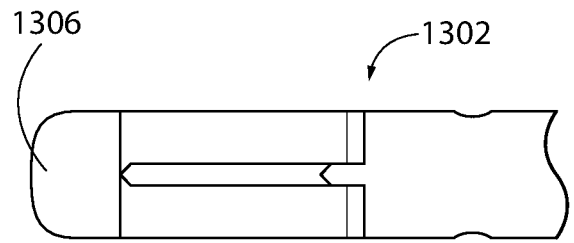
Figure 48:
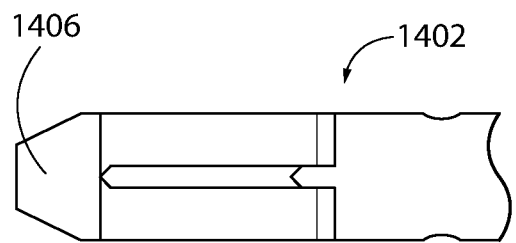
Figure 49:
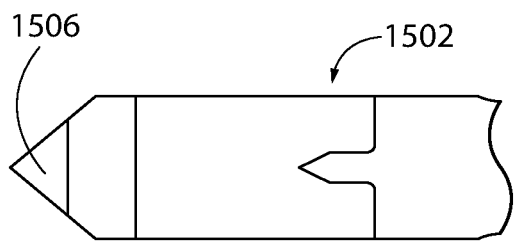
Figure 50:
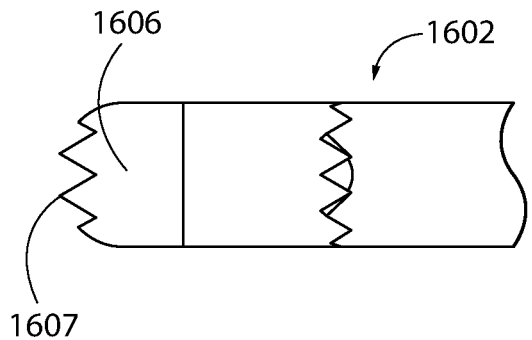
Figure 51:
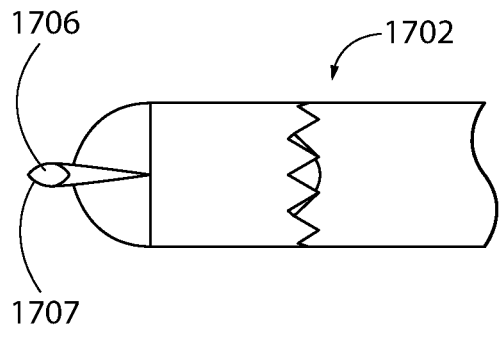
Figure 66:
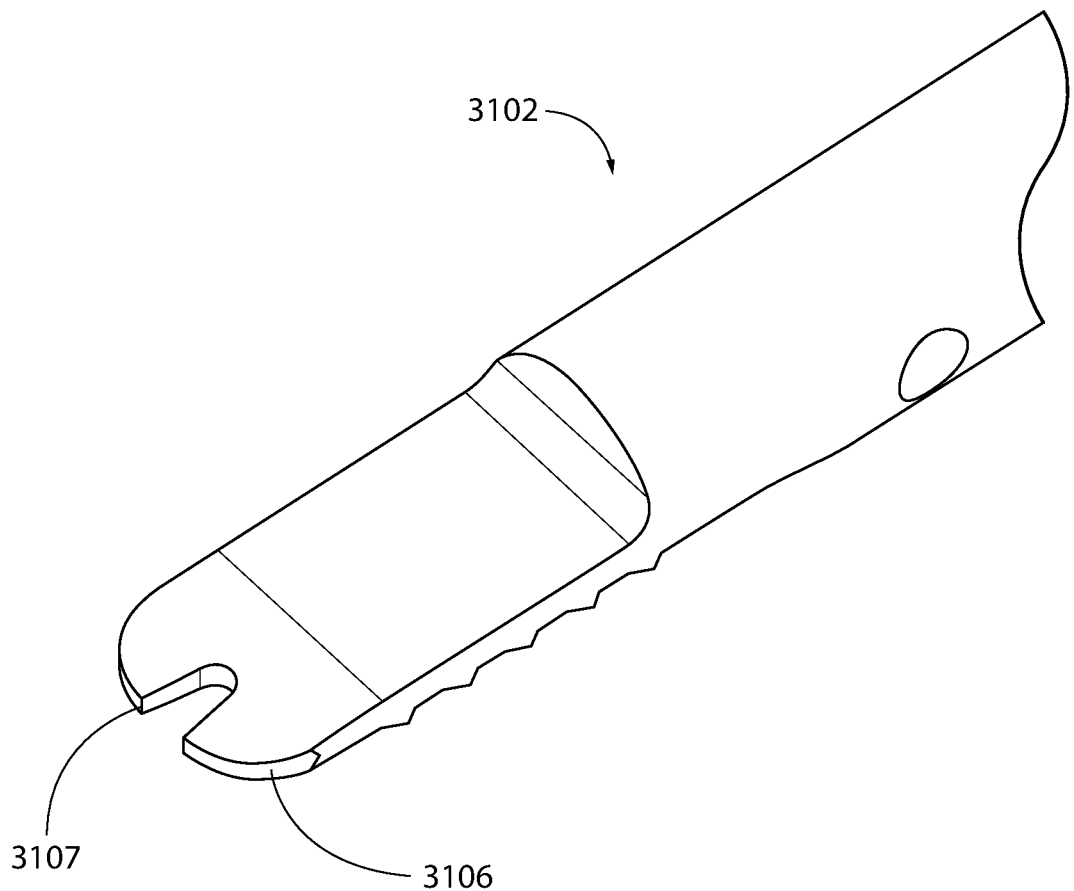
FIG. 66 is a perspective view of the nose portion of an embodiment of an access chisel.

FIGS. 46-51, and 66 show top views of the tip or nose portion of the distal end of various embodiments of access chisels that may be similar to or different than, and used in similar or different methods as previously described access chisels. FIG. 46 shows a chisel 1202 with a nose 1206 that is narrow. FIG. 47 shows a chisel 1302 with a nose 1306 that is wide. FIG. 48 includes a chisel 1402 with a nose 1406 that is tapered. FIG. 49 shows a chisel 1502 with a nose 1506 that is pointed. FIG. 50 shows a chisel 1602 with a nose 1606 that includes teeth 1607. FIG. 51 shows a chisel 1702 with a nose 1706 that includes a pin point 1707. FIG. 66 shows a chisel 3102 with a nose 3106 that includes a notch or cutout feature 3107. The notch 3107 may be u-shaped, rectangular shaped, hemispherical, or oblong. In some examples, the notch 3107 may help to provide stability when the instrument is docked onto the entry of the facet joint, such as shown in FIG. 45A.

Figure 52A:
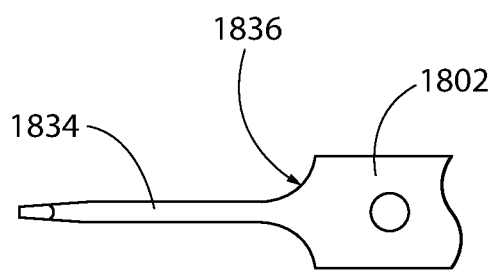
FIG. 52A is a side view of an embodiment of an access chisel.
Figure 52B:
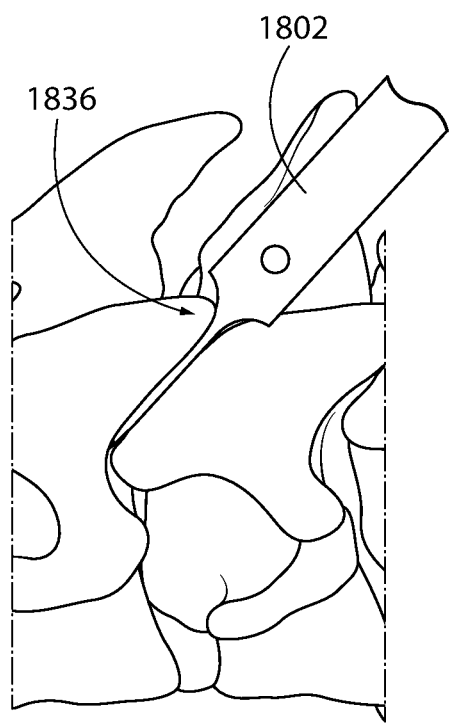
FIG. 52B is a side view of the access chisel of FIG. 52A positioned within the facet space or joint.

FIG. 52A is a side view of an embodiment of an access chisel 1802. FIG. 52B is a side view of the access chisel 1802 of FIG. 52A, shown positioned within the facet space. The access chisel 1802 may include similar or different features, and be used in similar or different methods, than as previously described access chisels. In some embodiments, the access chisel 1802 may include a scalloped feature 1836 on the upper side of the proximal end of the access chisel tongue 1834. In use, the scalloped feature 1836 may prevent the access chisel 1802 from advancing further into the facet joint, and provide stabilization for medial/lateral movement for improved controlled and targeted decortication.

Figure 53A:
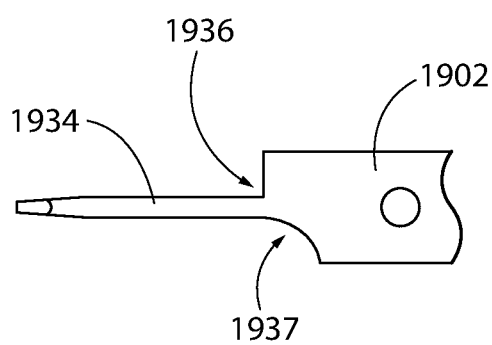
FIG. 53A is a side view of an embodiment of an access chisel.
Figure 53B:
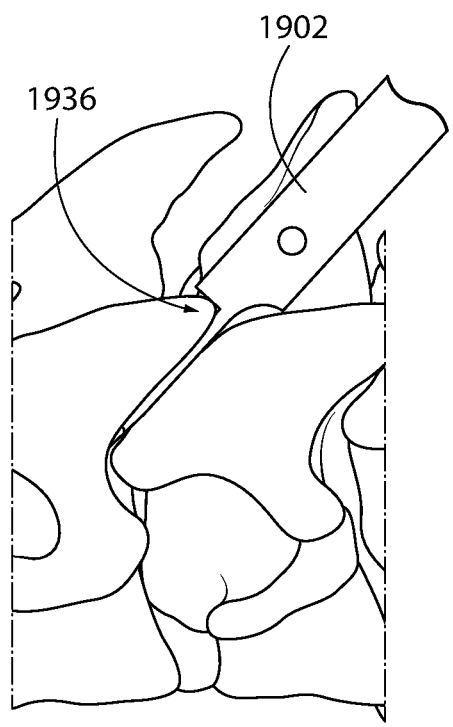
FIG. 53B is a side view of the access chisel of FIG. 53A positioned within the facet space or joint.

FIG. 53A is a side view of an embodiment of an access chisel 1902. FIG. 53B is a side view of the access chisel 1902 of FIG. 53A, shown positioned within the facet joint space. In some embodiments, the access chisel 1902 may include a hard stop feature 1936 on the proximal end of the tongue 1934. In some examples, the hard stop 1936 may be a flat ridge that is generally perpendicular to the tongue 1934. Similar to the scalloped feature 1836, the hard stop 1936 may be used to prevent the access chisel 1902 from advancing further into the facet joint and provide stabilization for medial/lateral movement for controlled and targeted decortication. In some examples, the access chisel 1902 may include a scalloped feature 1937 on the underside of the tongue. The scalloped feature may also act as a hard stop to help prevent the access chisel 1902 from advancing further into the facet joint and provide stabilization for medial/lateral movement for controlled and targeted decortication. The scalloped feature 1937 may extend past the hard stop 1936 in the direction of a proximal end of the access chisel 1902 such that a length of the side of the tongue with the scalloped features 1937 is longer than a length of the tongue with the hard stop 1936.

Figure 54:
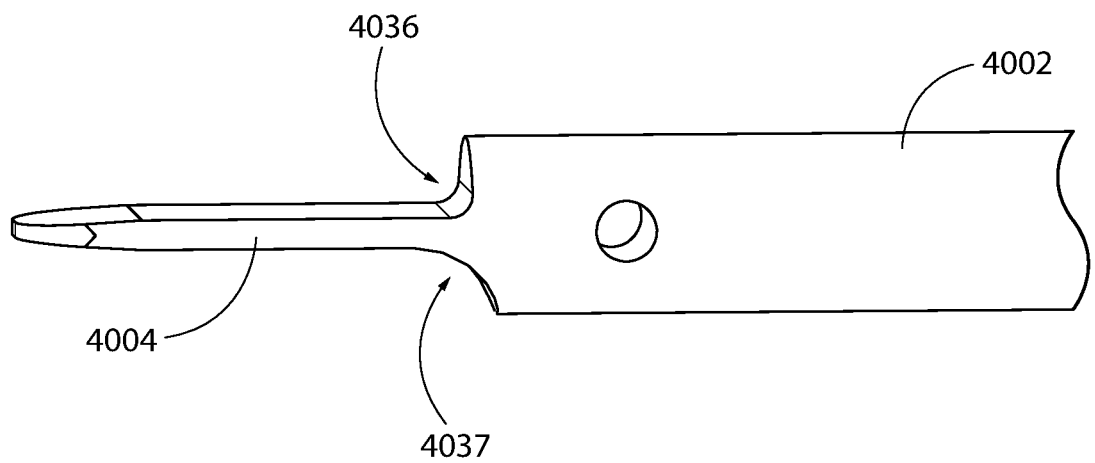
FIG. 54 is a perspective view of an embodiment of an access chisel.

FIG. 54 is a side view of an embodiment of an access chisel 4002. In some embodiments, the access chisel 4002 includes a hard stop feature 4036 on a proximal end of the tongue 4004. In some examples, the hard stop 4036 may be a flat ridge that is generally perpendicular to the tongue 4034. In some examples, the access chisel 4002 may also include a scalloped feature 4037 on the proximal end of the tongue 4004 on the underside of the tongue a side opposite that with the hard stop 4036. The overall length of the tongue of the side of the tongue with the scalloped feature 4307 may be generally the same as a length of the tongue with the hard stop 4036. In some examples, a length of the radius of the scalloped feature 1937 may larger than that of a length of the radius of the scalloped feature 4037, in some examples, to better match the geometry of the cervical spine.

FIG. 55A is a perspective view of an embodiment of an access chisel 2002. FIGS. 55B-55D are rear, side, and perspective views of the access chisel 1002 of FIG. 55A positioned within the facet joint space. The access chisel of FIGS. 55A-55D may include similar or different features, and be used in similar or different methods, than as previously described access chisels. The access chisel 2002 may include a blade 2038 that extends along the tongue 2034 and away from the upper surface of the tongue, between the hard stop feature 2036 and the chisel tip 2006. The blade 2038 may extend along the center or near the side of the tongue, being a raised feature that may dig into the underside of the superior facet when in use, providing greater stability and minimizing or preventing unwanted medial/lateral movement for improved controlled and targeted decortication. The distal end 2006 of the access chisel 2002 is shaped to have a wide nose, similar to access chisel 1702 of FIG. 47, but other shapes or types of noses may be used.

In some embodiments, the access chisel 2002 includes a vertical blade 2040 at the distal end of the chisel tip 2006, such as adjacent the hard stop 2036, that may dig into the superior facet entrance to provide additional stabilization for controlled and targeted decortication.

In some examples, such as the access chisel 1102 of FIG. 56, the area adjacent the hard stop may include a rasp texture 2138 instead of a vertical blade. While the chisel 2102 includes a chisel tip 2106 with a pointed nose, other nose shapes may be used.

The center blade can run the entire length of the tongue of the access chisel in various configurations. FIGS. 57A and 57B are top perspective and side views of an embodiment of an access chisel 2202, with the center blade 2238 extending along the length of the tongue 2234, between and including the scalloped feature 2236 to the chisel tip 2206. FIGS. 58A and 58B are a perspective and side view of an embodiment of an access chisel 2302, with the center blade 2338 extending along the tongue 2334 between the scalloped feature 2336 and the chisel tip 2306. As shown in FIGS. 58A and 58B, the scalloped feature 2336 does not include the center blade 2338 or a vertical blade. FIGS. 59A and 59B are a perspective and side view of an embodiment of an access chisel 2402, where the center blade 2438 extends along the tongue 2434 between and includes the hard stop feature 2436 to the chisel tip 2406. The hard stop feature 2436 may be similar to the hard stop feature 1936 of FIGS. 53A-53B, but may also include a tapered or angle face 2437 on the center blade at the hard stop. The access chisels of FIGS. 57A-57B may be similar to or different than, and used in similar or different manners, as previously described access chisels. While the chisel tips 2206, 2306, and 2406 of FIGS. 57A-59B are shown in a wide nose shape, other shapes and combinations of features may be used.

Figure 60:
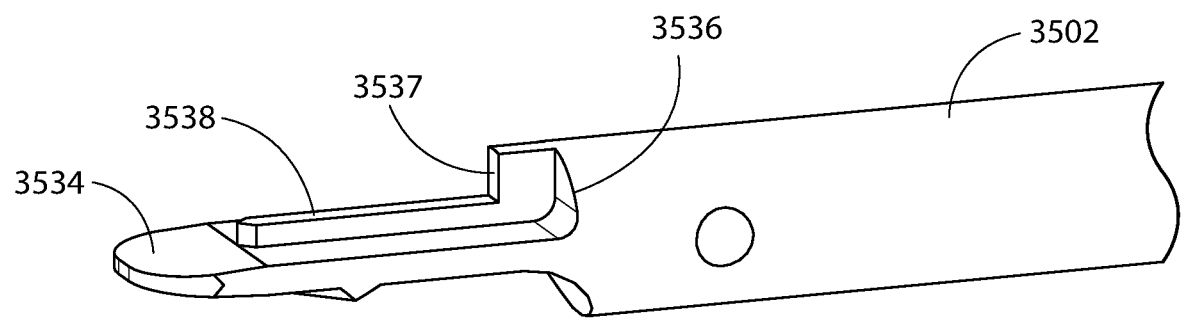
FIG. 60 is a perspective view of an embodiment of an access chisel.

FIG. 60 is a perspective view of an embodiment of an access chisel 3502, with the center blade 3538 extending along the length of the tongue 3534. The hard stop feature 3536 may include the center blade that extends upwards with a blunt or flat face 3537, as opposed to the tapered or pointed face of the stop 2436 of FIGS. 59A-59B.

Figure 61:
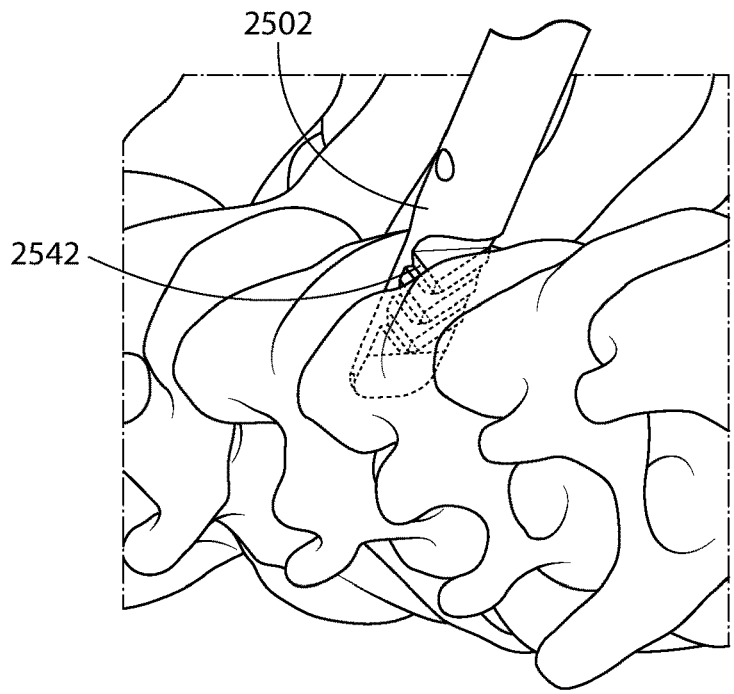
FIG. 61 is a perspective view of an embodiment of an access chisel positioned within the facet space.
Figure 62:
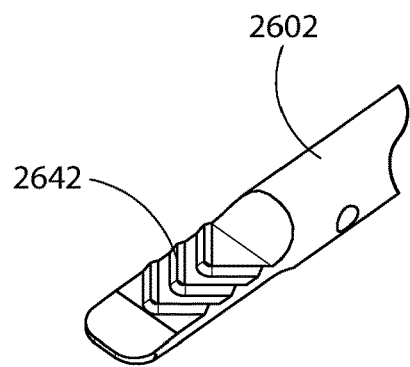
FIGS. 62-65 are perspective views of various embodiments of an access chisel.
Figure 63:
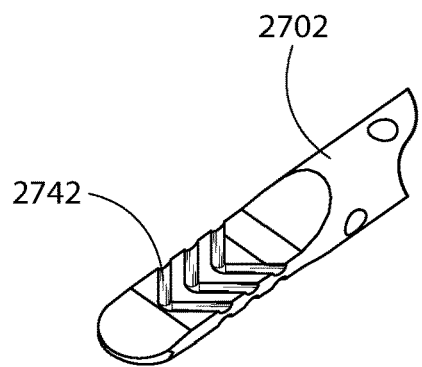
Figure 64:
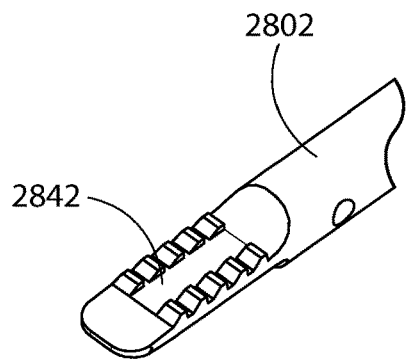
Figure 65:
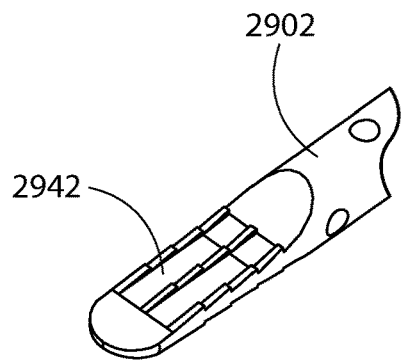
Figure 67:
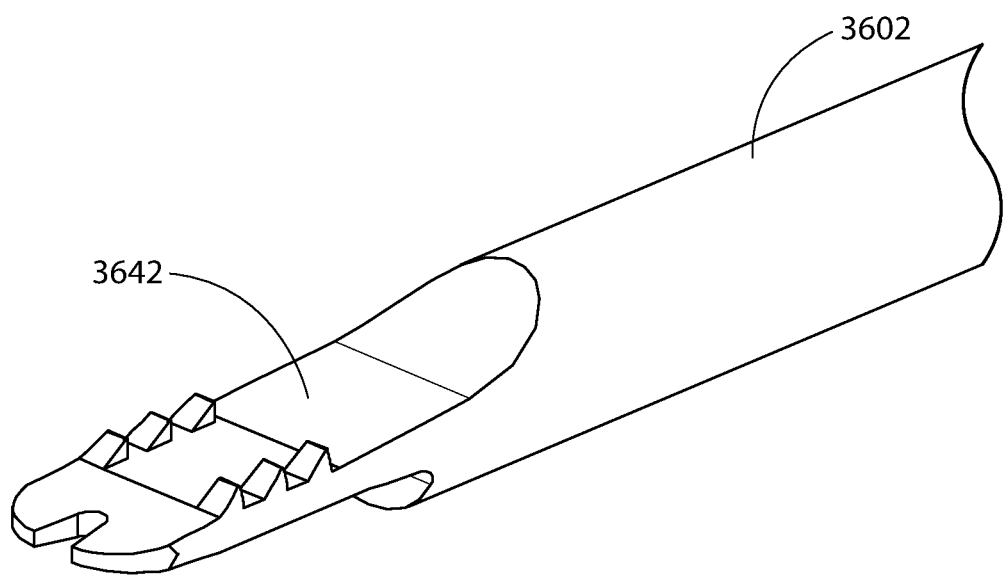
FIG. 67 is a perspective view of an embodiment of an access chisel.

In some examples, the underside of the access chisel tongue may include an anti-backout feature, such as raised or indented chevron profile, teeth, or another textured feature that may help prevent the access chisel from unintentional backout. FIG. 61 is a bottom perspective view of an embodiment of an access chisel 2502 positioned within the facet space, with the underside 2542 including a raised chevron pattern. FIGS. 62-65 are bottom perspective views of embodiments of access chisels 2602, 2702, 2802, 2902. The access chisels 2502, 2602, 2702, 2802 may include similar or different features, and be used in similar or different methods, than as previously described access chisels. FIG. 62 shows the bottom surface 2642 of access chisel 2602 that includes a raised chevron pattern. FIG. 63 shows the bottom surface 1742 of the tongue of access chisel 1702 that includes an indented or concave chevron pattern. FIG. 64 shows the bottom surface 2842 of the tongue of the access chisel 2802 that includes raised teeth positioned on either side edge of the tongue. The teeth of access chisel 2802 may have flatted areas at the top of each tooth, with two rows of teeth. FIG. 65 shows the bottom surface 2942 of the access chisel 1902 including teeth extending the length of the tongue in 3 rows. FIG. 67 is a perspective view of an embodiment of an access chisel 3602, with the bottom surface 3642 that includes raised teeth on either side edge of the tongue. The teeth of access chisel 3602 have pointed ends at the top of each tooth. In some examples, each row of teeth may include one, two, three, four, five, size, seven, eight, nine and/or ten teeth. In some examples, the access chisel may include one, two, three, four, five, size, seven, eight, nine and/or ten rows of teeth. In some examples, the rows of teeth include the same or similar numbers of teeth, or different numbers of teeth. In some examples, a first row may include more or less teeth than that of a second, third, fourth, fifth, sixth, seventh, eighth, ninth or tenth row of teeth.

Various combinations of the underside surface treatments or features may be used. The underside surface features may also act as a stabilization feature to provide further stabilization in the medial/lateral movement and/or in conjunction with the center blade feature for improved controlled and targeted decortication. The access chisels of FIGS. 61-65 and 67 may be similar to or different than, and used in similar or different manners, as previously described access chisels.

Figure 68A:
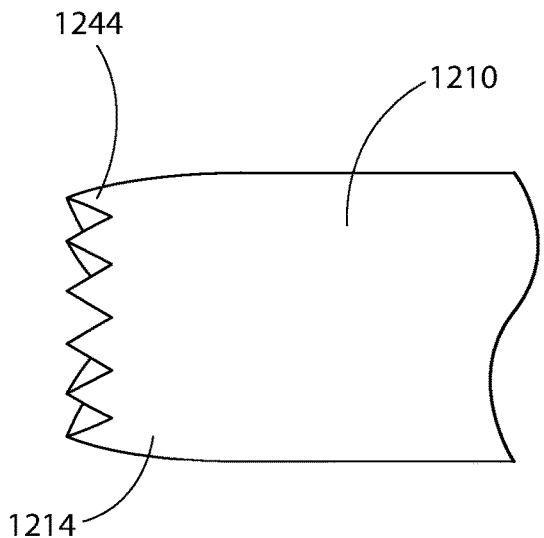
FIGS. 68A-68B are a side and perspective view of an embodiment of an outer decorticator.
Figure 68B:
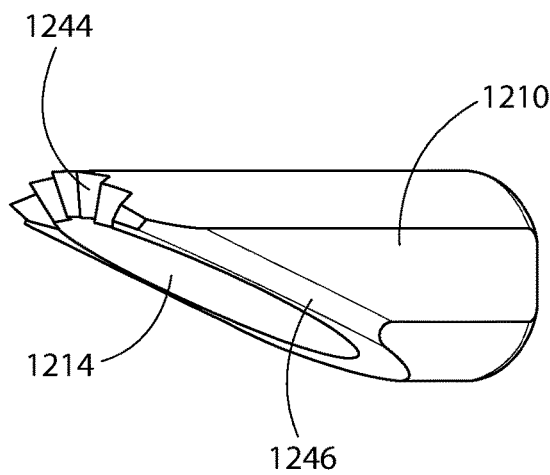
Figure 69A:
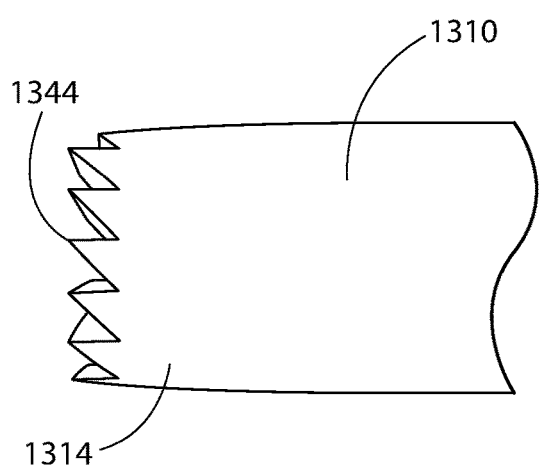
FIGS. 69A-69B are a side and perspective view of an embodiment of an outer decorticator.
Figure 69B:
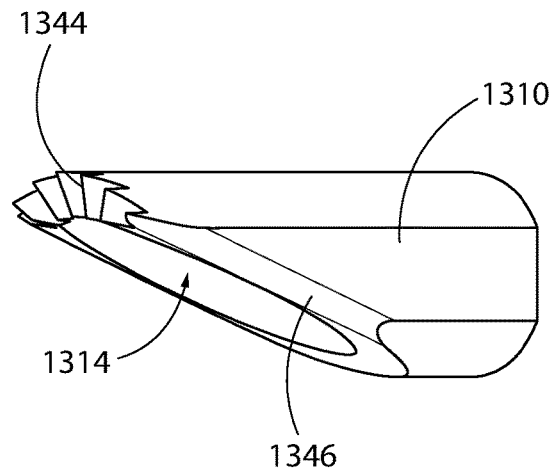
Figure 70A:
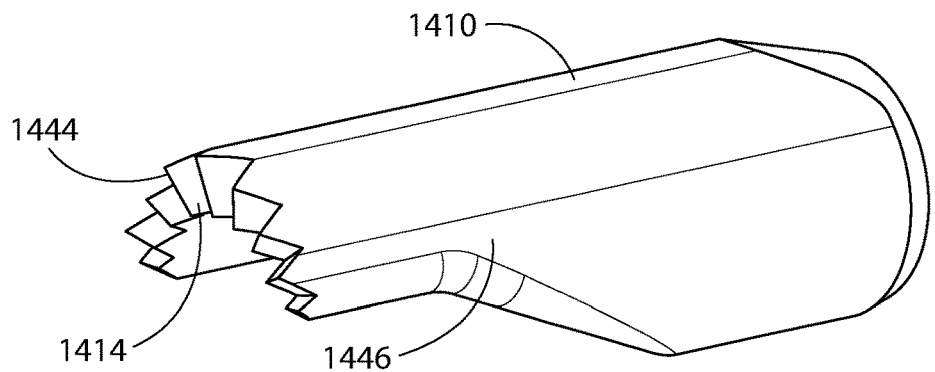
FIGS. 70A-70C are various views of an embodiment of an outer decorticator.
Figure 70B:
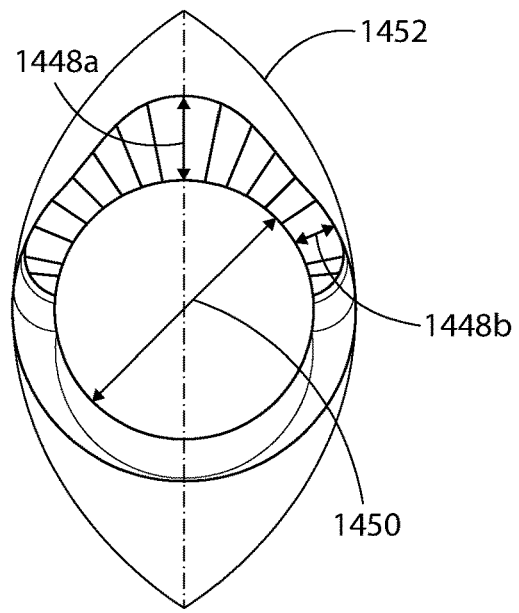
Figure 70C:
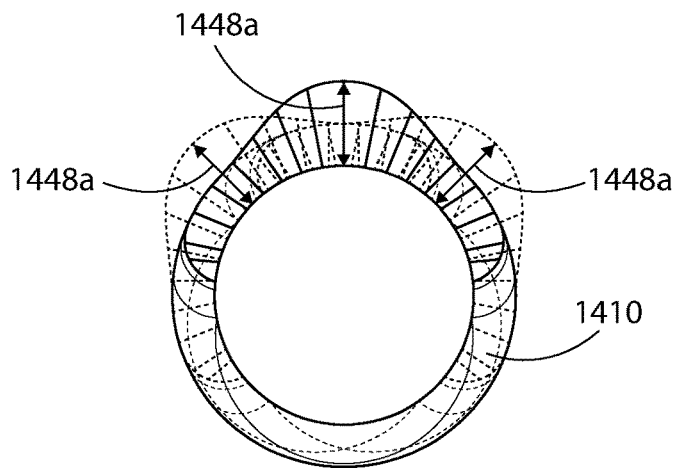

Various features and embodiments of outer decorticators similar to or different than outer decorticator 110 are now described. FIGS. 68A-68B are side and perspective views of an embodiment of an outer decorticator 1210. FIGS. 69A-69B are side and perspective views of an embodiment of an outer decorticator 1310. FIGS. 70A-70C are perspective and distal views of an embodiment of an outer decorticator 1410. The outer decorticator 1210, 1310, 1410 may include similar or different features, and be used in similar or different methods, than as previously described outer decorticators. Outer decorticator 1210, 1310 may include a chamfered distal end 1214, 1314 with a plurality of serrated teeth 1244, 1344 positioned at the distal tip of the chamfered distal end 1214, 1314 and a beveled edge 1246, 1346 extending along the periphery of the chamfered distal end. In some embodiments, the teeth 1244 are bidirectional, and the teeth 1344 are unidirectional. The width of the teeth at the base of each tooth may be in a range between and including 1-3 mm. In use, the outer decorticator is advanced over the access chisel to dissect fascia and muscle off the lateral lamina and lateral mass under visual guidance. The larger size of the distal end 1214, 1314 may allow a larger area to be dissected.

The outer decorticator 1410 may include a chamfered distal end 1414, with a plurality of serrated teeth 1444 and a beveled edge 1446 extending along the periphery of the chamfered distal end 1414. In some examples, the chamfered portion of the distal end is offset away from the portion of decorticator 1410 formed by the teeth. With reference to FIG. 70B, the lumen forming the internal portion of the distal end 1414 may have a generally constant diameter 1450. The outer surface of the decorticator 1410 may have a cam lobe type shape, with a bump or raised portion in one section. The cam shape may be attributed to a varying height 1448 of each tooth 1444, with the tooth at a center of the toothed section having a taller height 1448a than the height 1448b of the teeth at the edges of the toothed section. The overall shape of the decorticator 1410 may be optimized to increase the reach of the decorticator teeth 1444 while optimizing insertion through a small incision 1452, such as a vertical incision, made using a scalpel. As shown in FIG. 70C, the outer decorticator tip may be rotated back and forth in the direction of the arrow, allowing the tooth with the tallest height 1448a to reach and decorticate bone while maintaining ease of insertion through the vertical incision. In some examples, the height 1448a of the tallest tooth may be approximately 2 mm, but a smaller or larger height tooth may also be used.

Various features and embodiments of guide tubes similar to or different than guide tube 118 are now described. The following guide tubes may include similar or different features, and be used in similar or different methods, than as previously described guide tubes.

Figure 71A:
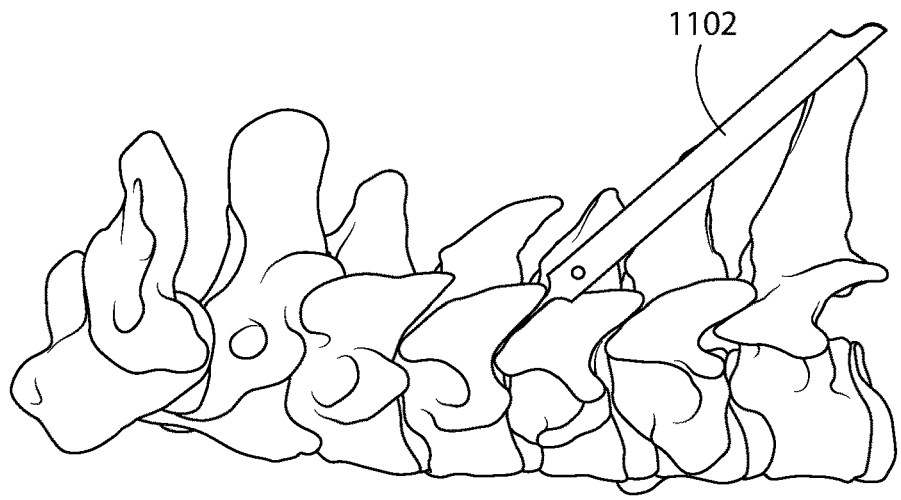
FIG. 71A is a side view of a delivery tool assembly including an embodiment of an access chisel introduced into a facet space.

FIGS. 71A-71E show views of a delivery tool assembly including a guide tube being docked to or positioned within a facet joint. FIG. 71A is a side view of a delivery tool assembly including an embodiment of an access chisel 1102 introduced into a facet joint space. In use, the access chisel is first introduced to the surgical site and inserted into the articular capsule of the facet joint.

Figure 71B:
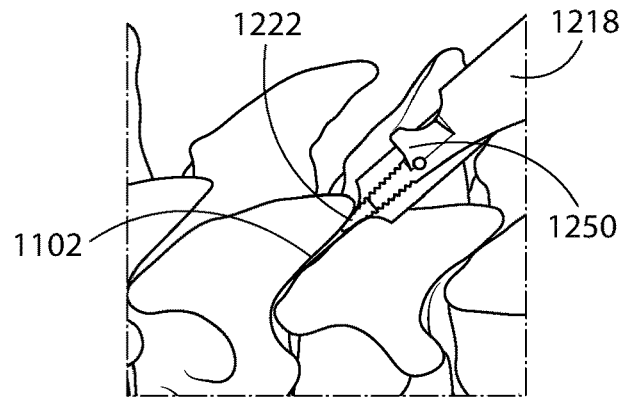
FIG. 71B is a side view the delivery tool assembly of FIG. 71A including an embodiment of a guide tube and the access chisel being introduced into the facet space.
Figure 71C:
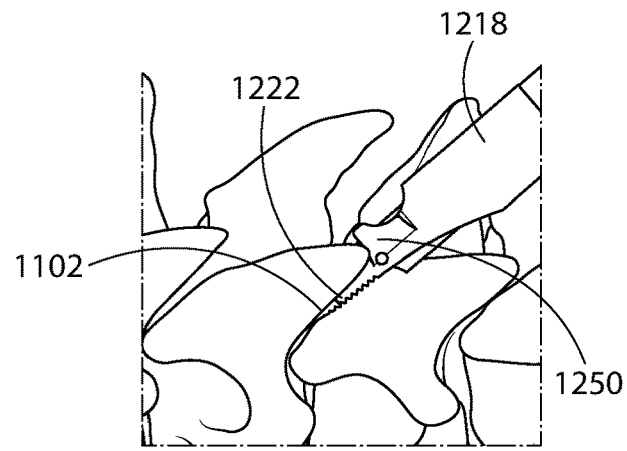
FIG. 71C is a side view of the delivery tool assembly of FIG. 71B with the access chisel received in the guide tube and positioned within the facet space.

FIG. 71B is a side view the delivery tool assembly of FIG. 71A including an embodiment of a guide tube 1218 sleeved over the access chisel and being introduced into the facet joint space. The guide tube 1218 slides over the access chisel 1102 as a guide and is positioned at the entry point of the facet joint with the hard stop 1250 of the guide tube 1218 facing posteriorly. FIG. 71C is a side view of the delivery tool assembly of FIG. 71B with the guide tube 1218 sleeved over the access chisel 1102 and positioned within the facet joint space, with the forks 1222 of the guide tube 1218 extending on either side of the access chisel 1102. In use, the guide tube 1218 may be malleted to insert the forks 1222 into the articular capsule. The physical hard stop 1250 may help to prevent the tip and forks 1222 from being inserted too anteriorly.

Figure 71D:
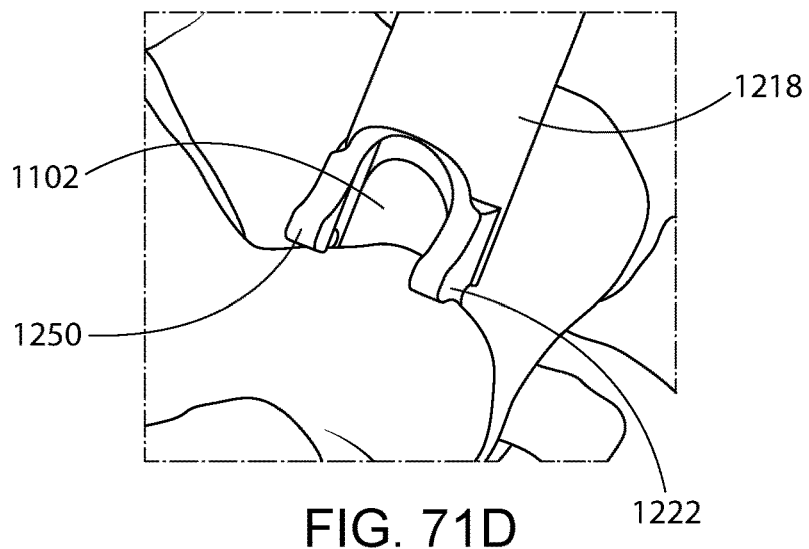
FIG. 71D is a perspective view of the delivery tool assembly of FIG. 71C positioned within the facet space.
Figure 71E:
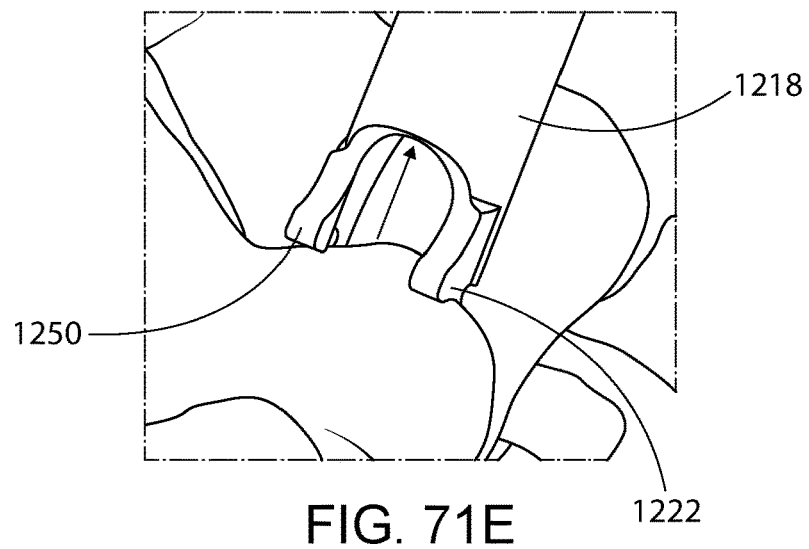
FIG. 71E is a perspective view of the delivery tool assembly of FIG. 71D with the access chisel removed.

FIG. 71D is a perspective view of the delivery tool assembly of FIG. 71C positioned within the facet joint space. FIG. 71E is a perspective view of the delivery tool assembly of FIG. 71D with the access chisel removed. The tip and forks 1222 of the guide tube 1218 further distracts the joint which may allow the access chisel 1102 to be removed from the joint.

Figure 71F:
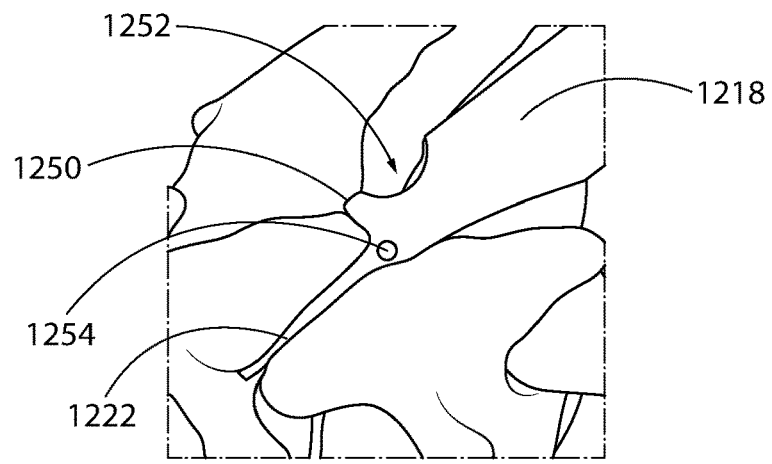
FIG. 71F is a side view of the delivery tool assembly of FIG. 71E.

FIG. 71F is a side view of the delivery tool assembly of FIG. 71E, showing the curve feature 1252 and visualization hole 1254 positioned on the distal end 1214 of the guide tube 1218. In some examples, the curve or arcuate shaped cut-out or feature 1252, located proximal to the hard stop 1250, and the visualization hole 1254 may provide a visualization landmark for the user to position the tip or distal end of the guide tube properly in the facet joint. In some examples, the curve feature may be a rounded, scalloped, arcuate or concave shaped cutout.

Figure 72:
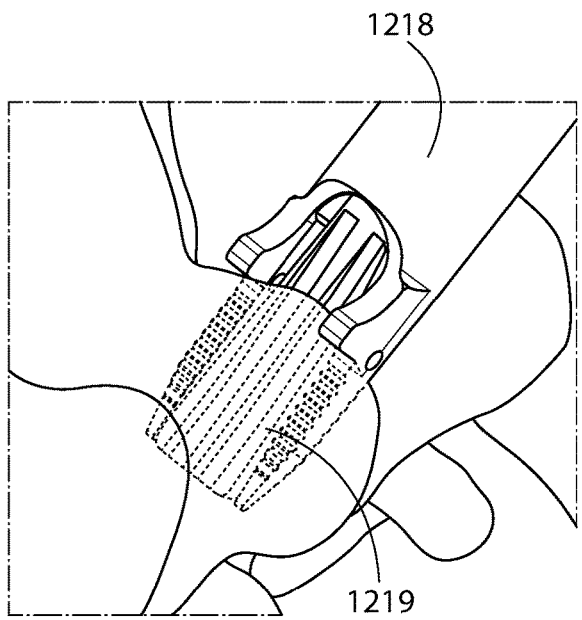
FIG. 72 is a perspective view of a guide tube with a decortication rasp received within the guide tube.
Figure 73:
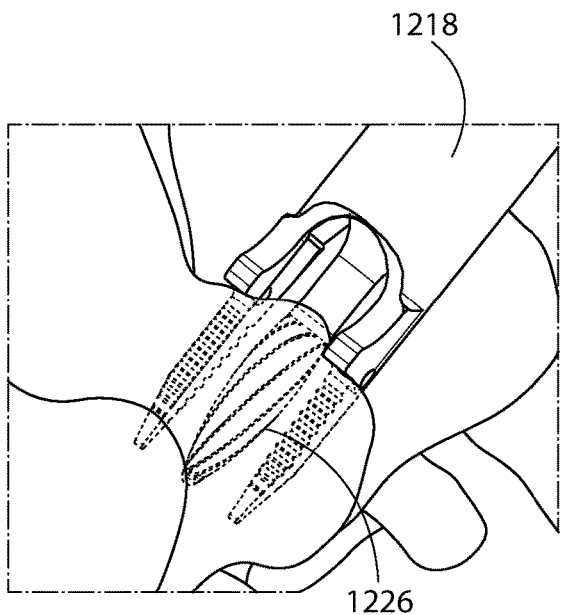
FIG. 73 is a perspective view of a guide tube with a decortication burr received within the guide tube.
Figure 74:
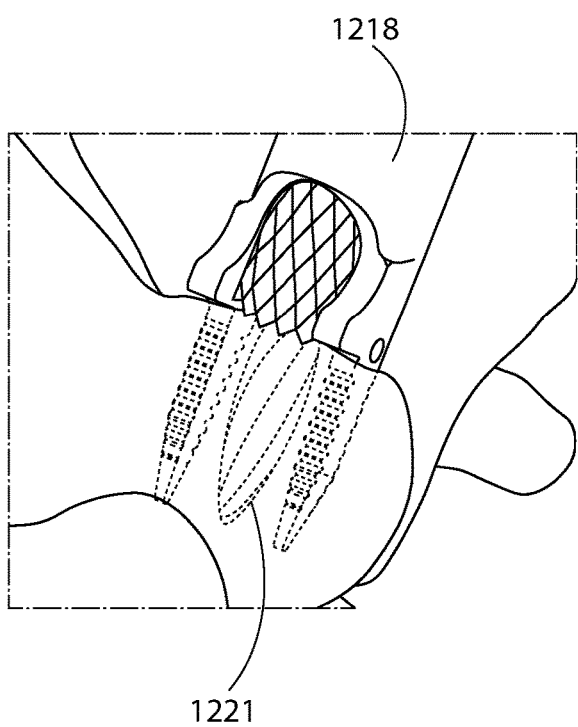
FIG. 74 is a perspective view of a guide tube with an interior facet decorticator sleeved within the guide tube.
Figure 75:
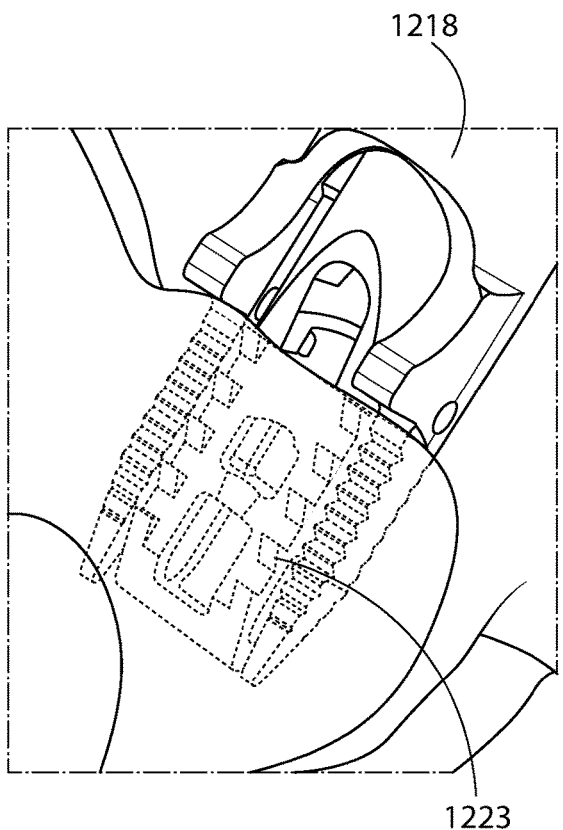
FIG. 75 is a perspective view of a guide tube with an intervertebral cage implant being delivered through the guide tube into the facet joint.

In some examples, including FIGS. 72-75, the docked guide tube 1218 can be used as a working cannula for various decortication instruments to prepare the articular surfaces for implant insertion. FIG. 72 is a perspective view of docked guide tube 1218 with a decortication rasp 1219 sleeved within the guide tube. FIG. 73 is a perspective view of docked guide tube 1218 with a decortication burr 1126 sleeved or positioned within the guide tube. FIG. 74 is a perspective view of docked guide tube 1218 with an inferior facet decorticator 1121 sleeved within the guide tube 1218. In use, the inferior facet decorticator 1121 may decorticate the interarticular surfaces of the facet joint. FIG. 75 is a perspective view of docked guide tube 1218 with an intervertebral cage implant 1123 sleeved or positioned within the guide tube. In some examples, after the interar-ticular surfaces of the facet joint have been decorticated, the intervertebral cage implant 1123 can be inserted through the guide tube and fixated into the facet joint.

Figure 76:
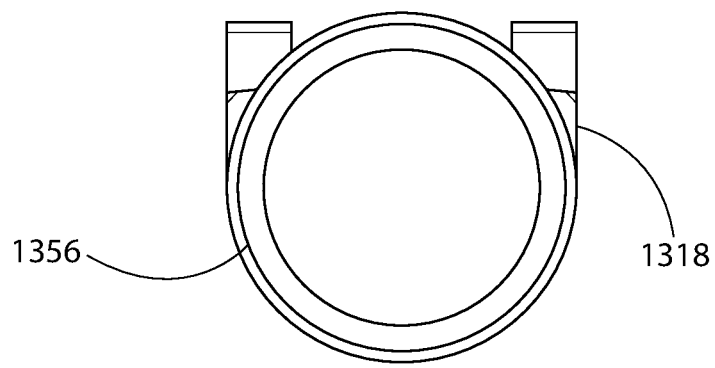
FIGS. 76-78 are proximal end views of various embodiments of a guide tube.
Figure 77:
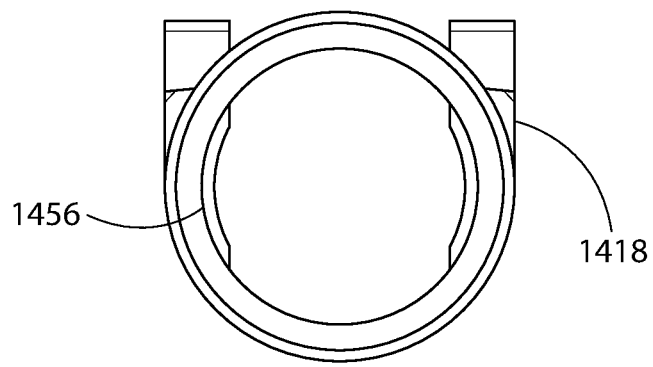
Figure 78:
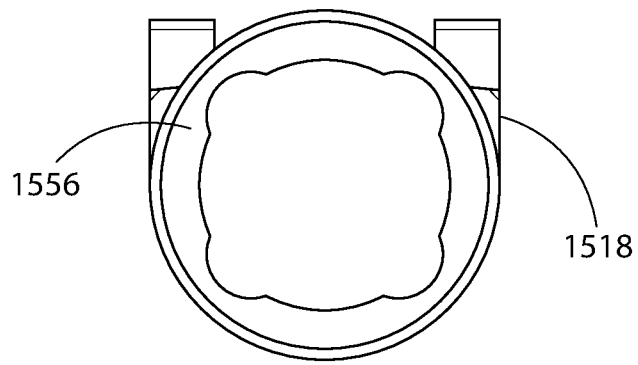

FIGS. 76-78 are proximal end views of embodiments of a guide tube. The guide tubes 1318, 1418, 1518 of FIGS. 76-78 may be similar to or different than, and used in similar or different manners, as previously described guide tubes. In some examples, the working cannula formed through the body the guide tube tip may have various profiles to accommodate multiple instruments of the system. FIG. 76 shows a guide tube 1318 with a tip having a working cannula 1356 with a center hole. FIG. 77 shows a guide tube 1418 with a tip having a working cannula 1456 with a concentric holes. FIG. 78 shows a guide tube 1518 with a tip having a working cannula 1556 with a four corner cutout. The various working cannula shapes 1356, 1456, 1556 may allow a variety of instruments to be used in conjunction with the guide tube.

Figure 79:
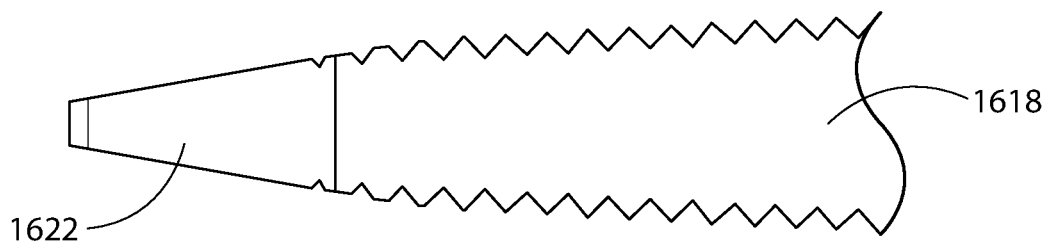
FIGS. 79-80 are side views of the distal ends of embodiments of a guide tube.
Figure 80:
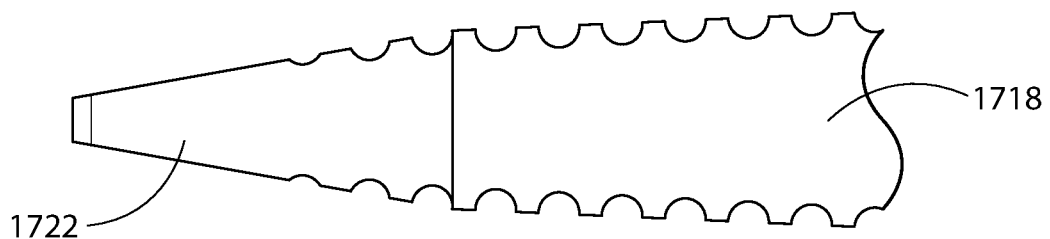
Figure 82:
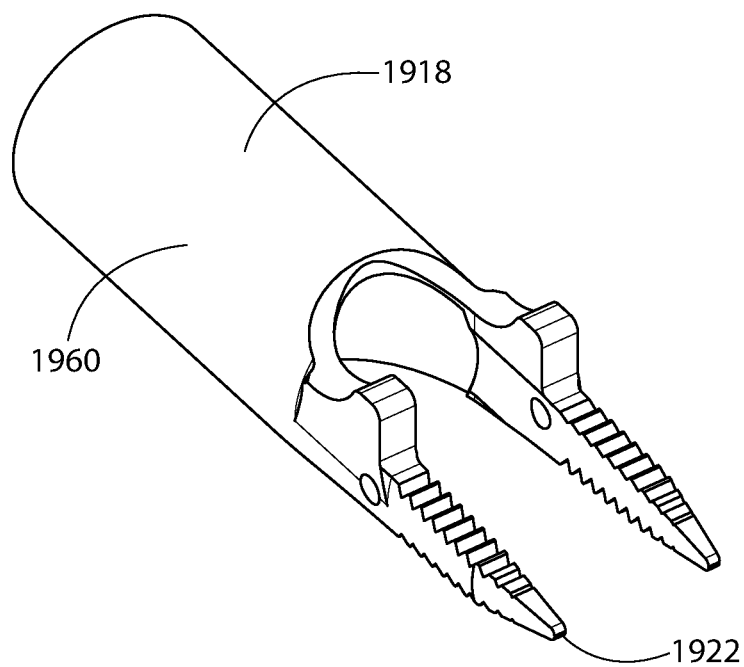
FIGS. 82-84 are perspective views of the distal ends of embodiments of a guide tube.
Figure 83:
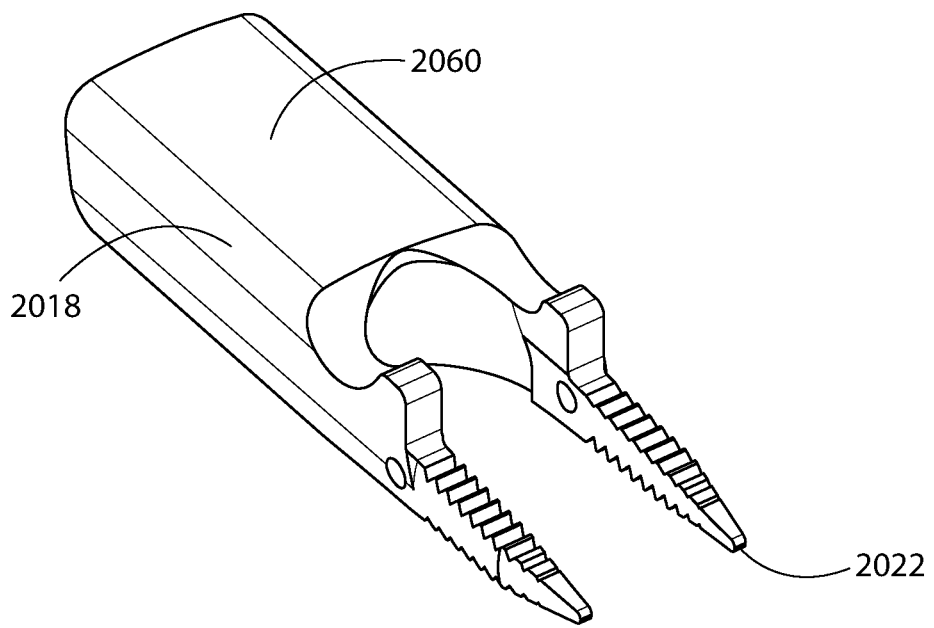
Figure 84:
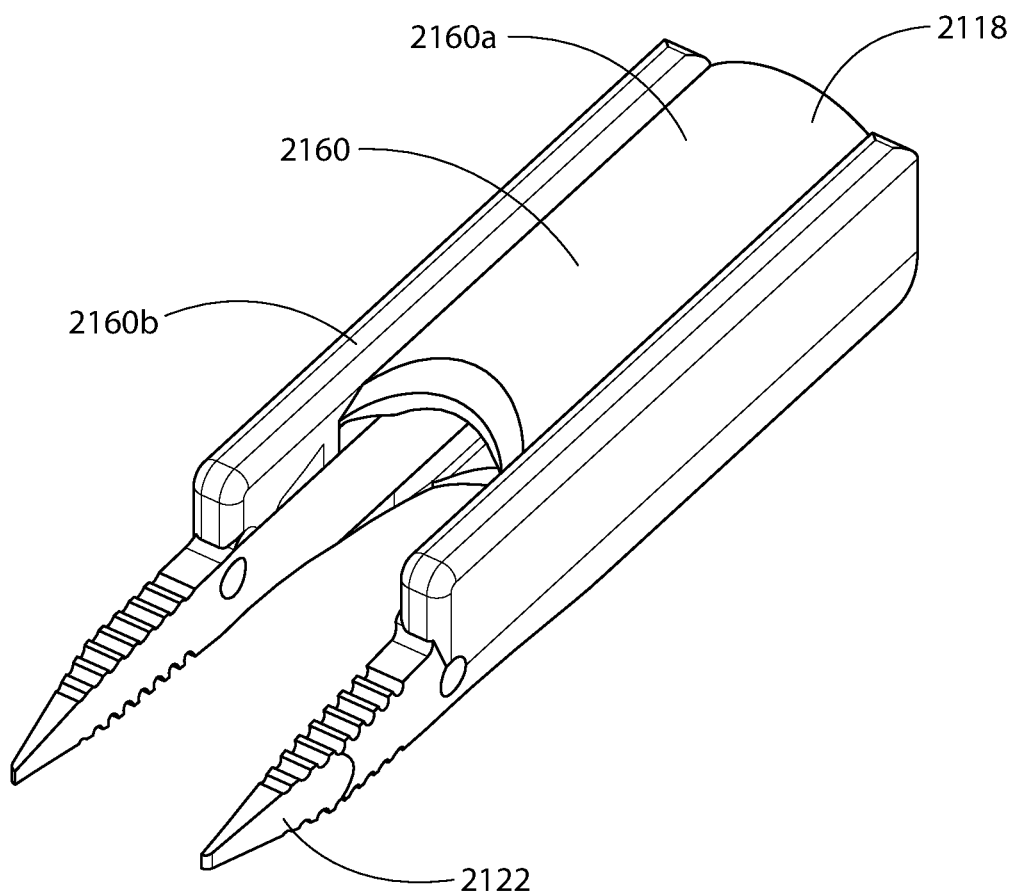

FIGS. 79-80 are side views of the distal ends of guide tube embodiments. FIGS. 82-84 are perspective views of the distal ends of guide tube embodiments. In some embodiments, guide tube 1618 may have a guide tube tip 1622 with teeth formed with a "V" profile (FIG. 79) or guide tube 1718 may have a guide tube tip 1722 with teeth formed with a "U" profile (FIG. 80). The various shapes of the teeth on the tip 1622, 1722 may help to anchor the tip into the articular surfaces of the joint to prevent instrument back-out.

Figure 81A:
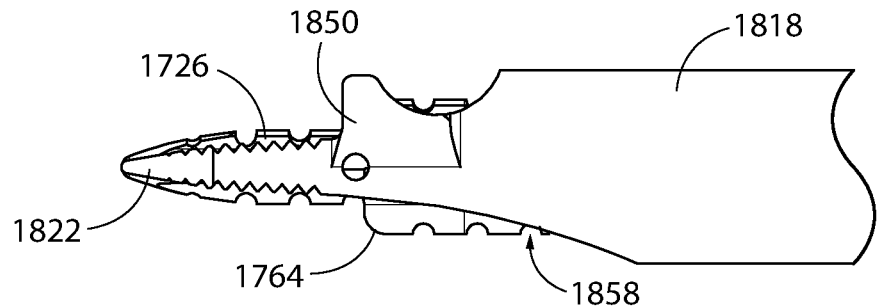
FIGS. 81A-81C are various views of the distal ends of embodiments of a guide tube and a decorticating burr.
Figure 81B:
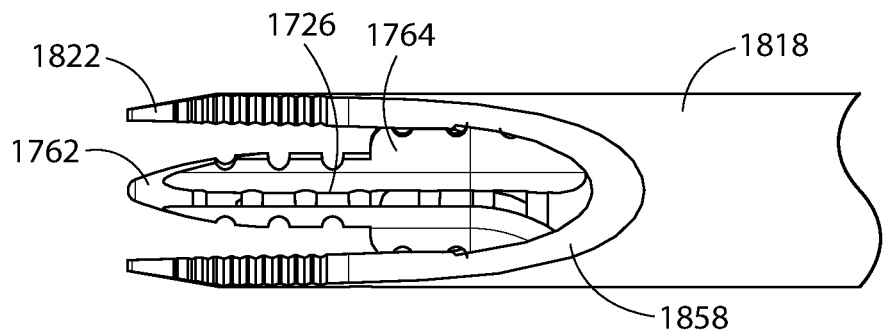
Figure 81C:
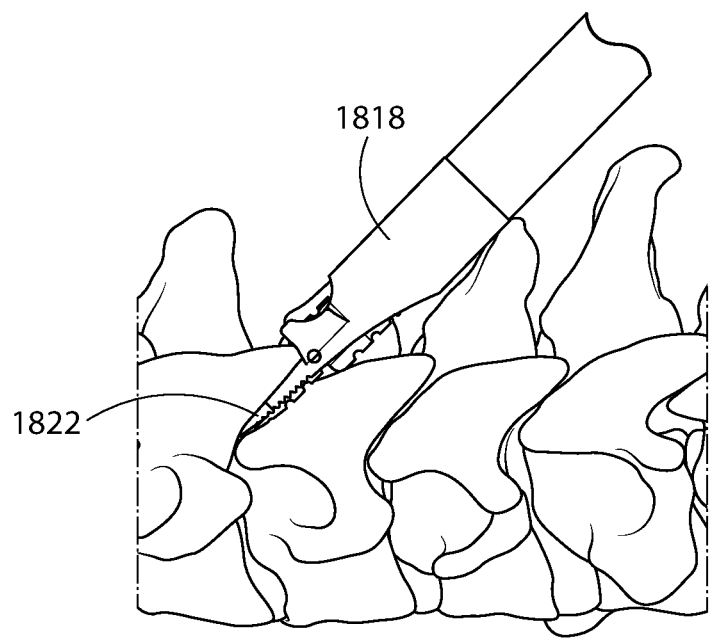

FIG. 81A-81C show the tip 1822 of guide tube 1818 and a decorticator burr 1726 having a first or intra facet burr 1762 and a second or outer facet burr 1764. In some examples, the inner decorticator or decorticator burr is used in combination with the guide tube. In some examples, the underside of the guide tube tip 1822 may include a large lower cutout or scallop feature 1858 to help expose a decorticator tool, such as a decorticator burr 1726, to be able to decorticate areas outside of or adjacent the facet joint. Compared with other guide tube embodiments, the length of the lower radius of the cutout 1858 is increased to, in some examples, better match the geometry of the cervical spine and to help expose more of the inner decorticator cutting surface. The guide tube tip may also include a guide tube tip bump or hard stop 850 to help maintain or control the position of the distal end of the guide tube.

The guide tube may act as a portal to allow the inner decorticator to insert through it and reach the desired space (See FIG. 81C, with the distal ends of the tools positioned within the facet space). In use, the guide tube 1818 is inserted posteriorly into a facet joint into the cervical spine (C1-C7/T1). The decorticator burr, such as decorticator 1726, is inserted through the guide tube. Once it reaches the facet space, it is rotated to decorticate the bone. The guide tube may act as a hard stop for the inner decorticator, preventing it from being inserted too deeply. When fully inserted, the tip of the intra facet burr 1762 aligns with the front tip 1822 of the guide tube 1818. As shown in the top view FIG. 81B, the front edge of the outer facet burr 1764 can be offset behind the front edge of the guide tube tip bumps or hard stop 1850 to prevent over decortication when rotating the decorticator. The front edge of the outer facet burr 1764 may line up with or be parallel to the front edge of the guide tube tip bumps or hard stop 1850, allowing the front face to the facet to be decorticated.

In some examples, the outer profile of the guide tip may have a different shape in order to adjust the thickness and geometry of the hard stops and forks of the guide tube. FIG. 82 shows the tip 1922 of guide tube 1918 which includes an outer profile 1960 that is circular. FIG. 83 shows the tip 2022 of guide tube 2018 which includes a rectangular outer profile 2060. FIG. 84 shows the tip 2122 of guide tube 2118 which includes an outer profile 2160 with a central portion 2160a that is circular and an outer portion 2160b that is rectangular.

Figure 85:
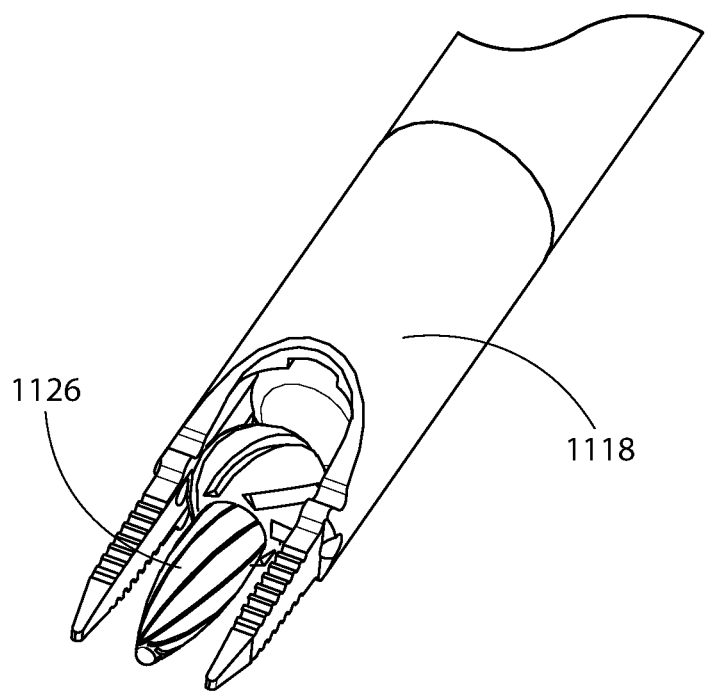
FIG. 85 is a perspective view of an embodiment of a delivery tool assembly including a guide tube and a decorticating burr.

Various features and embodiments of a decorticating burr similar to or different than decorticator burr 126 are now described. FIG. 85 is a perspective view of an embodiment of a delivery tool assembly including a guide tube and a decorticating burr. In use, the guide tube 1118 is inserted posteriorly into a facet joint in the cervical spine, such as at C1-C7/T1, preferably at C5-C7/T1. The decorticating burr 1126 or similar tool is inserted through the lumen of the guide tube 1118. Once the distal end 130 reaches the facet space, the decorticator burr 1126 may be rotated within the guide tube 1118 to decorticate the bony surface of the vertebrae that form the facet joint.

Figure 86:
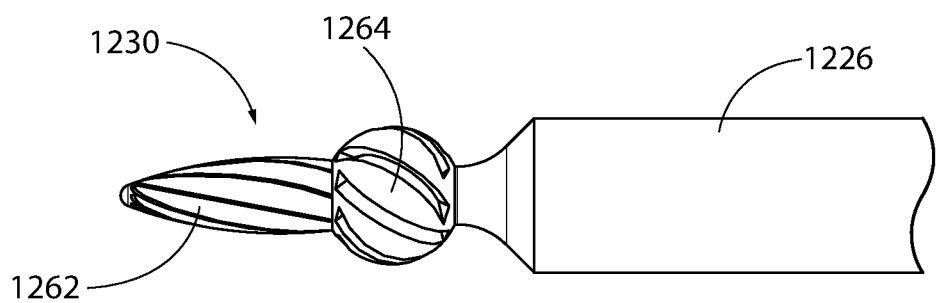
FIGS. 86-87 are side views of the proximal ends of embodiments of decorticating burrs.
Figure 87:
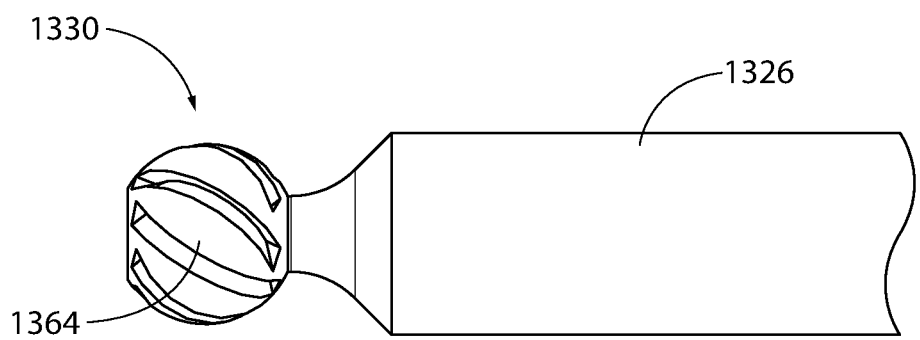

Embodiments of decorticator burr tools may include multiple geometry shapes, including a combination of two burr geometries. FIGS. 86-87 are side views of the proximal ends of embodiments of decorticating burrs.

As shown in FIG. 86, in some embodiments, the burred end 1230 of the decorticator burr 1226 may include a front, smaller outer diameter burr 1262 that may be inserted into the facet joint to decorticate inside the facet space. In some examples, the burr 1262 may be pointed or oval shaped, with a longer length than overall diameter, or a prolate spheroid, or a tapered oval shaped burr. An additional, larger diameter burr 1264 may be located proximal to the burr 1262, having a larger overall diameter than the diameter of the burr 1262. In some examples, the burr 1264 may sit outside the facet joint to decorticate the space outside the facet.

In some examples, the decorticator burr 1326 in FIG. 87 may include a single burr 1364 at the distal end 1330, the burr 1364 having a generally round or spherical shape. In use, the burr 1364 decorticates the space outside the facet joint.

Figure 88A:
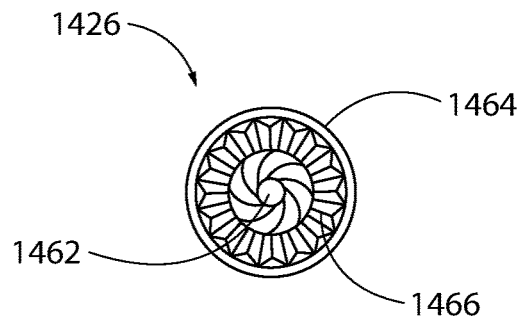
FIGS. 88A-88D are various views of an embodiment of a delivery tool assembly including a decorticating burr and guide tube.
Figure 88B:
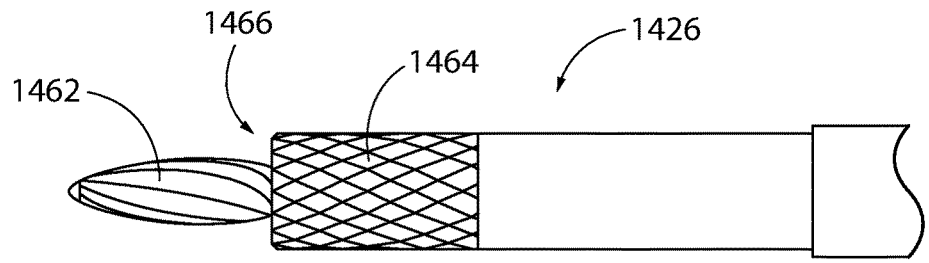
Figure 88C:
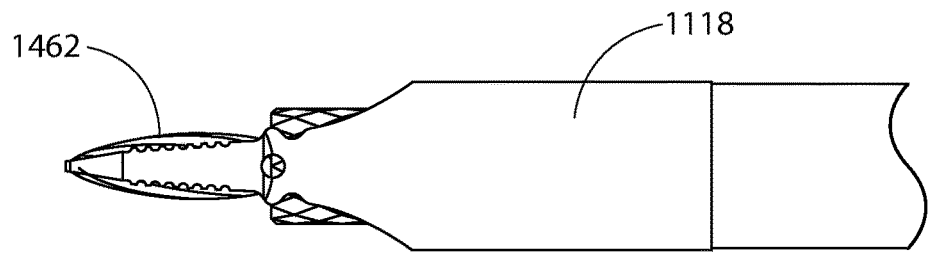
Figure 88D:
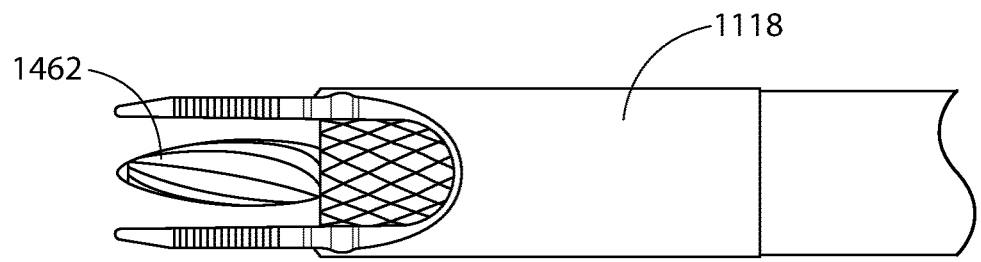

FIGS. 88A-88D are views of an embodiment of a delivery tool assembly including a decorticating burr 1426 and guide tube 1118. FIGS. 88A and 88B show a distal end view and side view of the decorticator burr 1426. FIGS. 88C and 88D show a side view and a top view of the delivery tool assembly including the decorticator burr 1426 and guide tube 1118, with the decorticator burr 1426 positioned within the guide tube 1118.

The decorticator burr 1426 includes a distal end formed by a prolate spheroid or a tapered oval shaped burr 1462 with a pointed end with angled cutting flutes. In some examples, the burr 1462 may have a bullet, snub-nosed, blunt, or flat end. In some examples, the burr 1462 may be cylindrical, or have a consistent cross-sectional area along the length of the burr. The decorticator burr 1426 may also include a burr 1464 positioned proximal to the burr 1462. The burr 1464 may be cylindrical shaped, with an angled, cross-hatched, bi-directional cutting flutes, or combinations thereof. A forward face 1466 of the burr 1464, located on a distal end of the burr 1464, may also include a cutting flute. In some examples, the forward face does not include a cutting burr.

Figure 89A:
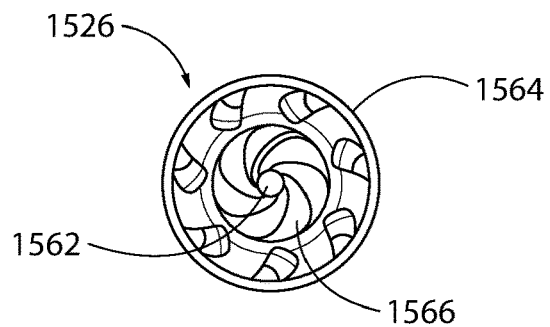
FIGS. 89A-89D are various views of an embodiment of a delivery tool assembly including a decorticating burr and guide tube.
Figure 89B:
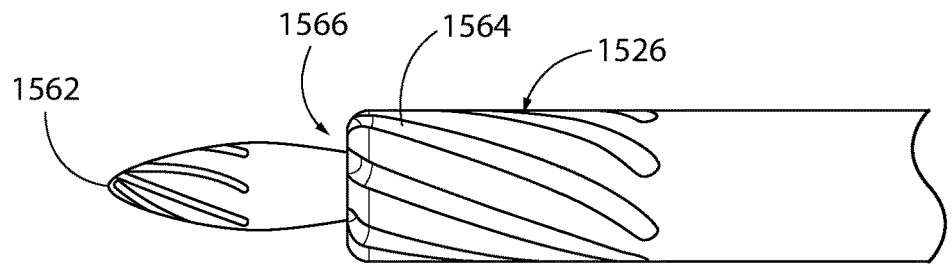
Figure 89C:
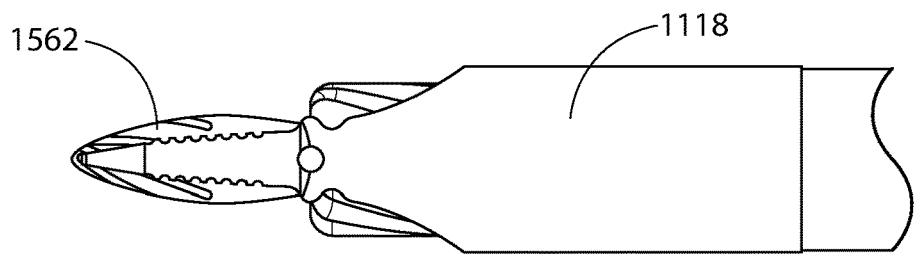
Figure 89D:
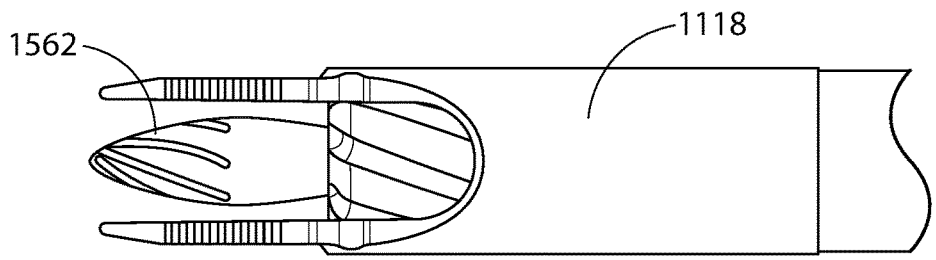

FIGS. 89A-89D are views of an embodiment of a delivery tool assembly including a decorticating burr 1526 and guide tube 1118. FIGS. 89A and 89B show a distal end view and side view of the decorticator burr 1526. FIGS. 89C and 89D show a side view and a top view of the delivery tool assembly including the decorticator burr 1526 and guide tube 1118, with the decorticator burr 1526 positioned within the guide tube 1118.

The decorticator burr 1526 includes a distal end formed by a prolate spheroid or a tapered oval shaped burr 1562 with a pointed end. In some examples, the burr 1562 may have a bullet, snub-nosed, blunt, or flat end. In some examples, the burr may be cylindrical, or have a consistent cross-sectional area along the length of the burr 1562. The angled, unidirectional flutes of burr 1562 may extend at least partially along the length of the burr 1562, but in some examples, may extend the full length of the burr (See FIG. 88B). The burr 1562 may be an intra facet decorticator that is used to decorticate inside the facet space.

The decorticator burr 1526 may also include a burr 1564 positioned proximal to the burr 1562. The burr 1564 may be cylindrical shaped, with angled, uni-directional cutting flutes. A forward face 1566 of the burr 1564, located at a distal end of the burr 1564, may also include a uni-directional cutting flutes. In some examples, the forward face 1566 does not include a cutting burr. In some examples, the burr 1564 includes a fluted design with six, or more or less, cutting flutes designed to decorticate bone. The flutes are helical and may help to drive the device into the bony space as it is rotated.

Figure 90A:
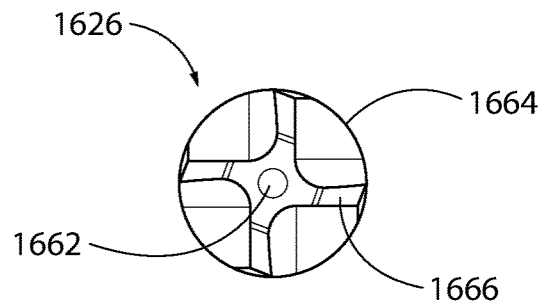
FIGS. 90A-90D are various views of an embodiment of a delivery tool assembly including a decorticating burr and guide tube.
Figure 90B:
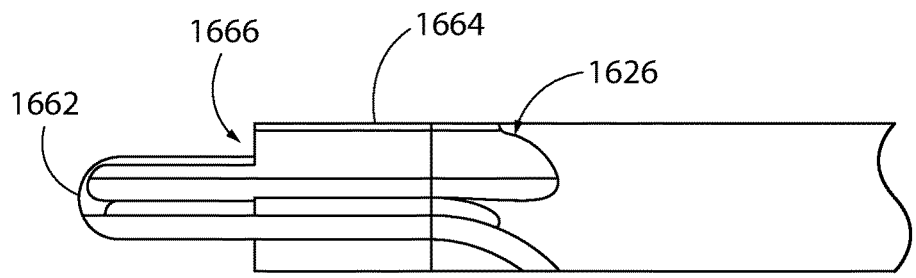
Figure 90C:
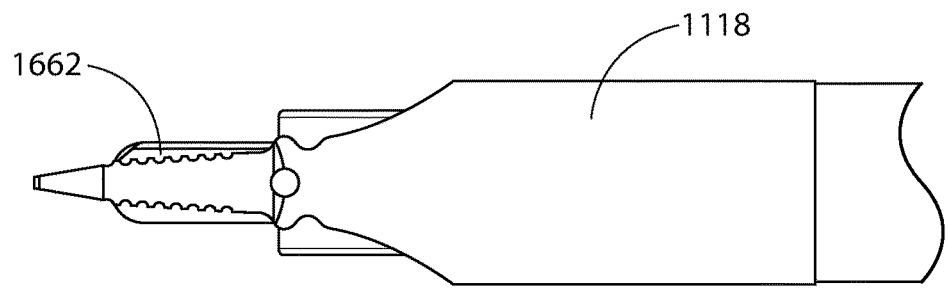
Figure 90D:
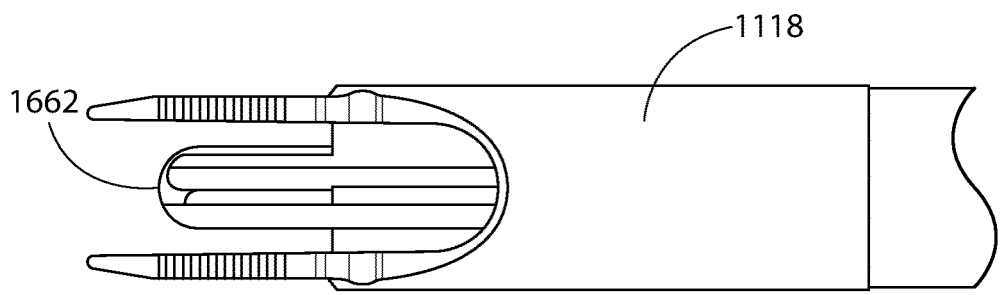

FIGS. 90A-90D are views of an embodiment of a delivery tool assembly including a decorticating burr 1626 and guide tube 1118. FIGS. 90A and 90B show a distal end view and side view of the decorticator burr 1626. FIGS. 90C and 90D show a side view and a top view of the delivery tool assembly including the decorticator burr 1626 and guide tube 1118, with the decorticator burr 1626 positioned within the guide tube 1118.

The decorticator burr 1626 includes a distal end formed by a snub nosed or bull nosed burr 1662. The burr 1626 is cylindrical, or has a consistent cross-sectional area along the length of the burr 1662 except for the distal end. The unidirectional flutes of burr 1662 may extend the length of the burr 1662. The unidirectional flutes on the burr 1662 may be used to decorticate the bony surface when rotated in a clockwise direction.

The decorticator burr 1626 may also include a burr 1664 positioned proximal to the burr 1662, so that the combination of burr 1662 and burr 1664 form a step drill. The burr 1664 may be cylindrical shaped, with a uni-directional cutting flutes similar to those of burr 1662. In some examples, the cutting flutes on the burr 1664 may be angled at a proximal end of the burr 1664. The angle of the flutes or cutting surfaces may be in between and including 10 and 25 degrees. A forward face 1666 of the burr 1664 may also include a uni-directional cutting flutes.

Figure 91A:
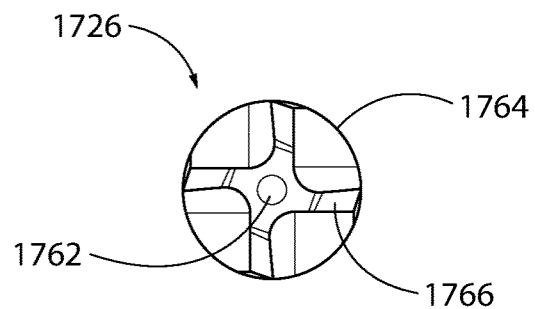
FIGS. 91A-91D are various views of an embodiment of a delivery tool assembly including a decorticating burr and guide tube.
Figure 91B:
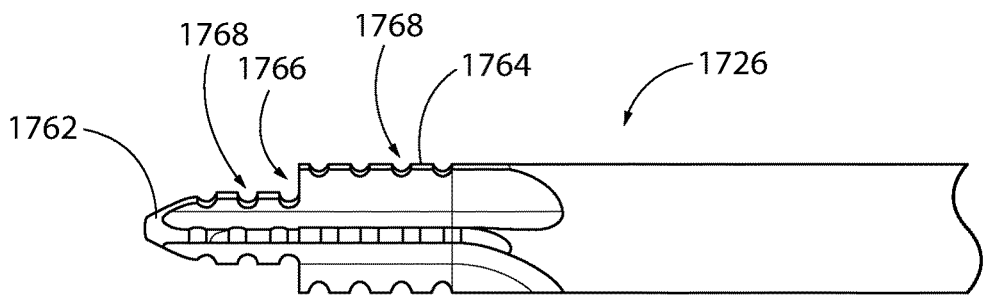
Figure 91C:
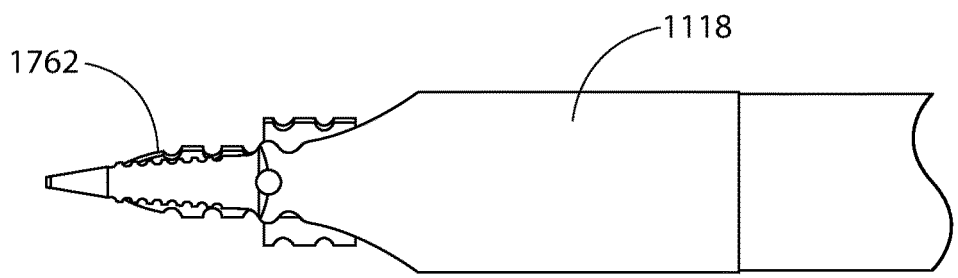
Figure 91D:
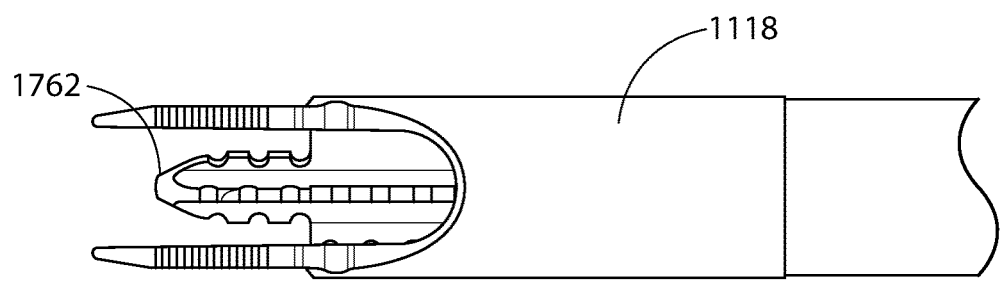

FIGS. 91A-91D are views of an embodiment of a delivery tool assembly including a decorticating burr 1726 and guide tube. FIGS. 91A and 91B show a distal end view and side view of the decorticator burr 1726. FIGS. 91C and 91D show a side view and a top view of the delivery tool assembly including the decorticator burr 1726 and guide tube 1118, with the decorticator burr 1726 positioned within the guide tube 118.

The decorticator burr 1726 includes a distal end formed by a pointed or tapered burr 1762. The burr 1726 may be cylindrical, or has a consistent cross-sectional area along the length of the burr 1762 aside from the pointed end. The unidirectional flutes of burr 1762 may extend the length of the burr 1762. The unidirectional flutes on the burr 1762 may be used to decorticate the bony surface when rotated in a clockwise direction. The leading, slim portion of the bur 1762 may be used to insert into the facet joint and decorticate inside the facet space. The burr 1762 may be referred to as the intra facet burr.

The decorticator burr 1726 may also include a burr 1764 positioned proximal to the intra facet burr 1762. The burr 1764 may be larger in diameter and be used to sit outside the facet joint and decorticate the space outside or below the facet, and may also be referred to as an outer facet burr. The combination of burr 1762 and burr 1764 may form a step drill. The burr 1764 may be cylindrical shaped, with unidirectional cutting flutes similar to those of burr 1762. In some examples, the decorticator burr 1726 includes straight cutting flutes that may be offset from the center and present a cutting edge when rotated. In some examples, the cutting flutes on the burr 1764 may be angled at a proximal end of the burr 1764. The angle of the flutes or cutting surfaces may be in between and including 10 and 25 degrees. A forward face 1766 of the burr 1764 may also include a uni-directional cutting flutes. In some examples, the decorticator burr 1726 includes chip breakers 1768 on the cutting burr 1762 and 1764 that may be used to break the chips formed from cutting from the bone into smaller chips to allow the decorticator burr 1726 to rotate more easily. In some examples, the chip breakers are placed along the cutting edge to prevent the device from snagging during rotation. The chip breakers may be staggered to each adjacent cross arm.

Figure 92A:
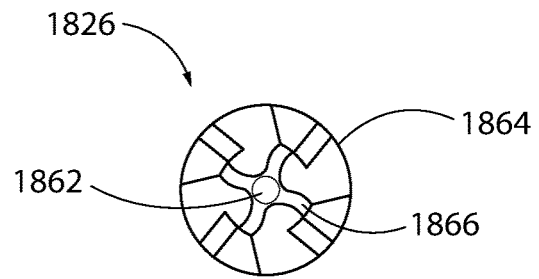
FIGS. 92A-92D are various views of an embodiment of a delivery tool assembly including a decorticating burr and guide tube.
Figure 92B:
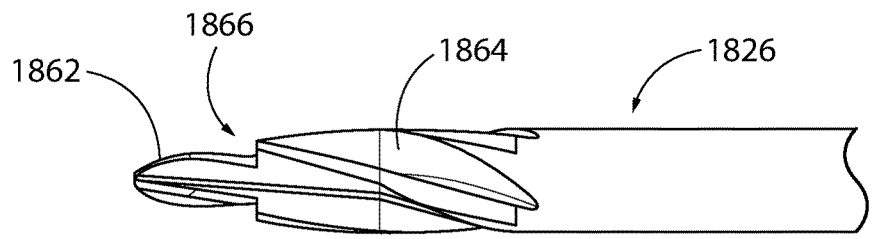
Figure 92C:
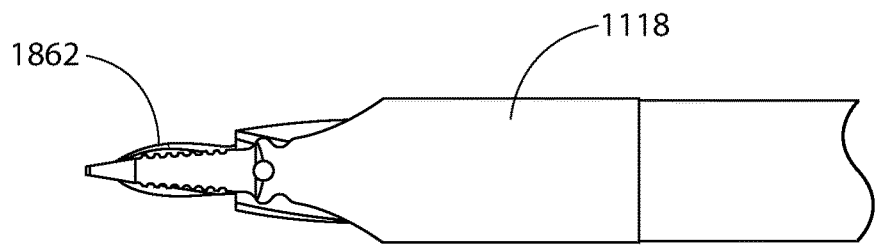
Figure 92D:
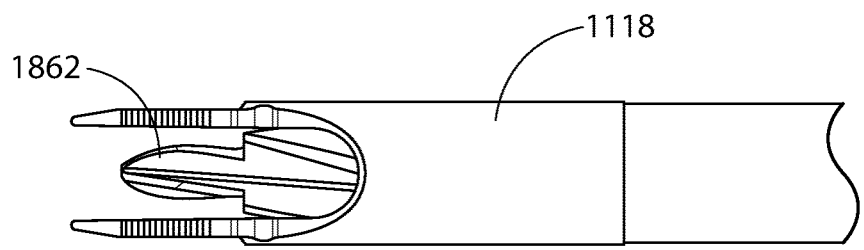

FIGS. 92A-92D are views of an embodiment of a delivery tool assembly including a decorticating burr 1826 and guide tube. FIGS. 92A and 92B show a distal end view and side view of the decorticator burr 1826. FIGS. 92C and 92D show a side view and a top view of the delivery tool assembly including the decorticator burr 1826 and guide tube 1118, with the decorticator burr 1826 positioned within the guide tube 1118.

The decorticator burr 1826 includes a distal end formed by a cylindrical shaped burr 1862 with a pointed end, having a consistent cross-sectional area the length of the burr 1862 up to the pointed end. In some examples, the burr 1862 may have a bullet, snub-nosed, or flat end. The angled, unidirectional flutes of burr 1862 may extend at least partially along the length of the burr 1562, but in some examples, may extend the full length of the burr 1862. The unidirectional flutes may be implemented so that the burr is rotated counter clockwise to decorticate the bone.

The decorticator burr 1826 may also include a burr 1864 positioned proximal to the burr 1862. The burr 1864 may be cylindrical shaped, with angled, uni-directional cutting flutes, and the combination of the burr 1862 and burr 1864 form a step drill-like instrument. A forward face 1866 of the burr 1864 may also include uni-directional cutting flutes. In some examples, the forward face 1866 does not include a cutting burr.

Figure 93:
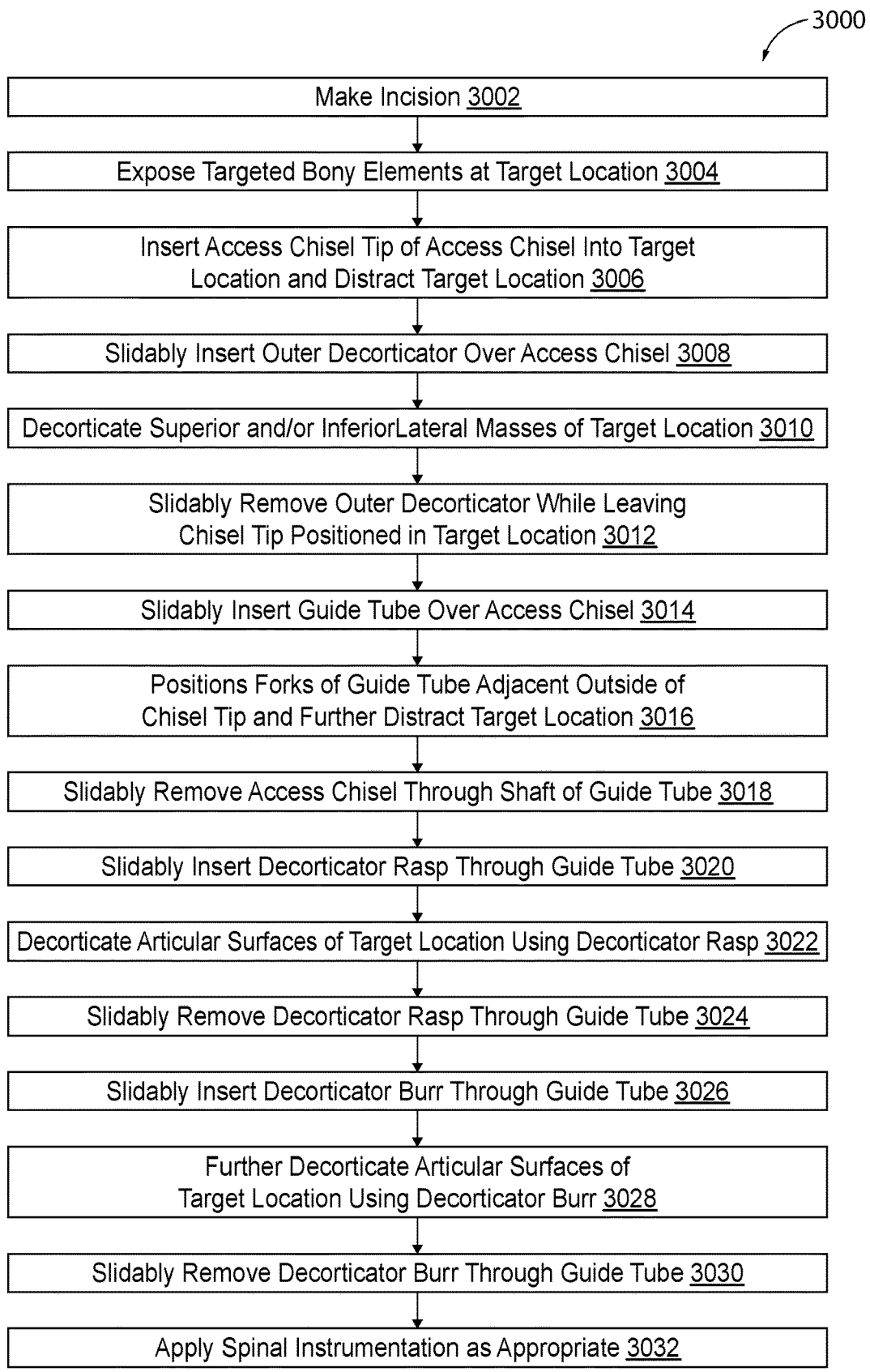
FIG. 93 illustrates a method for delivering a vertebral joint implant.

A method 3000 for delivering a vertebral joint implant is described in FIG. 93.

In block 3002, the method may include making an incision. In block 3004, the method may include exposing targeted bony elements at a target location. In block 3006, the method may include inserting an access chisel tip of an access chisel into the target location and distracting the target location. The access chisel of block 3006 may be similar to the previously described access chisels.

In block 3008, the method may include slidably inserting an outer decorticator over the access chisel. The outer decorticator of block 3008 may be similar to previously described outer decorticators. In block 3010, the method may include decorticating superior and/or inferior lateral masses of the target location. In block 3012, the method may include slidably removing the outer decorticator while leaving the chisel tip positioned in the target location.

In block 3014, the method may include slidably inserting a guide tube over the access chisel. The guide tube of block 3014 may be similar to the previously described guide tubes. In block 3016, the method may include positioning the forks of the guide tube adjacent an outside of the chisel tip and further distracting the target location. In block 3018, the method may include slidably removing the access chisel through a shaft of the guide tube.

In block 3020, the method may include slidably inserting a decorticator rasp through the guide tube. The decorticator rasp of block 3020 may be similar to previously described decorticator rasps. In block 3022, the method may include decorticating the articular surfaces of the target location using the decorticator rasp. In block 3024, method may include slidably removing the decorticator rasp through the guide tube.

In block 3026, the method may include slidably inserting a decorticator burr through the guide tube. The decorticator burr of block 3026 may be similar to previously described decorticator burrs. In block 3028, the method may include further decorticating the articular surfaces of the target location using the decorticator burr. In block 3030, the method may include slidably removing the decorticator burr through the guide tube. In block 3032, the method may include applying spinal instrumentation as appropriate. The spinal instrumentation of block 3032 may include, but is not limited to applying bone graft, inserting an implant, or various combinations thereof.

The delivery system or apparatus disclosed herein is advantageous for at least the following reasons. First, the system facilitates delivery of an implant to a facet joint via a minimally invasive or percutaneous procedure, reducing the risk, surgical time and recovery time associated with the implantation of the implant in the facet joint. Accordingly, many of the dimensional characteristics associated with the delivery system, its components, and the implant are advantageous in that they facilitate or make possible the minimally invasive or percutaneous procedures described herein. Second, the system may facilitate the implant being delivered while the patient is capable of providing verbal feedback as to the impact of the implant relative to symptoms being felt by the patient.

All relative and directional references (including: upper, lower, upward, downward, left, right, leftward, rightward, top, bottom, side, above, below, front, middle, back, vertical, horizontal, and so forth) are given by way of example to aid the reader's understanding of the particular examples described herein. They should not be read to be requirements or limitations, particularly as to the position, orientation, or use unless specifically set forth in the claims. Connection references (e.g., attached, coupled, connected, joined, and the like) are to be construed broadly and may include intermediate members between a connection of elements and relative movement between elements. As such, connection references do not necessarily infer that two elements are directly connected and in fixed relation to each other unless specifically set forth in the claims.

Those skilled in the art will appreciate that the presently disclosed embodiments teach by way of example and not by limitation. Therefore, the matter contained in the above description or shown in the accompanying drawings should be interpreted as illustrative and not in a limiting sense. Thus, it is intended that the scope of the present disclosure should not be limited by the particular examples described above.

What is claimed is:

1. A spinal facet joint system, the system comprising:
a guide tube for insertion into a spinal facet joint;
a decortication tool slidably and rotatably received within the guide tube to decorticate bone of the spinal facet joint, wherein the decortication tool comprises a decorticator burr comprising an intra facet burr and an outer facet burr,
an access chisel; and
a multi-use instrument, the multi-use instrument comprising:
a body including opposing first and second sides, and opposing first and second surfaces;
a cavity defined in the body, the cavity being open to the second surface; and
a bar attached to the second side of the body, wherein a portion of the bar extends beyond the second surface of the body,
wherein a portion of the access chisel is received within the cavity defined in the body of the instrument; and
the second surface of the body engages the guide tube to advance the guide tube along the access chisel and into the spinal facet joint.

2. The system of claim 1, wherein the guide tube includes a cutout or scallop feature formed on a bottom or lower portion of the distal end of the guide tube, the cutout or scallop feature configured to further expose the decortication tool to decorticate areas outside of or adjacent to the spinal facet joint.

3. The system of claim 1, wherein the guide tube includes a hard stop feature adjacent the distal end, the hard stop feature configured to prevent a distal end of the guide tube from being inserted into the spinal canal.

4. The system of claim 3, wherein the guide tube includes a curve feature positioned at or near the hard stop, the curve feature configured to provide a visualization landmark to aid in positioning the distal end of the guide tube.

5. The system of claim 1, wherein the guide tube defines a working cannula that includes a shape with at least one of a center hole, a concentric hole, or a four corner cutout, the working cannula configured to allow a variety of instruments to be used in conjunction with the guide tube.

6. The system of claim 1, wherein a distal end of the guide tube includes a visualization hole configured to provide a visualization landmark to aid in positioning the distal end of the guide tube.

7. The system of claim 1, wherein the decortication tool comprises a decorticator rasp.

8. The system of claim 1, wherein the decortication tool comprises a decorticator burr comprising a first burr and a second burr, wherein:
each burr includes unidirectional cutting flutes, or
each burr includes bi-directional cutting flutes.

9. The system of claim 1, wherein the decortication tool comprises an intra facet decorticator burr comprising a tip formed of at least one of a bullet, snub-nosed, pointed, blunt, tapered oval or prolate spheroid shape.

10. The system of claim 1, wherein the decortication tool comprises a decorticator burr comprising an intra facet burr and an outer facet burr that form a step drill.

11. The system of claim 1, wherein the access chisel comprises a distal portion and a proximal portion connected by a tubular shaft, the distal portion having a control feature to prevent the access chisel from advancing further into the facet joint, and provide stabilization for medial/lateral movement for improved controlled and targeted decortication.

12. The system of claim 11, further comprising an outer decorticator configured to decorticate at least one of a superior and inferior vertebrae lateral mass of the spinal facet joint.

13. The system of claim 12, wherein the outer decorticator includes a distal end formed with a plurality of bi-directional or uni-directional teeth.

14. The system of claim 11, wherein the control feature of the distal portion of the access chisel comprises a scalloped feature or hard stop feature configured to prevent the access chisel from advancing into a spinal canal.

15. The system of claim 11, wherein the control feature of the distal portion of the access chisel comprises a blade positioned on an upper surface of a tongue, the blade configured to provide stability and minimize unwanted medial/lateral movement.

16. The system of claim 11, wherein the control feature of the distal portion of the access chisel comprises an anti-backout feature on an underside of a tongue, the anti-backout feature configured to prevent the unintentional backout of the access chisel from the facet joint.

17. The system of claim 11, wherein the control feature of the distal portion of the access chisel comprises a notch feature at a distal tip, the notch configured to provide stability when the chisel is positioned at or near an entry point of the facet joint.

18. The system of claim 1, wherein the intra facet burr and the outer facet burr are coupled together.

19. A spinal facet joint system, the system comprising:
a guide tube for insertion into a spinal facet joint;
a decortication tool slidably and rotatably received within the guide tube to decorticate bone of the spinal facet joint;
an access chisel, the access chisel comprising a distal portion and a proximal portion connected by a tubular shaft, the distal portion having a control feature to prevent the access chisel from advancing further into the facet joint, and provide stabilization for medial/lateral movement for improved controlled and targeted decortication; and
a multi-use instrument,
the instrument comprising: a body including opposing first and second sides, and opposing first and second surfaces;
a cavity defined in the body, the cavity being open to the second surface; and
a bar attached to the second side of the body, wherein a portion of the bar extends beyond the second surface of the body,
wherein a portion of the access chisel is received within the cavity defined in the body of the instrument; and
the second surface of the body engages the guide tube to advance the guide tube along the access chisel and into the spinal facet joint.

* * * * *